(12) United States Patent
Orimoto et al.

(10) Patent No.: US 10,645,929 B2
(45) Date of Patent: May 12, 2020

(54) PYRIMIDINE COMPOUND

(71) Applicant: Sumitomo Chemical Company, Limited, Tokyo (JP)

(72) Inventors: Kohei Orimoto, Takarazuka (JP); Yoshihiko Nokura, Takarazuka (JP); Yuji Nakajima, Takarazuka (JP); Takamasa Tanabe, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 191 days.

(21) Appl. No.: 15/772,314

(22) PCT Filed: Oct. 26, 2016

(86) PCT No.: PCT/JP2016/081675
§ 371 (c)(1),
(2) Date: Apr. 30, 2018

(87) PCT Pub. No.: WO2017/077911
PCT Pub. Date: May 11, 2017

(65) Prior Publication Data
US 2018/0317485 A1  Nov. 8, 2018

(30) Foreign Application Priority Data

Nov. 2, 2015  (JP) .................................. 2015-215468

(51) Int. Cl.
| | |
|---|---|
| *A01N 43/54* | (2006.01) |
| *C07D 401/04* | (2006.01) |
| *C07D 239/34* | (2006.01) |
| *A61K 31/505* | (2006.01) |
| *A61K 31/506* | (2006.01) |
| *C07D 401/14* | (2006.01) |
| *C07D 413/14* | (2006.01) |
| *C07D 471/14* | (2006.01) |

(52) U.S. Cl.
CPC ............ *A01N 43/54* (2013.01); *A61K 31/505* (2013.01); *A61K 31/506* (2013.01); *C07D 239/34* (2013.01); *C07D 401/04* (2013.01); *C07D 401/14* (2013.01); *C07D 413/14* (2013.01); *C07D 471/14* (2013.01)

(58) Field of Classification Search
CPC .. C07D 239/34; C07D 401/04; C07D 401/14; C07D 413/14; C07D 471/14
See application file for complete search history.

(56) References Cited

U.S. PATENT DOCUMENTS

| 4,769,364 A | 9/1988 | Maurer et al. |
|---|---|---|
| 2015/0239847 A1 | 8/2015 | Heilmann et al. |
| 2016/0081339 A1 | 3/2016 | Yoshimoto et al. |
| 2016/0237059 A1 | 8/2016 | Straub et al. |
| 2016/0251321 A1 | 9/2016 | Alig et al. |
| 2017/0305864 A1 | 10/2017 | Heilmann et al. |
| 2017/0305896 A1 | 10/2017 | Tanabe et al. |

FOREIGN PATENT DOCUMENTS

| EP | 3202761 A1 | 8/2017 |
|---|---|---|
| EP | 3252041 A1 | 12/2017 |
| JP | S62033192 A | 2/1987 |
| JP | 2000026421 A | 1/2000 |
| WO | 2013027660 A1 | 2/2013 |
| WO | 2014053450 A1 | 4/2014 |
| WO | 2014175465 A1 | 10/2014 |
| WO | 2015004028 A1 | 1/2015 |
| WO | 2015036560 A1 | 3/2015 |
| WO | 2016052247 A1 | 4/2016 |

OTHER PUBLICATIONS

Extended European Search Report dated Mar. 27, 2019 in EP Application No. 16861973.2.
English Translation of International Preliminary Report on Patentability dated May 8, 2018 in International Application No. PCT/JP2016/081675.
English Translation of International Search Report dated Dec. 27, 2016 in International Application No. PCT/JP2016/081675.
Office Action dated Jan. 23, 2020 in IN Application No. 201847019795.

*Primary Examiner* — Kortney L. Klinkel
(74) *Attorney, Agent, or Firm* — Panitch Schwarze Belisario & Nadel LLP

(57) ABSTRACT

Provided is a compound represented by formula (I), or an N-oxide thereof:

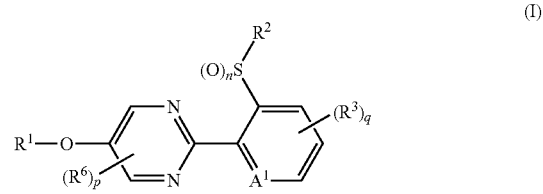

wherein: $A^1$ represents a nitrogen atom or a $CR^4$; $R^4$ represents a hydrogen atom or the like; $R^1$ represents a C2-C10 chain hydrocarbon group having one or more halogen atoms or the like; $R^2$ represents a C1-C6 alkyl group optionally having one or more halogen atoms or the like; q represents 0, 1, 2, or 3; $R^3$ represents a C1-C6 chain hydrocarbon group optionally having one or more substituents selected from Group B or the like; p represents 0, 1, or 2; $R^6$ represents a C1-C6 alkyl group optionally having one or more halogen atoms or the like; and n represents 0, 1, or 2. The compound of formula (I) has excellent control efficacies against harmful arthropods.

14 Claims, No Drawings

PYRIMIDINE COMPOUND

TECHNICAL FIELD

The present invention relates to a certain class of compound and its use for controlling harmful arthropods.

BACKGROUND ART

To date, some compounds for controlling harmful arthropods have been developed and come into practical use.

Also, a certain class of heterocyclic compounds has been known (for example, see Patent Document 1).

CITATION LIST

Patent Document

Patent Document 1: JP 2000-26421 A

SUMMARY OF THE INVENTION

Problems to be Solved by Invention

An object of the present invention is to provide a compound having excellent control efficacies against harmful arthropods.

Means to Solve Problems

The present invention provides the followings.
[1] A compound represented by formula (I)

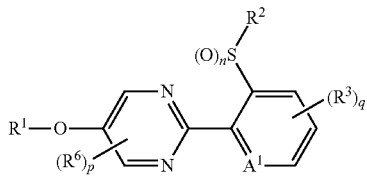

[wherein:
$A^1$ represents a nitrogen atom or a $CR^4$;
$R^4$ represents a hydrogen atom, a $OR^{27}$, a $NR^{27}R^{28}$, a cyano group, a nitro group, or a halogen atom;
$R^1$ represents a C2-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;
$R^2$ represents a C1-C6 alkyl group optionally having one or more halogen atoms, a cyclopropylmethyl group, or a cyclopropyl group;
q represents 0, 1, 2, or 3
wherein when q represents 1, 2, or 3, $R^3$ represents a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^1$, a $NR^{11}R^{12}$, a $NR^{11a}R^{12a}$, a $NR^{29}NR^{11}R^{12}$, a $NR^{24}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15}R^{16}$, a $NR^{29}NR^{11}C(O)NR^{15}R^{16}$, a N=CHNR$^{15}$R$^{16}$, a N=S(O)$_x$R$^{15}$R$^{16}$, a S(O)$_y$R$^{15}$, a C(O)OR$^{17}$, a C(O)NR$^{11}$R$^{12}$, a cyano group, a nitro group, or a halogen atom, and
wherein when q represents 2 or 3, two or three $R^3$ may be identical to or different from each other;
p represents 0, 1, or 2
wherein when p represents 1 or 2, $R^6$ represents a C1-C6 alkyl group optionally having one or more halogen atoms, a $OR^{18}$, a $NR^{18}R^{19}$, a cyano group, a nitro group, or a halogen atom, and
wherein when p represents 2, two $R^6$ may be identical to or different from each other;
$R^{11}$, $R^{17}$, $R^{18}$, $R^{19}$, $R^{24}$, and $R^{29}$ represent each independently a hydrogen atom or a C1-C6 chain hydrocarbon group optionally having one or more halogen atoms;
$R^{12}$ represents a hydrogen atom, a C1-C6 chain hydrocarbon group optionally having one or more halogen atoms, a C1-C6 alkyl group having one substituent selected from Group F, or a $S(O)_2R^{23}$;
$R^{23}$ represents a C1-C6 chain hydrocarbon group optionally having one or more halogen atoms or a phenyl group optionally having one or more substituents selected from Group D;
$R^{11a}$ and $R^{12a}$ are combined with the nitrogen atom to which they are attached to represent a 3-7 membered nonaromatic heterocyclic group optionally having one or more substituents selected from Group E {wherein said 3-7 membered nonaromatic heterocyclic group represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring};
$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a 5 or 6 membered aromatic heterocyclic group optionally having one or more substituents selected from Group D;
$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group (wherein the phenyl moiety in the phenyl C1-C3 alkyl group may optionally have one or more substituents selected from Group D);
$R^{15}$ and $R^{16}$ represent each independently a C1-C6 alkyl group optionally having one or more halogen atoms;
$R^{27}$ and $R^{28}$ represent each independently a hydrogen atom or a C1-C6 alkyl group optionally having one or more halogen atoms;
n and y represent each independently 0, 1, or 2;
x represents 0 or 1;
Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom {wherein $R^{21}$ and $R^{22}$ represent each independently a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a 5 or 6 membered aromatic heterocyclic group optionally having one or more substituents selected from Group D, a C3-C7 cycloalkyl group optionally having one or more halogen atoms, and a 3-7 membered nonaromatic heterocyclic group optionally having one or more substituents selected from Group C;

Group G: a group consisting of a halogen atom and a C1-C6 haloalkyl group]
or an N-oxide compound thereof (hereinafter a compound represented by formula (I) or an N-oxide compound thereof is referred to as "compound of the present invention" or "Present compound").

[2] The compound according to [1], wherein
$R^4$ represents a hydrogen atom or a halogen atom; and
$R^3$ represents a C1-C6 chain hydrocarbon group optionally having one or more halogen atoms, a phenyl group optionally having one or more substituents selected from Group D, a 6 membered aromatic heterocyclic group comprising 1 to 2 nitrogen atoms (wherein said 6 membered aromatic heterocyclic group may optionally have one or more substituents selected from Group D), a 5 membered aromatic heterocyclic group comprising 1 to 4 nitrogen atoms (wherein said 5 membered aromatic heterocyclic group may optionally have one or more substituents selected from Group D), a $OR^{12}$, a $NR^{11}R^{12}$, or a halogen atom.

[3] The compound according to [1], wherein
$R^3$ represents a C1-C6 alkyl group having one or more halogen atoms, a $OR^{12}$, a $NR^{11}R^{12}$, or a halogen atom; and
$R^{11}$ and $R^{12}$ represent each independently a hydrogen atom or a C1-C3 alkyl group optionally having one or more halogen atoms.

[4] The compound according to [1], wherein
q represents 0; and
$R^4$ represents a hydrogen atom.

[5] The compound according to any one of [1] to [4], wherein p represents 0.

[6] The compound according to any one of [1] to [5], wherein $R^1$ represents a C2-C10 haloalkyl group.

[7] The compound according to any one of [1] to [5], wherein $R^1$ represents a C2-C10 fluoroalkyl group.

[8] The compound according to any one of [1] to [5], wherein $R^1$ represents a C3-C5 alkyl group having four or more fluorine atoms.

[9] The compound according to any one of [1] to [8], wherein $R^2$ represents a C1-C6 alkyl group optionally having one or more halogen atoms.

[10] The compound according to any one of [1] to [8], wherein $R^2$ represents an ethyl group.

[11] The compound according to [1], wherein
$R^1$ represents a C2-C10 haloalkyl group;
$R^2$ represents an ethyl group;
q represents 0 or 1;
$R^3$ represents a C1-C6 alkyl group optionally having one or more halogen atoms, or a halogen atom;
p represents 0 or 1; and
$R^6$ represents a C1-C6 alkyl group optionally having one or more halogen atoms, or a halogen atom.

[12] The compound according to [1], wherein
$R^1$ represents a C3-C5 alkyl group having four or more fluorine atoms;
$R^2$ represents an ethyl group;
q represents 0; and
p represents 0.

[13] A composition for controlling a harmful arthropod comprising the compound according to any one of [1] to [12] and an inert carrier.

[14] A method for controlling a harmful arthropod which comprises applying an effective amount of the compound according to any one of [1] to [12] to a harmful arthropod or a habitat where a harmful arthropod lives.

Effect of Invention

The Present compound has excellent control efficacies against harmful arthropods, and thus is useful as an active ingredient of an agent for controlling harmful arthropod.

MODE FOR CARRYING OUT THE INVENTION

The substituent(s) in the present invention is/are explained as follows.

When a substituent "optionally having one or more halogen atoms" has two or more halogen atoms, these halogen atoms may be identical to or different from each other.

The expression of "CX—CY" as described herein means that the number of carbon atom is X to Y. For example, the expression of "C1-C6" means that the number of carbon atom is 1 to 6.

The term of "halogen atom" represents fluorine atom, chlorine atom, bromine atom, or iodine atom.

The term of "chain hydrocarbon group" represents an alkyl group, an alkenyl group, and an alkynyl group.

Examples of the term of "alkyl group" include methyl group, ethyl group, propyl group, isopropyl group, 1,1-dimethylpropyl group, 1,2-dimethylpropyl group, 1-ethylpropyl group, butyl group, tert-butyl group, pentyl group, and hexyl group.

Examples of the term of "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 1-ethyl-1-propenyl group, 1-ethyl-2-propenyl group, 3-butenyl group, 4-pentenyl group, and 5-hexenyl group.

Examples of the term of "alkynyl group" include ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, and 5-hexynyl group.

The term of "C2-C10 haloalkyl group" represents a C2-C10 alkyl group wherein one or more hydrogen atoms are substituted with one or more halogen atoms, and examples thereof include a C2-C10 fluoroalkyl group.

Examples of the term of "C2-C10 haloalkyl group" include chloroethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, perfluorohexyl group, and perfluorodecyl group.

Examples of the term of "C2-C10 fluoroalkyl group" include 2,2,2-trifluoroethyl group, 2,2,3,3-tetrafluoropropyl group, 1-methyl-2,2,3,3-tetrafluoropropyl group, perfluorohexyl group, and perfluorodecyl group.

Examples of the term of "cycloalkyl group" include cyclopropyl group, cyclobutyl group, cyclopentyl group, cyclohexyl group, and cycloheptyl group.

The term of "3-7 membered nonaromatic heterocyclic group" represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring, and examples of "3-7 membered nonaromatic heterocyclic group optionally having one or more substituents selected from Group E" include the following groups.

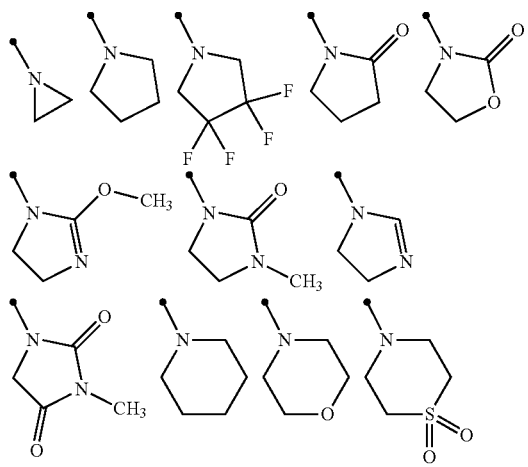

Examples of the term of "phenyl C1-C3 alkyl group {wherein the phenyl moiety in the phenyl C1-C3 alkyl group may optionally have one or more substituents selected from Group D}" include benzyl group, 2-fluorobenzyl group, 4-chlorobenzyl group, 4-(trifluoromethyl)benzyl group, and 2-[4-(trifluoromethyl)phenyl]ethyl group.

The term of "(C1-C5 alkoxy)C2-C5 alkyl group having one or more halogen atoms" represents a group wherein the (C1-C5 alkoxy) and/or the (C2-C5 alkyl) has one or more halogen atoms, and examples thereof include 2-(trifluoromethoxy)ethyl group, 2,2-difluoro-3-methoxypropyl group, 2,2-difluoro-3-(2,2,2-trifluoroethoxy)propyl group, and 3-(2-chloroethoxy)propyl group.

The term of "(C1-C5 alkylsulfanyl)C2-C5 alkyl group having one or more halogen atoms" represents a group wherein the (C1-C5 alkylsulfanyl) and/or the (C2-C5 alkyl) has one or more halogen atoms, and examples thereof include 2,2-difluoro-2-(trifluoromethylthio)ethyl group.

The term of "(C1-C5 alkylsulfinyl)C2-C5 alkyl group having one or more halogen atoms" represents a group wherein the (C1-C5 alkylsulfinyl) and/or the (C2-C5 alkyl) has one or more halogen atoms, and examples thereof include 2,2-difluoro-2-(trifluoromethanesulfinyl)ethyl group.

The term of "(C1-C5 alkylsulfonyl)C2-C5 alkyl group having one or more halogen atoms" represents a group wherein the (C1-C5 alkylsulfonyl) and/or the (C2-C5 alkyl) has one or more halogen atoms, and examples thereof include 2,2-difluoro-2-(trifluoromethanesulfonyl)ethyl group.

The term of "(C3-C6 cycloalkyl)C1-C3 alkyl group optionally having one or more halogen atoms" represents a group wherein the (C3-C6 cycloalkyl) and/or the (C1-C3 alkyl) may be optionally substituted with one or more halogen atoms, and examples thereof include (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

The term of "(C3-C7 cycloalkyl)C1-C3 alkyl group having one or more substituents selected from Group G" represents a group wherein the (C3-C7 cycloalkyl) and/or the (C1-C3 alkyl) has one or more substituents selected from Group G, and examples thereof include (2,2-difluorocyclopropyl)methyl group, [1-(trifluoromethyl)cyclopropyl]methyl group, [2-(trifluoromethyl)cyclopropyl]methyl group, 2-cyclopropyl-1,1,2,2-tetrafluoroethyl group, 2-cyclopropyl-3,3,3-trifluoropropyl group, and 1,1,2,2-tetrafluoro-2-[2-(trifluoromethyl)cyclopropyl]ethyl group.

Examples of the term of "C3-C7 cycloalkyl group having one or more substituents selected from Group G" include 2,2-difluorocyclopropyl group, 1-(2,2,2-trifluoroethyl)cyclopropyl group, and 4-(trifluoromethyl)cyclohexyl group.

The term of "5 or 6 membered aromatic heterocyclic group" represents a 5 membered aromatic heterocyclic group or a 6 membered aromatic heterocyclic group, and the term of "5 membered aromatic heterocyclic group" represents pyrrolyl group, furyl group, thienyl group, pyrazolyl group, imidazolyl group, triazolyl group, tetrazolyl group, oxazolyl group, isoxazolyl group, thiazolyl group, oxadiazolyl group, or thiadiazolyl group, and the term of "6 membered aromatic heterocyclic group" represents pyridyl group, pyridazinyl group, pyrimidinyl group, or pyrazinyl group.

The term of "5 membered aromatic heterocyclic group comprising 1 to 4 nitrogen atoms" represents pyrrolyl group, pyrazolyl group, imidazolyl group, 1,2,4-triazolyl group, 1,2,3-triazolyl group, or tetrazolyl group.

The term of "N-oxide compound" represents a compound represented by the following formula (I-N1) or a compound represented by the following formula (I-N2).

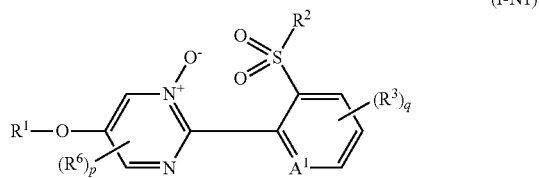
(I-N1)

[wherein the symbols are the same as defined above.]

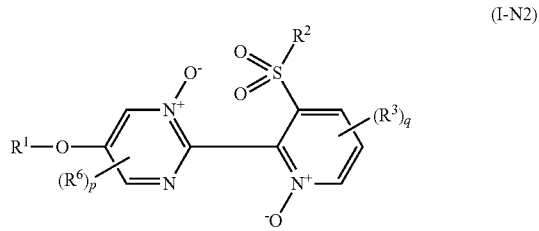
(I-N2)

[wherein the symbols are the same as defined above.]

Embodiments of the Present compound include the following compounds.

The Present compound, wherein $R^4$ represents a hydrogen atom or a halogen atom;

The Present compound, wherein $A^1$ represents a nitrogen atom or a CH;

The Present compound, wherein $R^1$ represents a C2-C10 haloalkyl group or a (C3-C7 cycloalkyl)C1-C3 alkyl group having one or more substituents selected from Group G;

The Present compound, wherein $R^1$ represents a C2-C10 haloalkyl group;

The Present compound, wherein $R^1$ represents a C2-C10 alkyl group having two or more fluorine atoms;

The Present compound, wherein $R^1$ represents a C2-C6 alkyl group having four or more fluorine atoms;

The Present compound, wherein $R^2$ represents a C1-C6 alkyl group optionally having one or more halogen atoms;

The Present compound, wherein $R^2$ represents a C1-C6 alkyl group;

The Present compound, wherein $R^2$ represents a methyl group or an ethyl group;

The Present compound, wherein $R^2$ represents an ethyl group;

The Present compound, wherein $R^4$ represents a hydrogen atom or a halogen atom, and $R^3$ represents a C1-C6 chain hydrocarbon group optionally having one or more halogen atoms, a 5 membered aromatic heterocyclic group comprising 1 to 4 nitrogen atoms (wherein said 5 membered aromatic heterocyclic group may optionally have one or more substituents selected from Group D), a $NR^{11}R^{12}$, or a halogen atom;

The Present compound, wherein $R^4$ represent a hydrogen atom, $R^3$ represents a C1-C6 alkyl group having one or more halogen atoms, a $NR^{11}R^{12}$, or a halogen atom, and $R^{11}$ and $R^{12}$ represent each independently a hydrogen atom or a C1-C3 alkyl group optionally having one or more halogen atoms;

The Present compound, wherein $R^3$ represents a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, $NR^{11}R^{12}$, a $NR^{11a}R^{12a}$, a $S(O)_yR^{15}$, or a halogen atom;

The Present compound, wherein q represents 0, 1, or 2, and $R^3$ represents each independently a C1-C6 chain hydrocarbon group optionally having one or more substituents selected from Group B, a phenyl group optionally having one or more substituents selected from Group D, a 6 membered aromatic heterocyclic group selected from Group R (wherein said 6 membered aromatic heterocyclic group may optionally have one or more substituents selected from Group D), a 5 membered aromatic heterocyclic group selected from Group Q (wherein said 5 membered aromatic heterocyclic group may optionally have one or more substituents selected from Group D), a $OR^{12}$, a $NR^{11}R^{12}$, a $NR^{11a}R^{12a}$, a $NR^{29}NR^{11}R^{12}$, a $S(O)_yR^{15}$, or a halogen atom;

Group R:

R-1

R-2

R-3

R-4

R-5

R-6

R-7

R-8

R-9

R-10
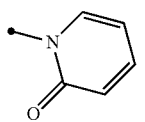

R-11
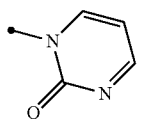

R-12
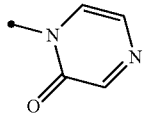

R-13
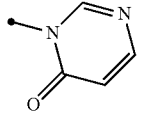

R-14
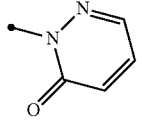

R-15
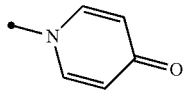

R-16
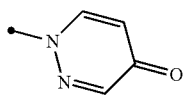

R-17
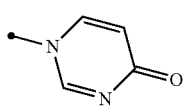

The Present compound, wherein q represents 0, 1, or 2, $R^3$ represents a C1-C6 chain hydrocarbon group optionally having one or more substituents selected from Group B, a 5 membered aromatic heterocyclic group selected from Group Q (wherein said 5 membered aromatic heterocyclic group may optionally have one or more substituents selected from Group D), a $OR^{12}$, a $NR^{11}R^{12}$, a $NR^{11a}R^{12a}$, a $NR^{29}NR^{11}R^{12}$, a $NR^{24}OR^{11}$, a $S(O)_yR^{15}$, or a halogen atom;

Group Q:

Q-1
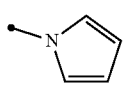

Q-2
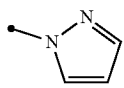

Q-3
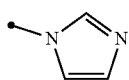

Q-4
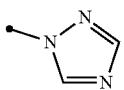

Q-5
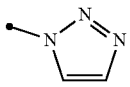

Q-6
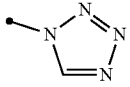

Q-7
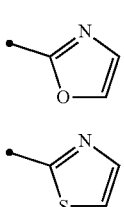

Q-8
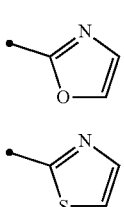

Q-9
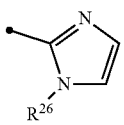

Q-10
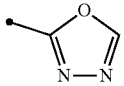

Q-11
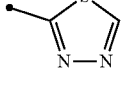

Q-12
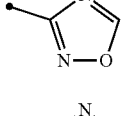

Q-13
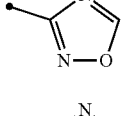

Q-14
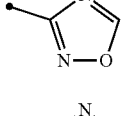

Q-15
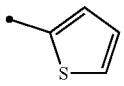

Q-16
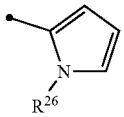

Q-17
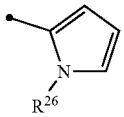

Q-18
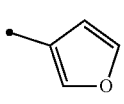

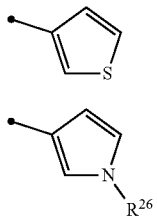

{wherein $R^2$ represents a C1-C6 alkyl group optionally having one or more halogen atoms.}

The Present compound, wherein q represents 0, 1, or 2, and $R^3$ represents a C1-C6 chain hydrocarbon group optionally having one or more halogen atoms, a 5 membered aromatic heterocyclic group comprising 1 to 4 nitrogen atoms (wherein said 5 membered aromatic heterocyclic group may optionally have one or more substituents selected from Group D), a $OR^{12}$, a $NR^{11}R^{12}$, a $NR^{29}NR^{11}R^{12}$, a $NR^{24}OR^{11}$, a $S(O)_yR^{15}$, or a halogen atom, wherein when q represents 2, two $R^3$ may be identical to or different from each other;

The Present compound, wherein q represents 0 or 1, and $R^3$ represents a C1-C6 alkyl group optionally having one or more halogen atoms, or a halogen atom;

The Present compound, wherein q represents 0;

The Present compound, wherein $R^6$ represents a C1-C6 alkyl group optionally having one or more halogen atoms, or a halogen atom;

The Present compound, wherein p represents 0 or 1, and $R^6$ represents a C1-C6 alkyl group optionally having one or more halogen atoms, a $OR^{18}$, a $NR^{18}R^{19}$, a cyano group, a nitro group, or a halogen atom;

The Present compound, wherein p represents 0 or 1, and $R^6$ represents a C1-C6 alkyl group optionally having one or more halogen atoms, or a halogen atom;

The Present compound, wherein p represents 0;

The Present compound, wherein $R^4$ represents a hydrogen atom or a halogen atom, $R^1$ represents a C2-C10 haloalkyl group, $R^2$ represents a C1-C6 alkyl group optionally having one or more halogen atoms, q represents 0, 1, or 2, and $R^3$ represents a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{29}NR^{11}R^{12}$, a $NR^{24}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15}R^{16}$, a $NR^{24}NR^{11}C(O)NR^{15}R^{16}$, a N=CHNR$^{15}$R$^{16}$, a N=S(O)$_z$R$^{15}$R$^{16}$, a $S(O)_yR^{15}$, a $C(O)OR^{17}$, a $C(O)NR^{11}R^{12}$, a cyano group, a nitro group, or a halogen atom;

The Present compound, wherein $A^1$ represents a nitrogen atom or a CH, $R^1$ represents a C2-C10 haloalkyl group, $R^2$ represents an ethyl group, q represents 0, 1, or 2, and $R^3$ represents a C1-C6 chain hydrocarbon group optionally having one or more substituents selected from Group B, a 5 or 6 membered aromatic heterocyclic group optionally having one or more substituents selected from Group D, a $OR^{12}$, a $NR^{11}R^{12}$, a $NR^{11a}R^{12a}$, a $S(O)_yR^{15}$, or a halogen atom, and $R^6$ represents a C1-C6 alkyl group optionally having one or more halogen atoms, or a halogen atom;

The Present compound, wherein $A^1$ represents a nitrogen atom or a CH, $R^1$ represents a C2-C10 alkyl group having two or more fluorine atoms, $R^2$ represents an ethyl group, q represents 0 or 1, $R^3$ represents a C1-C6 alkyl group optionally having one or more halogen atoms, or a halogen atom, and p represents 0;

The Present compound, wherein $A^1$ represents a nitrogen atom or a CH, $R^1$ represents a C3-C6 alkyl group having four or more fluorine atoms, $R^2$ represents an ethyl group, q represents 0, 1, or 2, $R^3$ represents a C1-C6 alkyl group optionally having one or more halogen atoms, a 5 membered aromatic heterocyclic group selected from Group Q (wherein said 5 membered aromatic heterocyclic group may optionally have one or more substituents selected from Group D), a $OR^{12}$, a $NR^{11}R^{12}$, a $NR^{11a}R^{12a}$, or a halogen atom, and $R^6$ represents a C1-C6 alkyl group optionally having one or more halogen atoms, or a halogen atom;

The Present compound, wherein $A^1$ represents a nitrogen atom or a CH, $R^1$ represents a C3-C6 haloalkyl group having four or more fluorine atoms, $R^2$ represents an ethyl group, q represents 0 or 1, $R^3$ represents a C1-C6 alkyl group optionally having one or more halogen atoms, and p represents 0;

A compound represented by formula (I-A)

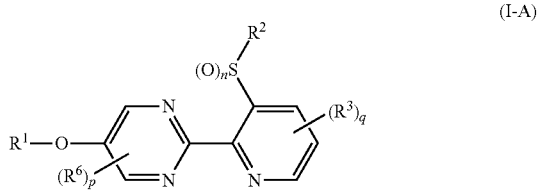

(I-A)

[wherein the symbols are the same as defined above.]
(hereinafter referred to as "Present compound (I-A)").

The Present compound (I-A), wherein $R^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl) C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms, $R^2$ represents a C1-C6 alkyl group, q represents 0 or 1, $R^3$ represents a C1-C6 alkyl group optionally having one or more halogen atoms, and p represents 0;

The Present compound (I-A), wherein $R^1$ represents a C2-C10 haloalkyl group, and $R^2$ represents a C1-C6 alkyl group optionally having one or more halogen atoms;

The Present compound (I-A), wherein $R^1$ represents a C2-C10 haloalkyl group, $R^2$ represents an ethyl group, $R^3$ represents a C1-C6 chain hydrocarbon group optionally having one or more substituents selected from Group B, a 5 or 6 membered aromatic heterocyclic group optionally having one or more substituents selected from Group D, a $OR^{12}$, a $NR^{11}R^{12}$, a $NR^{11a}R^{12a}$, a $S(O)_yR^{15}$, or a halogen atom, and $R^6$ represents a C1-C6 alkyl group optionally having one or more halogen atoms, or a halogen atom;

The Present compound (I-A), wherein $R^1$ represents a C2-C10 haloalkyl group, $R^2$ represents a C1-C6 alkyl group, q represents 0 or 1, $R^3$ represents a C1-C6 alkyl group optionally having one or more halogen atoms, and p represents 0;

The Present compound (I-A), wherein $R^1$ represents a C2-C10 alkyl group having two or more fluorine atoms, $R^2$ represents an ethyl group, $R^3$ represents a C1-C6 alkyl group optionally having one or more halogen atoms, or a halogen atom, and p represents 0;

The Present compound (I-A), wherein $R^1$ represents a C3-C6 alkyl group having four or more fluorine atoms, $R^2$ represents an ethyl group, $R^3$ represents a C1-C6 alkyl group optionally having one or more halogen atoms, a 5 membered aromatic heterocyclic group selected from Group Q (wherein said 5 membered aromatic heterocyclic group may optionally have one or more substituents selected from Group D), a $OR^{12}$, a $NR^{11}R^{12}$, a $NR^{11a}R^{12a}$, or a halogen atom, and $R^6$ represents a C1-C6 alkyl group optionally having one or more halogen atoms, or a halogen atom;

The Present compound (I-A), wherein $R^1$ represents a C3-C6 haloalkyl group having four or more fluorine atoms, $R^2$ represents an ethyl group, q represents 0, and p represents 0;

The Present compound (I-A), wherein $R^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms, $R^2$ represents a C1-C6 alkyl group, q represents 0 or 1, $R^3$ represents a C1-C6 chain hydrocarbon group optionally having one or more halogen atoms, a phenyl group optionally having one or more substituents selected from Group D, a 6 membered aromatic heterocyclic group selected from R-1 to R-9 (wherein said 6 membered aromatic heterocyclic group may optionally have one or more substituents selected from Group D), a 5 membered aromatic heterocyclic group selected from Q-1 to Q-7 (wherein said 5 membered aromatic heterocyclic group may optionally have one or more substituents selected from Group D), a $OR^{12}$, a $NR^{11}R^{12}$, or a halogen atom, and p represents 0;

The Present compound (I-A), wherein $R^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms, $R^3$ represents a C1-C6 alkyl group, q represents 0 or 1, $R^3$ represents a C1-C6 chain hydrocarbon group optionally having one or more halogen atoms, a phenyl group optionally having one or more substituents selected from Group D, a 6 membered aromatic heterocyclic group selected from R-1 to R-9 (wherein said 6 membered aromatic heterocyclic group may optionally have one or more substituents selected from Group D), a $OR^{12}$, a $NR^{11}R^{12}$, or a halogen atom, and p represents 0.

A compound represented by formula (I-B)

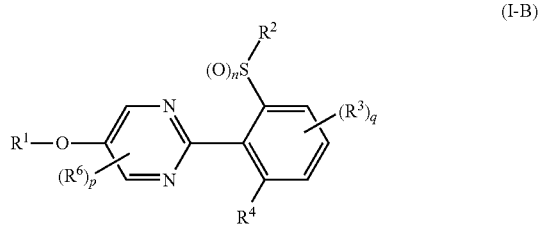

(I-B)

[wherein the symbols are the same as defined above.] (hereinafter referred to as "Present compound (I-B)").

The Present compound (I-B), wherein $R^4$ represents a hydrogen atom or a halogen atom, $R^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms, $R^2$ represents a C1-C6 alkyl group, q represents 0 or 1, $R^3$ represents a C1-C6 chain hydrocarbon group optionally having one or more halogen atoms, a phenyl group optionally having one or more substituents selected from Group D, a 6 membered aromatic heterocyclic group selected from R-1 to R-9 (wherein said 6 membered aromatic heterocyclic group may optionally have one or more substituents selected from Group D), a 5 membered aromatic heterocyclic group selected from Q-1 to Q-7 (wherein said 5 membered aromatic heterocyclic group may optionally have one or more substituents selected from Group D), a $OR^{12}$, a $NR^{11}R^{12}$, or a halogen atom, and p represents 0;

The Present compound (I-B), wherein $R^4$ represents a hydrogen atom or a halogen atom, $R^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms, $R^2$ represents a C1-C6 alkyl group, q represents 0 or 1, $R^3$ represents a C1-C6 chain hydrocarbon group optionally having one or more halogen atoms, a phenyl group optionally having one or more substituents selected from Group D, a 6 membered aromatic heterocyclic group selected from R-1 to R-9 (wherein said 6 membered aromatic heterocyclic group may optionally have one or more substituents selected from Group D), a $OR^{12}$, a $NR^{11}R^{12}$, or a halogen atom, and p represents 0;

The Present compound (I-B), wherein $R^4$ represents a hydrogen atom or a halogen atom, $R^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms, $R^2$ represents a C1-C6 alkyl group, q represents 0 or 1, $R^3$ represents a C1-C6 alkyl group optionally having one or more halogen atoms, and p represents 0;

The Present compound (I-B), wherein $R^4$ represents a hydrogen atom or a halogen atom, $R^1$ represents a C2-C10 haloalkyl group, and $R^2$ represents a C1-C6 alkyl group optionally having one or more halogen atoms;

The Present compound (I-B), wherein $R^4$ represents a hydrogen atom or a halogen atom, $R^1$ represents a C2-C10 haloalkyl group, $R^2$ represents an ethyl group, $R^3$ represents a C1-C6 chain hydrocarbon group optionally having one or more substituents selected from Group B, a 5 or 6 membered aromatic heterocyclic group optionally having one or more substituents selected from Group D, a $OR^{12}$, a $NR^{11}R^{12}$, a $NR^{11a}R^{12a}$, a $S(O)_yR^{15}$, or a halogen atom, and $R^6$ represents a C1-C6 alkyl group optionally having one or more halogen atoms, or a halogen atom;

The Present compound (I-B), wherein $R^1$ represents a C2-C10 haloalkyl group, $R^2$ represents a C1-C6 alkyl group, q represents 0 or 1, $R^3$ represents a C1-C6 alkyl group optionally having one or more halogen atoms, and p represents 0;

The Present compound (I-B), wherein $R^4$ represents a hydrogen atom;

The Present compound (I-B), wherein $R^4$ represents a hydrogen atom, $R^1$ represents a C2-C10 alkyl group having two or more fluorine atoms, $R^2$ represents an ethyl group, q represents 0 or 1, $R^3$ represents a C1-C6 alkyl group optionally having one or more halogen atoms, or a halogen atom, and p represents 0;

The Present compound (I-B), wherein $R^4$ represents a hydrogen atom, $R^1$ represents a C3-C6 alkyl group having four or more fluorine atoms, $R^2$ represents an ethyl group, $R^3$ represents a C1-C6 alkyl group optionally having one or more halogen atoms, a 5 membered aromatic heterocyclic group selected from Group Q (wherein said 5 membered aromatic heterocyclic group may optionally have one or more substituents selected from Group D), a $OR^{12}$, a $NR^{11}R^{12}$, a $NR^{11a}R^{12a}$, or a halogen atom, and $R^6$ represents a C1-C6 alkyl group optionally having one or more halogen atoms, or a halogen atom;

The Present compound (I-B), wherein $R^4$ represents a hydrogen atom, $R^1$ represents a C3-C6 haloalkyl group having four or more fluorine atoms, $R^2$ represents an ethyl group, q represents 1, $R^3$ represents a C1-C6 alkyl group optionally having one or more halogen atoms, and p represents 0;

Next, processes for preparing the Present compound are described.

The Present compound can be prepared, for example, according to the following processes.

Process 1

A compound represented by formula (Ib) (hereinafter referred to as "Present compound (Ib)") and a compound represented by formula (Ic) (hereinafter referred to as "Present compound (Ic)") may be prepared by reacting a compound represented by formula (Ia) (hereinafter referred to as "Present compound (Ia)") with an oxidizing agent.

[wherein the symbols are the same as defined above.]

First, a process for preparing the Present compound (Ib) from the Present compound (Ia) is described.

The reaction is usually carried out in a solvent. Examples of the solvent to be used in the reaction include aliphatic halogenated hydrocarbons such as dichloromethane and chloroform (hereinafter collectively referred to as "aliphatic halogenated hydrocarbons"); nitriles such as acetonitrile (hereinafter collectively referred to as "nitriles"); esters such as ethyl acetate; alcohols such as methanol and ethanol (hereinafter collectively referred to as "alcohols"); acetic acid; water; and mixed solvents thereof.

Examples of the oxidizing agent to be used in the reaction include sodium periodate, m-chloroperbenzoic acid (hereinafter referred to as "mCPBA"), and hydrogen peroxide.

When hydrogen peroxide is used as the oxidizing agent, sodium carbonate or a catalyst may be added to the reaction as needed.

Examples of the catalyst to be used in the reaction include tungstic acid and sodium tungstate.

In the reaction, the oxidizing agent is usually used within a range of 1 to 1.2 molar ratio(s), sodium carbonate is usually used within a range of 0.01 to 1 molar ratio(s), and the catalyst is usually used within a range of 0.01 to 0.5 molar ratios, relative to 1 mole of the Present compound (Ia).

The reaction temperature of the reaction is usually within a range of −20 to 80° C. The reaction period of the reaction is usually within a range of 0.1 to 12 hours.

When the reaction is completed, the reaction mixture is extracted with organic solvent(s), and the organic layers are sequentially washed with an aqueous solution of a reducing agent (for example, sodium sulfite or sodium thiosulfate) and an aqueous solution of a base (for example, sodium hydrogen carbonate) as needed. The resulting organic layers are dried and concentrated to give the Present compound (Ib).

Next, a process for preparing the Present compound (Ic) from the Present compound (Ib) is described.

The reaction is usually carried out in a solvent. Examples of the solvent to be used in the reaction include aliphatic halogenated hydrocarbons, nitriles, alcohols, acetic acid, water, and mixed solvents thereof.

Examples of the oxidizing agent to be used in the reaction include mCPBA and hydrogen peroxide.

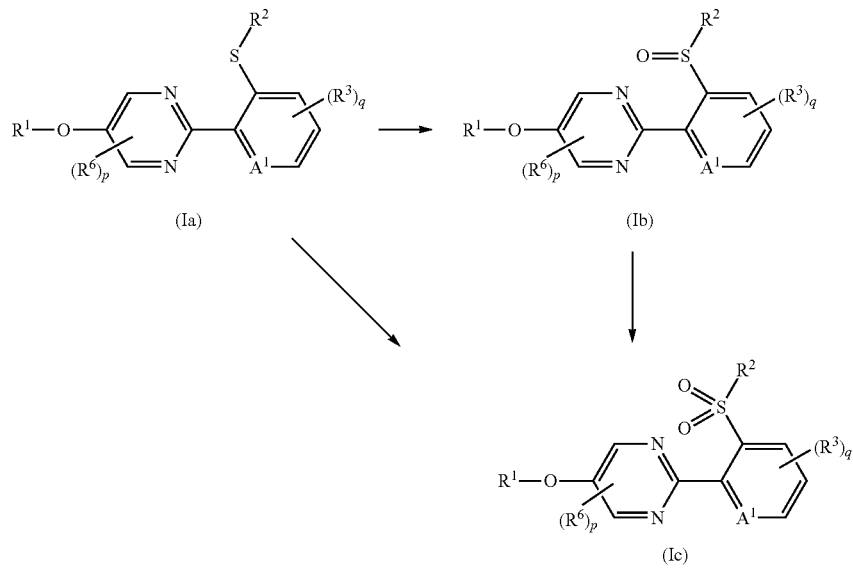

When hydrogen peroxide is used as the oxidizing agent, sodium carbonate or a catalyst may be added to the reaction as needed.

Examples of the catalyst to be used in the reaction include sodium tungstate.

In the reaction, the oxidizing agent is usually used within a range of 1 to 2 molar ratio(s), sodium carbonate is usually used within a range of 0.01 to 1 molar ratio(s), and the catalyst is usually used within a range of 0.01 to 0.5 molar ratios, relative to 1 mole of the Present compound (Ib).

The reaction temperature of the reaction is usually within a range of −20 to 120° C. The reaction period of the reaction is usually within a range of 0.1 to 12 hours.

When the reaction is completed, the reaction mixture is extracted with organic solvent(s), and the organic layers are sequentially washed with an aqueous solution of a reducing agent (for example, sodium sulfite or sodium thiosulfate) and an aqueous solution of a base (for example, sodium hydrogen carbonate) as needed. The organic layers are dried and concentrated to give the Present compound (Ic).

Also, the Present compound (Ic) may be prepared in one step reaction (one-pot) by reacting the Present compound (Ia) with an oxidizing agent.

The reaction may be carried out by using the oxidizing agent usually at 2.0 to 2.4 molar ratios relative to 1 mole of the Present compound (Ia) according to the process for preparing the Present compound (Ic) from the Present compound (Ib).

Process 2

A compound represented by formula (I) (hereinafter referred to as "Present compound (I)") may be prepared by reacting a compound represented by formula (M-3) (hereinafter referred to as "Compound (M-3)") with a compound represented by formula (R-3) (hereinafter referred to as "Compound (R-3)") in the presence of a base.

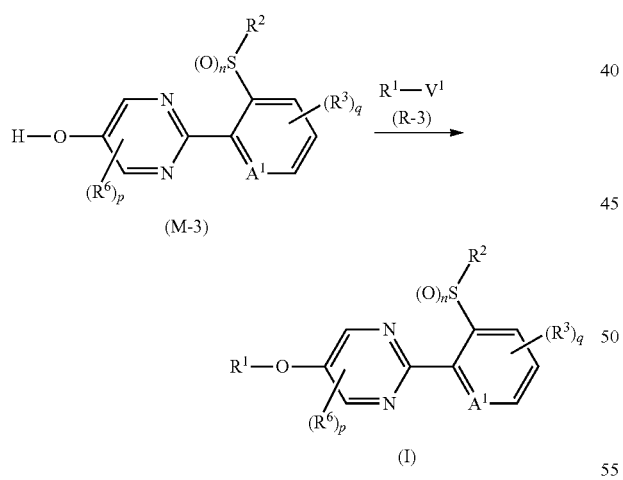

[wherein: $V^1$ represents a chlorine atom, a bromine atom, an iodine atom, a C1-C10 perfluoroalkanesulfonyloxy group, or a tosyloxy group; and the other symbols are the same as defined above.]

The reaction is usually carried out in a solvent. Examples of the solvent to be used in the reaction include ethers such as tetrahydrofuran, ethylene glycol dimethyl ether (hereinafter referred to as "DME"), methyl-tert-butyl ether, and 1,4-dioxane (hereinafter collectively referred to as "ethers"); aliphatic halogenated hydrocarbons; aromatic hydrocarbons such as toluene and xylene (hereinafter collectively referred to as "aromatic hydrocarbons"); aprotic polar solvents such as dimethylformamide (hereinafter referred to as "DMF"), N-methylpyrrolidone (hereinafter referred to as "NMP"), and dimethyl sulfoxide (hereinafter referred to as "DMSO") (hereinafter collectively referred to as "aprotic polar solvents"); and mixed solvents thereof.

Examples of the base to be used in the reaction include organic bases such as triethylamine, diisopropylethylamine, pyridine, and 4-(dimethylamino)pyridine (hereinafter collectively referred to as "organic bases"); alkali metal hydrides such as sodium hydride (hereinafter collectively referred to as "alkali metal hydrides"); and alkali metal carbonates such as sodium carbonate and potassium carbonate (hereinafter collectively referred to as "alkali metal carbonates").

In the reaction, the Compound (R-3) is usually used within a range of 1 to 10 molar ratio(s), and the base is usually used within a range of 0.1 to 5 molar ratios, relative to 1 mole of the Compound (M-3).

The reaction temperature of the reaction is usually within a range of −20° C. to 120° C. The reaction period of the reaction is usually within a range of 0.1 to 24 hours.

When the reaction is completed, the reaction mixture is extracted with organic solvent(s), and the organic layers are worked up (for example, dried or concentrated) to give the Present compound (I).

Process 3

The Present compound (Ia) may be prepared by reacting a compound represented by formula (M-1) (hereinafter referred to as "Compound (M-1)") with a compound represented by formula (R-1) (hereinafter referred to as "Compound (R-1)") in the presence of a base.

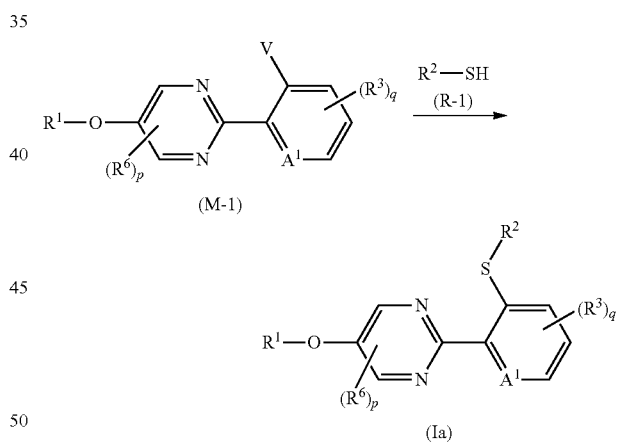

[wherein: V represents a halogen atom; and the other symbols are the same as defined above.]

The reaction is usually carried out in a solvent. Examples of the solvent to be used in the reaction include ethers, aromatic hydrocarbons, nitriles, aprotic polar solvents, and mixed solvents thereof.

Examples of the base to be used in the reaction include alkali metal carbonates and alkali metal hydrides.

In the reaction, the Compound (R-1) is usually used within a range of 1 to 10 molar ratio(s), and the base is usually used within a range of 1 to 10 molar ratio(s), relative to 1 mole of the Compound (M-1).

The reaction temperature of the reaction is usually within a range of −20° C. to 150° C. The reaction period of the reaction is usually within a range of 0.5 to 24 hours.

When the reaction is completed, the reaction mixture is extracted with organic solvent(s), and the organic layers are worked up (for example, dried or concentrated) to give the Present compound (Ia).

In the reaction, V is preferably a fluorine atom.

Process 4

The Present compound (I) may be prepared by reacting a compound represented by formula (M-4) (hereinafter referred to as "Compound (M-4)") with a compound represented by formula (R-15) (hereinafter referred to as "Compound (R-15)") in the presence of a base.

[wherein the symbols are the same as defined above.]

The reaction is usually carried out in a solvent. Examples of the solvent to be used in the reaction include ethers, aromatic hydrocarbons, nitriles, aprotic polar solvents, and mixed solvents thereof.

Examples of the base to be used in the reaction include alkali metal carbonates and alkali metal hydrides.

In the reaction, the Compound (R-4) is usually used within a range of 1 to 10 molar ratio(s), and the base is usually used within a range of 1 to 10 molar ratio(s), relative to 1 mole of the Compound (M-4).

The reaction temperature of the reaction is usually within a range of −20° C. to 150° C. The reaction period of the reaction is usually within a range of 0.5 to 24 hours.

When the reaction is completed, the reaction mixture is extracted with organic solvent(s), and the organic layers are worked up (for example, dried or concentrated) to give the Present compound (I).

V is preferably a fluorine atom or a chlorine atom.

Process 5

A compound represented by formula (Ig) (hereinafter referred to as "Present compound (Ig)") may be prepared according to the following process.

[wherein: $R^{35}$ represents a hydrogen atom, a C1-C6 alkyl group optionally having one or more halogen atoms, a phenyl group optionally having one or more substituents selected from Group D, or a 5 or 6 membered aromatic heterocyclic group optionally having one or more substituents selected from Group D; $R^{37}$ represents a C1-C6 alkyl group; and the other symbols are the same as defined above.]

First, the first step wherein a compound represented by formula (M-7) (hereinafter referred to as "Compound (M-7)") is reacted with a compound represented by formula (R-7) (hereinafter referred to as "Compound (R-7)") is described.

The reaction is usually carried out in a solvent. Examples of the solvent to be used in the reaction include ethers, aliphatic hydrocarbons, aromatic hydrocarbons, aliphatic halogenated hydrocarbons, alcohols, esters, nitriles, aprotic polar solvents, nitrogen-containing aromatic compounds, and mixed solvents thereof.

A base may be added to the reaction as needed, and examples of the base include organic bases.

In the reaction, the Compound (R-7) is usually used within a range of 1 to 10 molar ratio(s), and the base is usually used within a range of 1 to 10 molar ratio(s), relative to 1 mole of the Compound (M-7).

The reaction temperature of the reaction is usually within a range of −50 to 200° C. The reaction period of the reaction is usually within a range of 0.1 to 24 hours.

When the reaction is completed, the reaction mixture is concentrated to obtain residues, and the residues are directly used in the second step, or to the reaction mixture is added water, and then the mixture is extracted with organic solvent(s), and the organic layers are worked up (for example, dried and concentrated) to obtain residues, and the residues are used in the second step.

Next, the second step wherein the residues obtained in the first step is reacted with ammonia to prepare the Present compound (Ig) is described.

The reaction is usually carried out in a solvent. Examples of the solvent to be used in the reaction include ethers, nitriles, alcohols, aprotic polar solvents, nitrogen-containing aromatic compounds, and mixed solvents thereof.

Examples of the ammonia to be used in the reaction include an ammonia aqueous solution and an ammonia methanol solution.

In the reaction, the ammonia is usually used within a range of 1 to 100 molar ratio(s) relative to 1 mole of the Compound (M-7).

The reaction temperature of the reaction is usually within a range of 0 to 100° C. The reaction period of the reaction is usually within a range of 0.1 to 24 hours.

When the reaction is completed, to the reaction mixture is added water, and then the mixture is extracted with organic solvent(s), and the organic layers are worked up (for example, dried or concentrated) to give the Present compound (Ig).

Hereinafter, processes for preparing each Intermediate compound are described.

Reference Process 1

The Compound (M-1) may be prepared by reacting a compound represented by formula (M-8) (hereinafter referred to as "Compound (M-8)") with a compound represented by formula (M-9) (hereinafter referred to as "Compound (M-9)") in the presence of a metal catalyst.

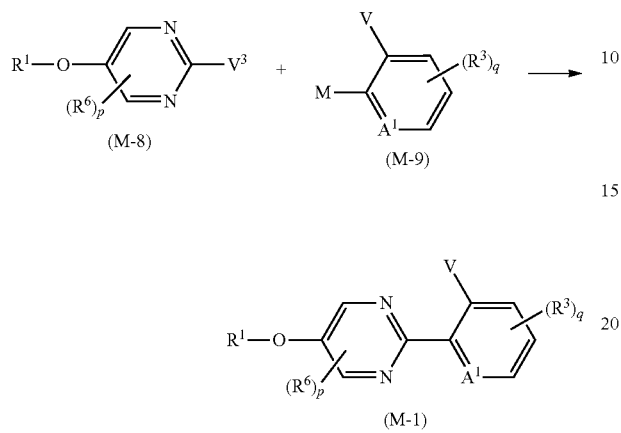

[wherein: $V^3$ represents a chlorine atom, a bromine atom, or an iodine atom; M represents a $B(OR^{40})_2$ or a 4,4,5,5-tetramethyl-1,3,2-dioxaborolan-2-yl group; $R^{40}$ represents a hydrogen atom or a C1-C6 alkyl group; and the other symbols are the same as defined above.]

The Compound (M-9) may be prepared according to, for example, the process described in WO 03/024961 pamphlet, or the process described in Organic Process Research & Development, 2004, 8, 192-200.

The reaction is usually carried out in a solvent. Examples of the solvent to be used in the reaction include ethers, aromatic hydrocarbons, aprotic polar solvents, water, and mixed solvents thereof.

Examples of the metal catalyst to be used in the reaction include palladium catalysts such as tetrakis(triphenylphosphine)palladium(0), 1,1'-bis(diphenylphosphino)ferrocene palladium(II) dichloride, tris(dibenzylideneacetone)dipalladium(0), and palladium(II) acetate; and bis(cyclooctadiene)nickel(0).

A ligand and a base may be added to the reaction as needed.

Examples of the ligand to be used in the reaction include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, and 1,2-bis(diphenylphosphino)ethane.

Examples of the base to be used in the reaction include alkali metal hydrides, alkali metal carbonates, and organic bases.

In the reaction, the Compound (M-9) is usually used within a range of 1 to 10 molar ratio(s), the metal catalyst is usually used within a range of 0.01 to 0.5 molar ratios, the ligand is usually used within a range of 0.01 to 1 molar ratio(s), and the base is usually used within a range of 0.1 to 5 molar ratios, relative to 1 mole of the Compound (M-8).

The reaction temperature of the reaction is usually within a range of −20° C. to 200° C. The reaction period of the reaction is usually within a range of 0.1 to 24 hours.

When the reaction is completed, the reaction mixture is extracted with organic solvent(s), and the organic layers are worked up (for example, dried or concentrated) to give the Compound (M-1).

Reference Process 2

The Compound (M-3) may be prepared by reacting a compound represented by formula (M-11) (hereinafter referred to as "Compound (M-11)") with an acid.

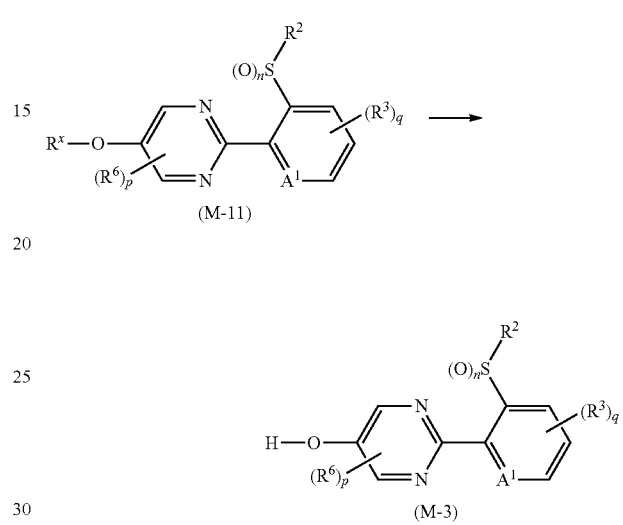

[wherein: $R^x$ represents a methyl group or an ethyl groups; and the other symbols are the same as defined above.]

The reaction is usually carried out in a solvent. Examples of the solvent to be used in the reaction include aliphatic halogenated hydrocarbons, aromatic hydrocarbons, nitriles, alcohols, acetic acid, water, and mixed solvents thereof.

Examples of the acid to be used in the reaction include mineral acids such as hydrochloric acid; halogenated borons such as boron trichloride and boron tribromide; and metal chlorides such as titanium chloride and aluminum chloride.

In the reaction, the acid is usually used within a range of 0.1 to 10 molar ratio(s) relative to 1 mole of the Compound (M-11). When a mineral acid is used as the acid in the reaction, the mineral acid may be used also as a solvent.

The reaction temperature of the reaction is usually within a range of −20° C. to 150° C. The reaction period of the reaction is usually within a range of 0.1 to 24 hours.

When the reaction is completed, the reaction mixture is extracted with organic solvent(s), and the organic layers are worked up (for example, dried or concentrated) to give the Compound (M-3).

Reference Process 3

In the Compound (M-11), a compound wherein n represents 0 (hereinafter referred to as "Compound (M-11a)"), a compound wherein n represents 1 (hereinafter referred to as "Compound (M-11b)"), and a compound wherein n represents 2 (hereinafter referred to as "Compound (M-11c)") may be prepared according to the following process.

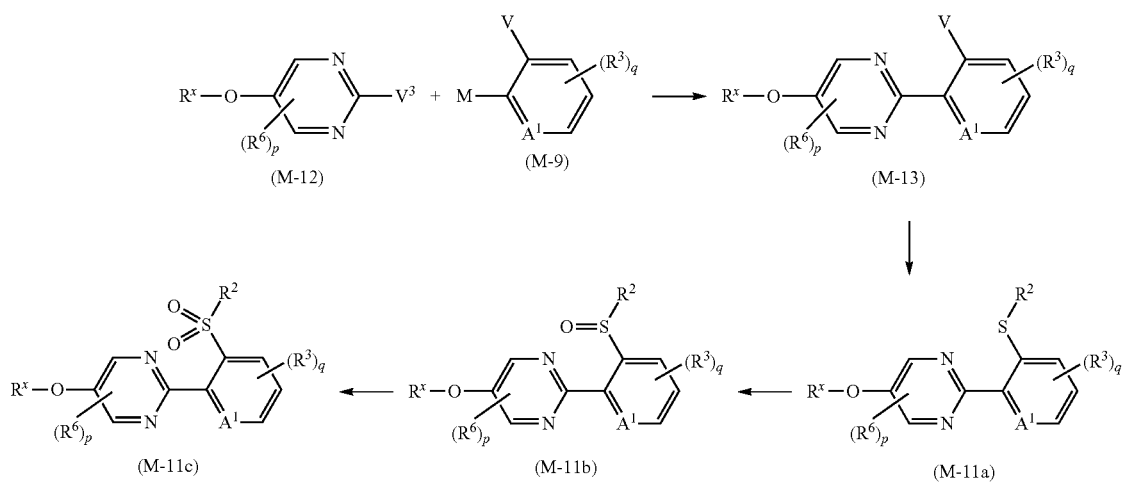

[wherein the symbols are the same as defined above.]

The Compound (M-13) may be prepared by using a compound represented by formula (M-12) (hereinafter referred to as "Compound (M-12)") instead of the Compound (M-8) according to the process described in the Reference process 1.

The Compound (M-12) is a commercially available compound or may be prepared according to a known method.

The Compound (M-11a) may be prepared by using the Compound (M-13) instead of the Compound (M-1) according to the process described in the Process 3.

The Compound (M-11b) and the Compound (M-11c) may be prepared by using the Compound (M-11a) instead of the Present compound (Ia) according to the process described in the Process 1.

Reference Process 4

A compound represented by formula (M-17) (hereinafter referred to as "Compound (M-17)") may be prepared by reacting a compound represented by formula (M-16) (hereinafter referred to as "Compound (M-16)") with the Compound (R-7), followed by with ammonia.

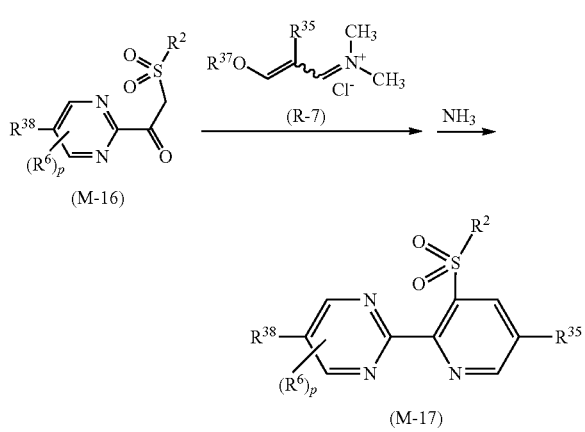

[wherein: $R^{38}$ represents a halogen atom, a $OR^1$, or a $OR^x$; and the other symbols are the same as defined above.]

The reaction may be carried out by using the Compound (M-16) instead of the Compound (M-7) according to the process described in the Process 5.

Reference Process 5

The Compound (M-16) may be prepared by reacting a compound represented by formula (M-15) (hereinafter referred to as "Compound (M-15)") with a compound represented by formula (R-16) (hereinafter referred to as "Compound (R-16)") in the presence of a base.

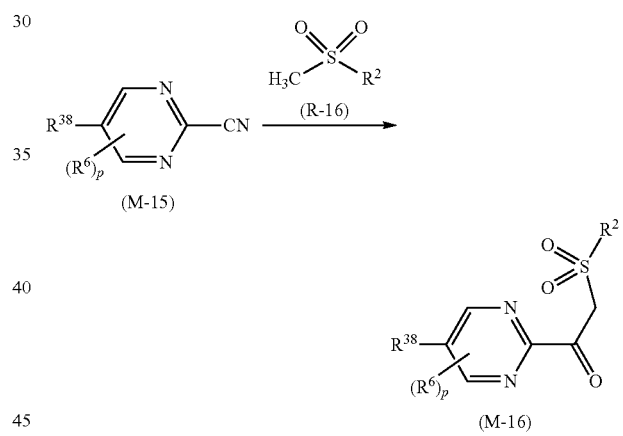

[wherein the symbols are the same as defined above.]

The Compound (M-15) wherein $R^{38}$ represents a halogen atom or a $OR^x$ is a commercially available compound, or may be prepared according to a known method.

The Compound (R-16) is a commercially available compound, or may be prepared according to the process described in Journal of Molecular Catalysis A: Chemical, 2011, 341(1-2), 57-62.

The reaction is usually carried out in a solvent. Examples of the solvent to be used in the reaction include alcohols, ethers, aromatic hydrocarbons, aprotic polar solvents, and mixed solvents thereof.

Examples of the base to be used in the reaction include butyllithium, lithium diisopropylamide, sodium bis(trimethylsilyl)amide, potassium bis(trimethylsilyl)amide, potassium t-butoxide, or alkali metal hydrides.

In the reaction, the Compound (R-16) is usually used within a range of 1 to 5 molar ratio(s), and the base is usually used within a range of 1 to 5 molar ratio(s), relative to 1 mole of the Compound (M-15). Preferably, the Compound (R-16)

is used within a range of 1.0 to 1.1 molar ratio(s), and the base is used within a range of 1 to 2 molar ratio(s), relative to 1 mole of the Compound (M-15).

The reaction temperature of the reaction is usually within a range of −78° C. to 100° C. The reaction period of the reaction is usually within a range of 0.5 to 12 hours.

When the reaction is completed, the reaction mixture is extracted with organic solvent(s), and the organic layers are worked up (for example, dried or concentrated) to give the Compound (M-16).

Reference Process 6

A compound represented by formula (M-18) (hereinafter referred to as "Compound (M-18)") may be prepared by reacting a compound represented by formula (M-19) (hereinafter referred to as "Compound (M-19)") with the Compound (R-4) in the presence of a copper catalyst.

[chemical scheme: (M-19) + $R^1$—OH (R-4) → (M-18)]

[wherein the symbols are the same as defined above.]

The reaction is usually carried out in a solvent. Examples of the solvent to be used in the reaction include ethers, aromatic hydrocarbons, aprotic polar solvents, water, and mixed solvents thereof.

Examples of the copper catalyst to be used in the reaction include copper iodide, copper bromide, and copper chloride.

A ligand and a base may be added to the reaction as needed.

Examples of the ligand to be used in the reaction include 2,2′-bipyridine, 2-aminoethanol, 8-hydroxyquinoline, and 1,10-phenanthroline.

Examples of the base to be used in the reaction include alkali metal hydrides, alkali metal carbonates, and organic bases.

In the reaction, the Compound (R-4) is usually used within a range of 1 to 10 molar ratio(s), the metal catalyst is usually used within a range of 0.01 to 0.5 molar ratios, the ligand is usually used within a range of 0.01 to 1 molar ratio(s), and the base is usually used within a range of 0.1 to 5 molar ratios, relative to 1 mole of the Compound (M-19).

The reaction temperature of the reaction is usually within a range of 0° C. to 200° C. The reaction period of the reaction is usually within a range of 0.1 to 24 hours.

When the reaction is completed, the reaction mixture is extracted with organic solvent(s), and the organic layers are worked up (for example, dried or concentrated) to give the Compound (M-18).

Reference Process 7

A compound represented by formula (M-4a) (hereinafter referred to as "Compound (M-4a)") and a compound represented by formula (M-4b) (hereinafter referred to as "Compound (M-4b)") may be prepared according to the following process.

[chemical schemes: (M-3) → (M-4a) → (M-4b)]

[wherein: $V^4$ represents a chlorine atom or a bromine atom; $V^5$ represents a fluorine atom or an iodine atom; and the other symbols are the same as defined above.]

First, a process for preparing the Compound (M-4a) from the Compound (M-3) is described.

The Compound (M-4a) may be prepared by reacting the Compound (M-3) with phosphorus oxychloride or phosphorus oxybromide.

The reaction is usually carried out in a solvent. Examples of the solvent to be used in the reaction include aromatic hydrocarbons.

When phosphorus oxychloride is used, the phosphorus oxychloride may be used also as a solvent.

In the reaction, the phosphorus oxychloride or the phosphorus oxybromide is usually used within a range of 1 to 10 molar ratio(s) relative to 1 mole of the Compound (M-3).

The reaction temperature of the reaction is usually within a range of 0° C. to 150° C. The reaction period of the reaction is usually within a range of 0.5 to 24 hours.

When the reaction is completed, the reaction mixture is extracted with organic solvent(s), and the organic layers are worked up (for example, dried or concentrated) to give the Compound (M-4a).

Next, a process for preparing the Compound (M-4b) from the Compound (M-4a) is described.

The Compound (M-4b) may be prepared by reacting the Compound (M-4a) with an inorganic fluoride or an inorganic iodide.

The reaction is usually carried out in a solvent. Examples of the solvent to be used in the reaction include nitriles, aprotic polar solvents, nitrogen-containing aromatic compounds, and mixed solvents thereof.

Examples of the inorganic fluoride to be used in the reaction include potassium fluoride, sodium fluoride, and cesium fluoride.

Examples of the inorganic iodide to be used in the reaction include potassium iodide and sodium iodide.

When the Compound (M-4b) wherein $V^5$ represents a fluorine atom is prepared, the inorganic fluoride is usually used within a range of 1 to 10 molar ratio(s) relative to 1 mole of the Compound (M-4a).

When the Compound (M-4b) wherein $V^5$ represents an iodine atom is prepared, the inorganic iodide is usually used within a range of 1 to 10 molar ratio(s) relative to 1 mole of the Compound (M-4a).

The reaction temperature of the reaction is usually within a range of 0° C. to 250° C. The reaction period of the reaction is usually within a range of 0.5 to 24 hours.

When the reaction is completed, the reaction mixture is extracted with organic solvent(s), and the organic layers are worked up (for example, dried or concentrated) to give the Compound (M-4b).

Next, specific examples of the Present compound are shown below.

The Present compound represented by formula (100)

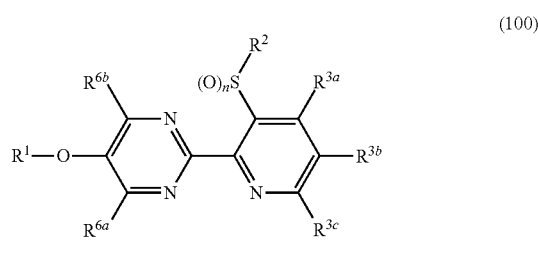

(100)

wherein n represents 2, $R^{3a}$, $R^{3b}$, $R^{3c}$, $R^{6a}$, and $R^{6b}$ represent each a hydrogen atom, and $R^1$ and $R^2$ represent any one combination indicated in Table 1 to Table 5 (hereinafter referred to as "Compound group SX1").

TABLE 1

| $R^1$ | $R^2$ |
|---|---|
| CF$_2$HCH$_2$ | CH$_3$CH$_2$ |
| CH$_3$CF$_2$ | CH$_3$CH$_2$ |
| CF$_3$CH$_2$ | CH$_3$CH$_2$ |
| CCl$_3$CH$_2$ | CH$_3$CH$_2$ |
| CF$_2$HCF$_2$ | CH$_3$CH$_2$ |
| CHClFCF$_2$ | CH$_3$CH$_2$ |
| CF$_3$CH$_2$CH$_2$ | CH$_3$CH$_2$ |
| CF$_2$HCF$_2$CH$_2$ | CH$_3$CH$_2$ |
| CF$_3$CF$_2$CH$_2$ | CH$_3$CH$_2$ |
| CBrF$_2$CF$_2$ | CH$_3$CH$_2$ |
| CF$_3$CFHCF$_2$ | CH$_3$CH$_2$ |
| CH$_3$CF$_2$CH$_2$ | CH$_3$CH$_2$ |
| CF$_3$CH(CH$_3$) | CH$_3$CH$_2$ |
| CF$_3$C(CH$_3$)$_2$ | CH$_3$CH$_2$ |
| CH(CH$_3$)$_2$CH(CF$_3$) | CH$_3$CH$_2$ |
| (CF$_3$)$_2$CH | CH$_3$CH$_2$ |
| CH$_3$CH$_2$CH(CF$_3$) | CH$_3$CH$_2$ |
| CF$_3$CCl$_2$CH$_2$ | CH$_3$CH$_2$ |
| CF$_3$CF$_2$CH(CH$_3$) | CH$_3$CH$_2$ |
| CF$_3$CF$_2$CH(CH$_2$CH$_3$) | CH$_3$CH$_2$ |
| C(CH$_3$)(CF$_3$)$_2$CH$_2$ | CH$_3$CH$_2$ |
| CF$_3$CFHCF$_2$CH$_2$ | CH$_3$CH$_2$ |
| CF$_3$(CF$_2$)$_2$CH$_2$ | CH$_3$CH$_2$ |
| CBrF$_2$CF$_2$CH$_2$CH$_2$ | CH$_3$CH$_2$ |
| CF$_3$CFHCF$_2$CH(CH$_3$) | CH$_3$CH$_2$ |

TABLE 2

| $R^1$ | $R^2$ |
|---|---|
| CF$_3$CH=CHCH$_2$ | CH$_3$CH$_2$ |
| CF$_3$(CF$_2$)$_3$CH$_2$ | CH$_3$CH$_2$ |
| CF$_3$(CF$_2$)$_4$CH$_2$ | CH$_3$CH$_2$ |
| CF$_3$(CF$_2$)$_3$CH$_2$CH$_2$ | CH$_3$CH$_2$ |
| CF(CF$_3$)$_2$CF$_2$CF$_2$CH$_2$CH$_2$ | CH$_3$CH$_2$ |
| CF$_2$H(CF$_2$)$_3$CH$_2$ | CH$_3$CH$_2$ |
| CF$_2$H(CF$_2$)$_5$CH$_2$ | CH$_3$CH$_2$ |
| CF$_3$(CF$_2$)$_3$CH$_2$CH$_2$CH$_2$ | CH$_3$CH$_2$ |
| CF$_3$CF$_2$(CH$_2$)$_5$CH$_2$ | CH$_3$CH$_2$ |
| CF$_3$(CF$_2$)$_5$CH$_2$CH$_2$CH$_2$ | CH$_3$CH$_2$ |
| CF$_3$(CF$_2$)$_3$CH$_2$(CH$_2$)$_4$CH$_2$ | CH$_3$CH$_2$ |
| CF$_3$(CF$_2$)$_5$CH$_2$CH$_2$ | CH$_3$CH$_2$ |
| CF(CF$_3$)$_2$CH$_2$(CH$_2$)$_4$CH$_2$ | CH$_3$CH$_2$ |
| CF$_3$OCFHCF$_2$ | CH$_3$CH$_2$ |
| CH$_3$OCH$_2$CF$_2$CH$_2$ | CH$_3$CH$_2$ |
| CF$_3$CH$_2$OCH$_2$CF$_2$CH$_2$ | CH$_3$CH$_2$ |
| CH$_2$FCF$_2$CH$_2$ | CH$_3$CH$_2$ |
| CH$_2$ClCF$_2$CH$_2$ | CH$_3$CH$_2$ |
| CH$_2$BrCF$_2$CH$_2$ | CH$_3$CH$_2$ |
| CH$_3$OCH$_2$(CF$_2$)$_2$CH$_2$ | CH$_3$CH$_2$ |
| CF$_3$CH$_2$OCH$_2$(CF$_2$)$_2$CH$_2$ | CH$_3$CH$_2$ |
| CH$_2$F(CF$_2$)$_2$CH$_2$ | CH$_3$CH$_2$ |
| CH$_2$Cl(CF$_2$)$_2$CH$_2$ | CH$_3$CH$_2$ |
| CH$_2$Br(CF$_2$)$_2$CH$_2$ | CH$_3$CH$_2$ |
| CH$_3$OCH$_2$(CF$_2$)$_3$CH$_2$ | CH$_3$CH$_2$ |

TABLE 3

| $R^1$ | $R^2$ |
|---|---|
| CF$_3$CH$_2$OCH$_2$(CF$_2$)$_3$CH$_2$ | CH$_3$CH$_2$ |
| CH$_3$OCH$_2$(CF$_2$)$_3$CH$_2$ | CH$_3$CH$_2$ |
| CF$_3$CH$_2$OCH$_2$(CF$_2$)$_3$CH$_2$ | CH$_3$CH$_2$ |
| CH$_2$F(CF$_2$)$_3$CH$_2$ | CH$_3$CH$_2$ |
| CH$_2$Cl(CF$_2$)$_3$CH$_2$ | CH$_3$CH$_2$ |
| CH$_2$Br(CF$_2$)$_3$CH$_2$ | CH$_3$CH$_2$ |
| CH$_3$OCH$_2$(CF$_2$)$_4$CH$_2$ | CH$_3$CH$_2$ |
| CF$_3$CH$_2$OCH$_2$(CF$_2$)$_4$CH$_2$ | CH$_3$CH$_2$ |
| CH$_2$F(CF$_2$)$_4$CH$_2$ | CH$_3$CH$_2$ |
| CH$_2$Cl(CF$_2$)$_4$CH$_2$ | CH$_3$CH$_2$ |
| CH$_2$Br(CF$_2$)$_4$CH$_2$ | CH$_3$CH$_2$ |
| CF$_3$CF$_2$OCFHCF$_2$ | CH$_3$CH$_2$ |
| CF$_3$CF$_2$CF$_2$OCFHCF$_2$ | CH$_3$CH$_2$ |
| CF$_3$CF$_2$CF$_2$OCF(CF$_3$)CH$_2$ | CH$_3$CH$_2$ |
| CF$_3$CH$_2$OCH$_2$CH$_2$ | CH$_3$CH$_2$ |

TABLE 4

| $R^1$ | $R^2$ |
|---|---|
| (fluorinated cyclopropylmethyl structure) | CH$_3$CH$_2$ |
| (CF$_3$-substituted cyclopropylmethyl structure) | CH$_3$CH$_2$ |
| (perfluorocyclohexylmethyl structure) | CH$_3$CH$_2$ |

TABLE 4-continued

| R¹ | R² |
|---|---|
| [cyclobutane with 3F substituents] | CH₃CH₂ |
| [cyclohexane with 2F] | CH₃CH₂ |
| [cyclohexane with F₃C] | CH₃CH₂ |
| [cyclohexane with F₃C meta] | CH₃CH₂ |

TABLE 5

| R¹ | R² |
|---|---|
| CH₃SCH₂CF₂CH₂ | CH₃CH₂ |
| CH₃S(O)CH₂CF₂CH₂ | CH₃CH₂ |
| CH₃S(O)₂CH₂CF₂CH₂ | CH₃CH₂ |
| CF₃CH₂SCH₂CF₂CH₂ | CH₃CH₂ |
| CF₃CH₂S(O)CH₂CF₂CH₂ | CH₃CH₂ |
| CF₃CH₂S(O)₂CH₂CF₂CH₂ | CH₃CH₂ |
| CF₃SCH₂CF₂CH₂ | CH₃CH₂ |
| CF₃S(O)CH₂CF₂CH₂ | CH₃CH₂ |
| CF₃S(O)₂CH₂CF₂CH₂ | CH₃CH₂ |
| CF₃SCH₂(CF₂)₂CH₂ | CH₃CH₂ |
| CF₃S(O)CH₂(CF₂)₂CH₂ | CH₃CH₂ |
| CF₃S(O)₂CH₂(CF₂)₂CH₂ | CH₃CH₂ |
| CF₃SCH₂(CF₂)₃CH₂ | CH₃CH₂ |
| CF₃S(O)CH₂(CF₂)₃CH₂ | CH₃CH₂ |
| CF₃S(O)₂CH₂(CF₂)₃CH₂ | CH₃CH₂ |
| CF₃SCH₂(CF₂)₄CH₂ | CH₃CH₂ |
| CF₃S(O)CH₂(CF₂)₄CH₂ | CH₃CH₂ |
| CF₃S(O)₂CH₂(CF₂)₄CH₂ | CH₃CH₂ |
| CF₃CH₂SCH₂CH₂ | CH₃CH₂ |
| CF₃CH₂S(O)CH₂CH₂ | CH₃CH₂ |
| CF₃CH₂S(O)₂CH₂CH₂ | CH₃CH₂ |
| CF₃SCH₂CH₂ | CH₃CH₂ |
| CF₃S(O)CH₂CH₂ | CH₃CH₂ |
| CF₃S(O)₂CH₂CH₂ | CH₃CH₂ |

The Present compound represented by formula (100), wherein n represents 1, $R^{3a}$, $R^{3b}$, $R^{3c}$, $R^{6a}$, and $R^{6b}$ represent each a hydrogen atom, and $R^2$ and $R^1$ represent any one combination indicated in Table 1 to Table 5 (hereinafter referred to as "Compound group SX2").

The Present compound represented by formula (100), wherein n represents 0, $R^{3a}$, $R^{3b}$, $R^{3c}$, $R^{6a}$, and $R^{6b}$ represent each a hydrogen atom, and $R^1$ and $R^2$ represent any one combination indicated in Table 1 to Table 5 (hereinafter referred to as "Compound group SX3").

The Present compound represented by formula (100), wherein n represents 2, $R^{3a}$, $R^{3c}$, $R^{6a}$, and $R^{6b}$ represent each a hydrogen atom, $R^{3b}$ represents a trifluoromethyl group, and $R^1$ and $R^2$ represent any one combination indicated in Table 1 to Table 5 (hereinafter referred to as "Compound group SX4").

The Present compound represented by formula (100), wherein n represents 1, $R^{3a}$, $R^{3c}$, $R^{6a}$, and $R^{6b}$ represent each a hydrogen atom, $R^{3b}$ represents a trifluoromethyl group, and $R^1$ and $R^2$ represent any one combination indicated in Table 1 to Table 5 (hereinafter referred to as "Compound group SX5").

The Present compound represented by formula (100), wherein n represents 0, $R^{3a}$, $R^{3c}$, $R^{6a}$, and $R^{6b}$ represent each a hydrogen atom, $R^{3b}$ represents a trifluoromethyl group, and $R^1$ and $R^2$ represent any one combination indicated in Table 1 to Table 5 (hereinafter referred to as "Compound group SX6").

The Present compound represented by formula (200)

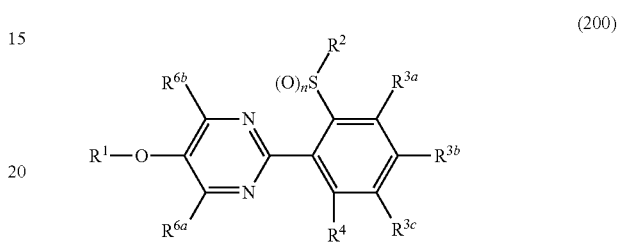

(200)

wherein $R^4$ represents a hydrogen atom, n represents 2, $R^{3a}$, $R^{3b}$, $R^{3c}$, $R^{6a}$, and $R^{6b}$ represent each a hydrogen atom, and $R^1$ and $R^2$ represent any one combination indicated in Table 1 to Table 5 (hereinafter referred to as "Compound group SX7").

The Present compound represented by formula (200), wherein $R^4$ represents a hydrogen atom, n represents 1, $R^{3a}$, $R^{3b}$, $R^{3c}$, $R^{6a}$, and $R^{6b}$ represent each a hydrogen atom, and $R^1$ and $R^2$ represent any one combination indicated in Table 1 to Table 5 (hereinafter referred to as "Compound group SX8").

The Present compound represented by formula (200), wherein $R^4$ represents a hydrogen atom, n represents 0, $R^{3a}$, $R^{3b}$, $R^{3c}$, $R^{6a}$, and $R^{6b}$ represent each a hydrogen atom, and $R^1$ and $R^2$ represent any one combination indicated in Table 1 to Table 5 (hereinafter referred to as "Compound group SX9").

The Present compound represented by formula (200), wherein $R^4$ represents a hydrogen atom, n represents 2, $R^{3a}$, $R^{3c}$, $R^{6a}$, and $R^{6b}$ represent each a hydrogen atom, $R^{3b}$ represents a trifluoromethyl group, and $R^1$ and $R^2$ represent any one combination indicated in Table 1 to Table 5 (hereinafter referred to as "Compound group SX10").

The Present compound represented by formula (200), wherein $R^4$ represents a hydrogen atom, n represents 1, $R^{3a}$, $R^{3c}$, $R^{6a}$, and $R^{6b}$ represent each a hydrogen atom, $R^{3b}$ represents a trifluoromethyl group, and $R^1$ and $R^2$ represent any one combination indicated in Table 1 to Table 5 (hereinafter referred to as "Compound group SX11").

The Present compound represented by formula (200), wherein $R^4$ represents a hydrogen atom, n represents 0, $R^{3a}$, $R^{3c}$, $R^{6a}$, and $R^{6b}$ represent each a hydrogen atom, $R^{3b}$ represents a trifluoromethyl group, and $R^1$ and $R^2$ represent any one combination indicated in Table 1 to Table 5 (hereinafter referred to as "Compound group SX12").

The Present compound represented by formula (200), wherein $R^4$ represents a fluorine atom, n represents 2, $R^{3a}$, $R^{3b}$, $R^{3c}$, $R^{6a}$, and $R^{6b}$ represent each a hydrogen atom, and $R^1$ and $R^2$ represent any one combination indicated in Table 1 to Table 5 (hereinafter referred to as "Compound group SX13").

The Present compound represented by formula (200), wherein $R^4$ represents a fluorine atom, n represents 1, $R^{3a}$, $R^{3b}$, $R^{3c}$, $R^{6a}$, and $R^{6b}$ represent each a hydrogen atom, and $R^1$ and $R^2$ represent any one combination indicated in Table 1 to Table 5 (hereinafter referred to as "Compound group SX14").

The Present compound represented by formula (200), wherein $R^4$ represents a fluorine atom, n represents 0, $R^{3a}$, $R^{3b}$, $R^{3c}$, $R^{6a}$, and $R^{6b}$ represent each a hydrogen atom, and $R^1$ and $R^2$ represent any one combination indicated in Table 1 to Table 5 (hereinafter referred to as "Compound group SX15").

The Present compound represented by formula (200), wherein $R^4$ represents a fluorine atom, n represents 2, $R^3$, $R^{3c}$, $R^{6a}$, and $R^{6b}$ represent each a hydrogen atom, $R^{3b}$ represents a trifluoromethyl group, and $R^1$ and $R^2$ represent any one combination indicated in Table 1 to Table 5 (hereinafter referred to as "Compound group SX16").

The Present compound represented by formula (200), wherein $R^4$ represents a fluorine atom, n represents 1, $R^{3a}$, $R^{3c}$, $R^{6a}$, and $R^{6b}$ represent each a hydrogen atom, $R^{3b}$ represents a trifluoromethyl group, and $R^1$ and $R^2$ represent any one combination indicated in Table 1 to Table 5 (hereinafter referred to as "Compound group SX17").

The Present compound represented by formula (200), wherein $R^4$ represents a fluorine atom, n represents 0, $R^{3a}$, $R^{3c}$, $R^{6a}$, and $R^{6b}$ represent each a hydrogen atom, $R^{3b}$ represents a trifluoromethyl group, and $R^1$ and $R^2$ represent any one combination indicated in Table 1 to Table 5 (hereinafter referred to as "Compound group SX18").

The Present compound may be mixed with or used in combination with one or more ingredients selected from the group consisting of the following Group (a), Group (b), Group (c), and Group (d) (hereinafter referred to as "Present ingredient").

Group (a) is a group of pesticides, miticides, and nematicides consisting of the following Subgroup a-1 to Subgroup a-10.
Subgroup a-1: Carbamate acetylcholinesterase (AChE) inhibitors
Subgroup a-2: Organophosphorus acetylcholinesterase (AChE) inhibitors
Subgroup a-3: GABAergic chloride channel blockers
Subgroup a-4: GABAergic chloride channel allosteric modulators
Subgroup a-5: Sodium channel modulators
Subgroup a-6: Nicotinic acetylcholine receptor (nAChR) competitive modulators
Subgroup a-7: Ryanodine receptor modulators
Subgroup a-8: Microbial materials
Subgroup a-9: Nematicidal active compounds
Subgroup a-10: Other pesticides and miticides
Group (b) is a group of fungicides consisting of the following Subgroup b-1 to Subgroup b-18.
Subgroup b-1: PA fungicides (Phenylamides)
Subgroup b-2: MBC fungicides (Methyl benzimidazole carbamates)
Subgroup b-3: Thiazole carboxamides
Subgroup b-4: SDHI (Succinate dehydrogenase inhibitors)
Subgroup b-5: QoI fungicides (Qo inhibitors)
Subgroup b-6: QiI fungicides (Qi inhibitors)
Subgroup b-7: Thiophenecarboxamides
Subgroup b-8: AP fungicides (Anilinopyrimidines)
Subgroup b-9: PP fungicides (Phenylpyrroles)
Subgroup b-10: AH fungicides (Aromatic hydrocarbons)
Subgroup b-11: DMI-fungicides (Demethylation inhibitors)
Subgroup b-12: CCA fungicides (Carboxylic acid amides)
Subgroup b-13: Piperidinyl thiazole isoxazolines
Subgroup b-14: Tetrazolyl oximes
Subgroup b-15: Dithiocarbamates
Subgroup b-16: Phthalimides
Subgroup b-17: Microbial fungicides
Subgroup b-18: Other fungicides Group (c) is a group of plant growth regulators consisting of the following Subgroup c-1, Subgroup c-2, and Subgroup c-3.
Subgroup c-1: Plant growth regulating compounds
Subgroup c-2: Mycorrhizal fungi
Subgroup c-3: Root nodule bacteria
Group (d) is a group of Phytotoxicity-reducing agents.

Hereinafter, examples of the combination of the Present ingredient and the Present compound are described. For example, alanycarb+SX indicates a combination of alanycarb and SX.

The abbreviation of "SX" indicates "any one of the Present compound selected from the Compound groups SX1 to SX176". Also, all of the following Present ingredients are known ingredients, and obtainable from a commercially available formulation, or may be prepared by a known method. When the Present ingredient is a microorganism, it may be available from a bacterial authority depository. Further, the number in parentheses represents the CAS registration number.

Combinations of the Present ingredient in the above Subgroup a-1 and the Present compound:
alanycarb+SX, aldicarb+SX, bendiocarb+SX, benfuracarb+SX, butocarboxim+SX, butoxycarboxim+SX, carbaryl (NAC)+SX, carbofuran+SX, carbosulfan+SX, ethiofencarb+SX, fenobucarb (BPMC)+SX, formetanate+SX, furathiocarb+SX, isoprocarb (MIPC)+SX, methiocarb+SX, methomyl+SX, metolcarb+SX, oxamyl+SX, pirimicarb+SX, propoxur (PHC)+SX, thiodicarb+SX, thiofanox+SX, triazamate+SX, trimethacarb+SX, XMC+SX, xylylcarb+SX.

Combinations of the Present ingredient in the above Subgroup a-2 and the Present compound:
acephate+SX, azamethiphos+SX, azinphos-ethyi+SX, azinphos-methyl+SX, cadusafos+SX, chlorethoxyfos+SX, chlorfenvinphos+SX, chlormephos+SX, chlorpyrifos+SX, chlorpyrifos-methyl+SX, coumaphos+SX, cyanophos (CYAP)+SX, demeton-S-methyl+SX, diazinon+SX, dichlorvos (DDVP)+SX, dicrotophos+SX, dimethoate+SX, dimethylvinphos+SX, disulfoton+SX, EPN+SX, ethion+SX, ethoprophos+SX, famphur+SX, fenamiphos+SX, fenitrothion (MEP)+SX, fenthion (MPP)+SX, fosthiazate+SX, heptenophos+SX, imicyafos+SX, isofenphos+SX, isopropyl-O-(methoxyaminothiophosphoryl)salicylate+SX, isoxathion+SX, malathion+SX, mecarbam+SX, methamidophos+SX, methidathion (DMTP)+SX, mevinphos+SX, monocrotophos+SX, naled (BRP)+SX, omethoate+SX, oxydemeton-methyl+SX, parathion+SX, parathion-methyl+SX, phenthoate (PAP)+SX, phorate+SX, phosalone+SX, phosmet (PMP)+SX, phosphamidon+SX, phoxim+SX, pirimiphos-methyl+SX, profenofos+SX, propetamphos+SX, prothiofos+SX, pyraclofos+SX, pyridaphenthion+SX, quinalphos+SX, sulfotep+SX, tebupirimfos+SX, temephos+SX, terbufos+SX, tetrachlorvinphos+SX, thiometon+SX, triazophos+SX, trichlorfon (DEP)+SX, vamidothion+SX.

Combinations of the Present ingredient in the above Subgroup a-3 and the Present compound:
ethiprole+SX, fipronil+SX, flufiprole+SX, chlordane+SX, endosulfan+SX, alpha-endosulfan+SX.

Combinations of the Present ingredient in the above Subgroup a-4 and the Present compound:
afoxolaner+SX, fluralaner+SX, broflanilide+SX, fluxametamide+SX.

Combinations of the Present ingredient in the above Subgroup a-5 and the Present compound:

acrinathrin+SX, allethrin+SX, bifenthrin+SX, kappa-bifenthrin+SX, bioallethrin+SX, bioresmethrin+SX, cycloprothrin+SX, cyfluthrin+SX, beta-cyfluthrin+SX, cyhalothrin 4 SX, gamma-cyhalothrin+SX, lambda-cyhalothrin+SX, cypermethrin+SX, alpha-cypermethrin+SX, beta-cypermethrin+SX, theta-cypermethrin+SX, zeta-cypermethrin+SX, cyphenothrin+SX, deltamethrin+SX, empenthrin+SX, esfenvalerate+SX, etofenprox+SX, fenpropathrin+SX, fenvalerate+SX, flucythrinate+SX, flumethrin+SX, fluvalinate+SX, tau-fluvalinate+SX, halfenprox+SX, heptafluthrin+SX, imiprothrin+SX, kadethrin+SX, meperfluthrin+SX, momfluorothrin+SX, permethrin+SX, phenothrin+SX, prallethrin+SX, pyrethrins+SX, resmethrin+SX, silafluofen+SX, tefluthrin+SX, kappa-tefluthrin+SX, tetramethrin+SX, tetramethylfluthrin+SX, tralomethrin+SX, transfluthrin+SX, benfluthrin+SX, flufenoprox+SX, flumethrin+SX, sigma-cypermethrin+SX, furamethrin+SX, metofluthrin+SX, profluthrin+SX, dimefluthrin+SX, epsilon-metofluthrin+SX, epsilon-momfluorothrin+SX, methoxychlor+SX.

Combinations of the Present ingredient in the above Subgroup a-6 and the Present compound:

acetamiprid+SX, clothianidin+SX, dinotefuran+SX, imidacloprid+SX, nitenpyram+SX, thiacloprid+SX, thiamethoxam+SX, sulfoxaflor+SX, flupyradifurone+SX, triflumezopyrim+SX, dicloromezotiaz+SX, cycloxaprid+SX, (E)-N-{1-[(6-chloropyridin-3-yl)methyl]pyridin-2(1H)-ylidene}-2,2,2-trifluoroacetamide (1363400-41-2)+SX.

Combinations of the Present ingredient in the above Subgroup a-7 and the Present compound:

chlorantraniliprole+SX, cyantraniliprole+SX, cycloniliprole+SX, flubendiamide+SX, tetraniliprole+SX, cyhalodiamide+SX, a compound represented by the following formula

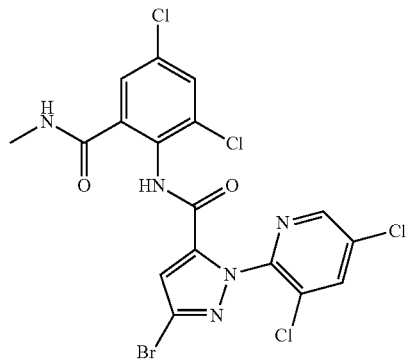 [SMILES: CNC(=O)c1cc(Cl)cc(Cl)c1NC(=O)c1cc(Br)nn1-c1ncc(Cl)cc1Cl]

(1104384-14-6)+SX.

Combinations of the Present ingredient in the above Subgroup a-8 and the Present compound:

*Beauveria bassiana*+SX, *Beauveria brongniartii*+SX, *Paecilomyces fumosoroseus*+SX, *Paecilomyces lilacinus*+SX, *Paecilomyces tenuipes*+SX, *Verticillium lecani*+SX, *Arthrobotrys dactyloides*+SX, *Bacillus thuringiensis*+SX, *Bacillus firmus*+SX, *Bacillus megaterium*+SX, *Hirsutella rhossiliensis*+SX, *Hirsutella minnesotensis*+SX, *Monacrosporium phymatopagus*+SX, *Pasteuria nishizawae*+SX, *Pasteuria penetrans*+SX, *Pasteuria usgae*+SX, *Verticillium chlamydosporium*+SX.

Combinations of the Present ingredient in the above Subgroup a-9 and the Present compound:

abamectin+SX, fluazaindolizine+SX, fluensulfone+SX, fluopyram+SX, tioxazafen+SX.

Combinations of the Present ingredient in the above Subgroup a-10 and the Present compound:

spinetoram+SX, spinosad+SX, emamectin-benzoate+SX, lepimectin+SX, milbemectin+SX, hydroprene+SX, kinoprene+SX, methoprene+SX, fenoxycarb+SX, pyriproxyfen+SX, methyl bromide+SX, chloropicrin+SX, sulfuryl fluoride+SX, sodium aluminium fluoride or chiolite+SX, borax+SX, boric acid+SX, disodium octaborate+SX, sodium borate+SX, sodium metaborate+SX, tartar emetic+SX, dazomet+SX, metam+SX, pymetrozine+SX, pyrifluquinazone+SX, clofentezine+SX, hexythiazox+SX, diflovidazin+SX, etoxazole+SX, diafenthiuron+SX, azocyclotin+SX, cyhexatin+SX, fenbutatin oxide+SX, propargite+SX, tetradifon+SX, chlorfenapyr+SX, DNOC+SX, sulfluramid+SX, bensultap+SX, cartap+SX, cartap hydrochloride+SX, thiocyclam+SX, thiosultap-disodium+SX, thiosultap-monosodium+SX, bistrifluron+SX, chlorfluazuron+SX, diflubenzuron+SX, fluazuron+SX, flucycloxuron+SX, flufenoxuron+SX, hexaflumuron+SX, lufenuron+SX, novaluron+SX, noviflumuron+SX, teflubenzuron+SX, triflumuron+SX, buprofezin+SX, cyromazine+SX, chromafenozide+SX, halofenozide+SX, methoxyfenozide+SX, tebufenozide+SX, amitraz+SX, hydramethylnon+SX, acequinocyl+SX, fluacrypyrim+SX, bifenazate+SX, fenazaquin+SX, fenpyroximate+SX, pyridaben+SX, pyrimidifen+SX, tebufenpyrad+SX, tolfenpyrad+SX, rotenone+SX, indoxacarb+SX, metaflumizone+SX, spirodiclofen+SX, spiromesifen+SX, spirotetramat+SX, aluminium phosphide+SX, calcium phosphide+SX, phosphine+SX, zinc phosphide+SX, calcium cyanide+SX, potassium cyanide+SX, sodium cyanide+SX, cyenopyrafen+SX, cyflumetofen+SX, pyflubumide+SX, flonicamid+SX, azadirachtin+SX, benzoximate+SX, bromopropylate+SX, chinomethionat+SX, dicofol+SX, pyridalyl+SX, lime sulfur+SX, sulfur+SX, machine oil+SX, nicotine+SX, nicotine-sulfate+SX, afidopyropen+SX, flometoquin+SX, metoxadiazone+SX, pyriminostrobin+SX, N-[3-chloro-1-(pyridin-3-yl)-1H-pyrazol-4-yl]-N-ethyl-3-(3,3,3-trifluoropropylsulfanyl)propaneamide (1477919-27-9)+SX, N-[3-chloro-1-(pyridin-3-yl)-1H-pyrazol-4-yl]-N-ethyl-3-(3,3,3-trifluoropropanesulfinyl)propaneamide (1477919-27-9)+SX, 5-(1,3-dioxan-2-yl)-4-[4-(trifluoromethyl)benzyloxy]pyrimidine (1449021-97-9)+SX.

Combinations of the Present ingredient in the above Subgroup b-1 and the Present compound:

benalaxyl+SX, benalaxyl-M+SX, furalaxyl+SX, metalaxyl+SX, metalaxyl-M+SX, oxadixyl+SX, ofurace+SX.

Combinations of the Present ingredient in the above Subgroup b-2 and the Present compound:

benomyl+SX, carbendazim+SX, fuberidazole+SX, thiabendazole+SX, thiophanate+SX, thiophanate-methyl+SX.

Combinations of the Present ingredient in the above Subgroup b-3 and the Present compound:

ethaboxam+SX.

Combinations of the Present ingredient in the above Subgroup b-4 and the Present compound:

benodanil+SX, flutolanil+SX, mepronil+SX, isofetamid+SX, fenfuram+SX, carboxin+SX, oxycarboxin+SX, thifluzamide+SX, benzovindiflupyr+SX, bixafen+SX, fluxapyroxad+SX, furametpyr+SX, isopyrazam+SX, penflufen+SX, penthiopyrad+SX, sedaxane+SX, pydiflumetofen+SX, boscalid+SX, pyraziflumid+SX, 3-difluoromethyl-N-methoxy-1-methyl-N-[(1R)-1-methyl-2-(2,4,6-trichlorophenyl)ethyl]pyrazole-4-carboxamide (1639015-48-7)+SX, 3-difluoromethyl-N-methoxy-1-methyl-N-[(1S)-1-methyl- 2-(2,4,6-trichlorophenyl)ethyl]pyrazole-4-carboxamide (1639015-49-8)+SX, N-cyclopropyl-3-(difluoromethyl)-5-fluoro-N-(5-chloro-2-isopropylbenzyl)-1-methyl-1H-pyrazole-4-carboxamide (1255734-28-1)+SX, 3-difluoromethyl-1-methyl-N-(1,1,3-trimethylindan-4-yl)pyrazole-4-carboxamide (141573-94-6)+SX, 3-difluoromethyl-1-methyl-N-[(3R)-1,1,3-trimethylindan-4-yl]pyrazole-4-carboxamide (1352994-67-2)+SX, 3-difluoromethyl-N-(7-fluoro-1,1,3-trimethylindan-4-yl)-1-methylpyrazole-4-carboxamide (1383809-87-7)+SX, 3-difluoromethyl-N-[(3R)-7-fluoro-1,1,3-trimethylindan-4-yl]-1-methylpyrazole-4-carboxamide (1513466-73-3)+SX.

Combinations of the Present ingredient in the above Subgroup b-5 and the Present compound:

azoxystrobin+SX, coumoxystrobin+SX, enoxastrobin+SX, flufenoxystrobin+SX, picoxystrobin+SX, pyraoxystrobin+SX, mandestrobin+SX, pyraclostrobin+SX, pyrametostrobin+SX, triclopyricarb+SX, kresoxim-methyl+SX, trifloxystrobin+SX, dimoxystrobin+SX, fenaminstrobin+SX, metominostrobin+SX, orysastrobin+SX, famoxadone+SX, fluoxastrobin+SX, fenamidone+SX, pyribencarb+SX.

Combinations of the Present ingredient in the above Subgroup b-6 and the Present compound:

cyazofamid+SX, amisulbrom+SX, binapacryl+SX, meptyldinocap+SX, dinocap+SX, fluazinam+SX.

Combinations of the Present ingredient in the above Subgroup b-7 and the Present compound:

silthiofam+SX.

Combinations of the Present ingredient in the above Subgroup b-8 and the Present compound:

cyprodinil+SX, mepanipyrim+SX, pyrimethanil+SX.

Combinations of the Present ingredient in the above Subgroup b-9 and the Present compound:

fenpiclonil+SX, fludioxonil+SX.

Combinations of the Present ingredient in the above Subgroup b-10 and the Present compound:

biphenyl+SX, chloroneb+SX, dicloran+SX, quintozene+SX, tecnazene+SX, tolclofos-methyl+SX.

Combinations of the Present ingredient in the above Subgroup b-11 and the Present compound:

azaconazole+SX, bitertanol+SX, bromuconazole+SX, cyproconazole+SX, difenoconazole+SX, diniconazole+SX, diniconazole-M+SX, epoxiconazole+SX, etaconazole+SX, fenbuconazole+SX, fluquinconazole+SX, flusilazole+SX, flutriafol+SX, hexaconazole+SX, imibenconazole+SX, ipconazole+SX, ipfentrifluconazole+SX, mefentrifluconazole+SX, metconazole+SX, myclobutanil+SX, penconazole+SX, propiconazole+SX, simeconazole+SX, tebuconazole+SX, tetraconazole+SX, triadimefon+SX, triadimenol+SX, triticonazole+SX, prothioconazole+SX, triforine+SX, pyrifenox+SX, pyrisoxazole+SX, fenarimol+SX, nuarimol+SX, imazalil+SX, oxpoconazole+SX, oxpoconazole fumarate+SX, pefurazoate+SX, prochloraz+SX, triflumizole+SX.

Combinations of the Present ingredient in the above Subgroup b-12 and the Present compound:

dimethomorph+SX, flumorph+SX, pyrimorph+SX, benthiavalicarb+SX, benthivalicarb-isopropyl+SX, iprovalicarb+SX, valifenalate+SX, mandipropamid+SX.

Combinations of the Present ingredient in the above Subgroup b-13 and the Present compound: oxathiapiprolin+SX.

Combinations of the Present ingredient in the above Subgroup b-14 and the Present compound:

picarbutrazox+SX.

Combinations of the Present ingredient in the above Subgroup b-15 and the Present compound:

ferbam+SX, mancozeb+SX, maneb+SX, metiram+SX, propineb+SX, thiram+SX, zineb+SX, ziram+SX.

Combinations of the Present ingredient in the above Subgroup b-16 and the Present compound:

captan+SX, captafol+SX, folpet+SX.

Combinations of the Present ingredient in the above Subgroup b-17 and the Present compound:

*Agrobacterium radiobactor* (such as strain 84)+SX, *Bacillus amyloliquefaciens*+SX, *Bacillus amyloliquefaciens* strain QST713+SX, *Bacillus amyloliquefaciens* strain FZB24+SX, *Bacillus amyloliquefaciens* strain MBI600+SX, *Bacillus amyloliquefaciens* strain D747+SX, *Bacillus amyloliquefaciens* strain AT332+SX, *Bacillus amyloliquefaciens* strain PTA4838+SX, *Bacillus pumilus*+SX, *Bacillus simplex* (such as strain CGF2856)+SX, *Bacillus subtilis*+SX, *Bacillus subtilis* strain QST713+SX, *Bacillus subtilis* strain HAI0404+SX, *Bacillus subtilis* strain Y1336+SX, *Variovorax paradoxus* (such as strain CGF4526)+SX, *Erwinia carotovora* (such as strain CGE234M403)+SX, *Pseudomonas fluorescens* (such as strain G7090)+SX, *Talaromyces flavus* (such as strain SAY-Y-94-01)+SX, *Trichoderma atroviride* (such as strain SKT-1)+SX, *Trichoderma harzianum*+SX, Harpin protein+SX.

Combinations of the Present ingredient in the above Subgroup b-18 and the Present compound:

bupirimate+SX, dimethirimol+SX, ethirimol+SX, hymexazole+SX, octhilinone+SX, oxolinic acid+SX, diethofencarb+SX, zoxamide+SX, pencycuron+SX, fluopicolide+SX, phenamacril+SX, diflumetorim+SX, tolfenpyrad+SX, fentin acetate+SX, fentin chloride+SX, fentin hydroxide+SX, ametoctradin+SX, blasticidin-S+SX, kasugamycin+SX, streptomycin+SX, oxytetracycline+SX, quinoxyfen+SX, proquinazid+SX, chlozolinate+SX, dimethachlone+SX, iprodione+SX, procymidone+SX, vinciozolin+SX, edifenphos+SX, iprobenfos+SX, pyrazophos+SX, isoprothiolane+SX, etridiazole+SX, iodocarb+SX, propamocarb+SX, prothiocarb+SX, aldimorph+SX, dodemorph+SX, fenpropidin+SX, fenpropimorph+SX, pipералin+SX, spiroxamine+SX, tridemorph+SX, fenhexamid+SX, fenpyrazamine+SX, pyributicarb+SX, naftifine+SX, terbinafine+SX, polyoxins+SX, phthalide+SX, pyroquilon+SX, tricyclazole+SX, carpropamid+SX, diclocymet+SX, fenoxanil+SX, tolprocarb+SX, acibenzolar-S-methyl+SX, probenazole+SX, tiadinil+SX, isotianil+SX, laminarin+SX, cymoxanil+SX, fosetyl+SX, teclofthalam+SX, triazoxide+SX, flusulfamide+SX, diclomezine+SX, methasulfocarb+SX, cyflufenamid+SX, metrafenone+SX, pyriofenone+SX, dodine+SX, flutianil+SX, ferimzone+SX, tebufloquin+SX, validamycin+SX, basic copper chloride+SX, copper(II) hydroxide+SX, basic copper sulfate+SX, Dodecylbenzenesulphonic acid bisethylenediamine copper [II] salt (DBEDC)+SX, organic copper+SX, sulfur+SX, chlorothalonil+SX, dichlofluanid+SX, tolylfluanid+SX, guazatine+SX, iminoctadine+SX, anilazine+SX, dithianon+SX, chinomethionat+SX, fluoroimide+SX, dipymetitrone+SX, quinofumelin+SX, dichlobentiazox+SX, 3-chloro-5-phenyl-6-methyl-4-(2,6-difluorophenyl)pyridazine (1358061-55-8)+SX, fenpicoxamid+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo-4-fluorophenyl)-N-(2-chloro-6-fluorophenyl)-1,3-dimethyl-1H-pyrazol-5-amine (1362477-26-6)+SX, 2,2-dimethyl-9-fluoro-5-(quinolin-3-yl)-2,3-dihydrobenzo[f][1,4]oxazepine (1207749-50-5)+SX, 2-[6-

(3-fluoro-4-methoxyphenyl)-5-methylpyridin-2-yl]quinazoline (1257056-97-5)+SX, 5-fluoro-2-[(4-methylphenyl)methoxy]-4-pyrimidinamine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 1-[2-({[1-(4-chlorophenyl)-1H-pyrazol-3-yl]oxy}methyl)-3-methylphenyl]-4-methyl-5-oxo-4,5-dihydro-1H-tetrazole (1472649-01-6)+SX.

Combinations of the Present ingredient in the above Subgroup c-1 and the Present compound:

ethephon+SX, chlormequat+SX, chlormequat-chloride+SX, mepiquat+SX, mepiquat-chloride+SX, Gibberellin A3+SX, abscisic acid+SX, Kinetin+SX, benzyladenine+SX, forchlorfenuron+SX, thidiazuron+SX.

Combinations of the Present ingredient in the above Subgroup c-2 and the Present compound:

*Glomus* spp.+SX, *Glomus intraradices*+SX, *Glomus mosseae*+SX, *Glomus aggregatum*+SX, *Glomus etunicatum*+SX.

Combinations of the Present ingredient in the above Subgroup c-3 and the Present compound:

*Bradyrhizobium elkani*+SX, *Bradyrhizobium japonicum*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*+SX, *Rhizobium* spp.+SX.

Combinations of the Present ingredient in the above Group (d) and the Present compound:

benoxacor+SX, cloquintocet-mexyl+SX, cyometrinil+SX, dichlormid+SX, fenchlorazole-ethyl+SX, fenclorim+SX, flurazole+SX, furilazole+SX, mefenpyr-diethyl+SX, MG191 (2-(dichloromethyl)-2-methyl-1,3-dioxolane)+SX, oxabetrinil+SX, allidochlor+SX, isoxadifen-ethyl+SX, cyprosulfamide+SX, fluxofenim+SX, 1,8-naphthalic anhydride+SX, AD-67 (4-(dichloroacetyl)-1-oxa-4-azaspiro[4.5]decane)+SX.

Examples of the harmful arthropod on which the Present compound has efficacies include harmful insects and harmful mites. Specific examples of the harmful arthropod include the followings.

Hemiptera Pests:

Delphacidae (for example, *Laodelphax striatellus, Nilaparvata lugens, Sogatella furcifera*, or *Peregrinus maidis*);

Cicadellidae (for example, *Nephotettix cincticeps, Nephotettix virescens, Nephotettix nigropictus* (Rice green leafhopper), *Recilia dorsalis, Empoasca onukii, Empoasca fabae, Dalbulus maidis, Mahanarva posticata* (Sugarcane froghopper), *Mahanarva fimbriolota* (Sugarcane root spittlebug), *Cofana spectra, Nephotettix nigropictus*, or *Recilia dorsalis*);

Aphididae (for example, *Aphis gossypii* (cotton aphid), *Myzus persicae, Brevicoryne brassicae, Aphis spiraecola, Macrosiphum euphorbiae, Aulacorthum solani, Rhopalosiphum padi, Toxoptera citricidus, Hyalopterus pruni, Aphis glycines Matsumura, Rhopalosiphum maidis, Tetraneura nigriabdominalis, Viteus vitifoliae, Daktulosphaira vitifoliae* (Grape *Phylloxera*), *Phylloxera devastatrix Pergande* (Pecan *phylloxera*), *Phylloxera notabilis pergande* (Pecan leaf *phylloxera*), or *Phylloxera russellae Stoetzel* (Southern pecan leaf *phylloxera*));

Pentatomidae (for example, *Scotinophara lurida, Scotinophara coarctata* (Malayan rice black bug), *Nezara antennata, Eysarcoris parvus, Halyomorpha mista, Nezara viridula, Euschistus heros* (Brown stink bug), *Nezara viridula* (Southern green stink bug), *Piezodorus guildinii* (Red banded stink bug), *Scaptocoris castanea* (Burrower brown bug), *Oebalus pugnax*, or *Dichelops melacanthus*);

Alydidae (for example, *Riptortus clavetus, Leptocorisa chinensis, Leptocorisa acuta*, or *Leptocorisa* spp.);

Miridae (for example, *Trigonotylus caelestialium, Stenotus rubrovittatus, Lygus lineolaris*, or *Blissus leucopterus leucopterus* (Chinchi bug));

Aleyrodidae (for example, *Trialeurodes vaporariorum, Bemisia tabaci, Dialeurodes citri*, or *Aleurocanthus spiniferus*);

Coccoidea (for example, *Aonidiella aurantii, Comstockaspis perniciosa, Unaspis citri, Ceroplastes rubens, Icerya purchasi, Planococcus kraunhiae, Pseudococcus longispinis, Pseudaulacaspis pentagona*, or *Brevennia rehi*);

Psyllidae (for example, *Diaphorina citri, Psylla pyrisuga*, or *Bactericerca cockerelli*);

Tingidae (for example, *Stephanitis nasi*);

Cimicidae (for example, *Cimex lectularius*);

*Quesada gigas* (Giant Cicada).

and the others.

Lepidoptera Pests:

Pyralidae (for example, *Chilo suppressalis, Chilo polychrysus* (Darkheaded stm borer), *Tryporyza incertulas, Chilo polychrysus, Scirpophaga innotata, Scirpophaga incertulas* (Yellow stem borer), *Sesamia inferens* (Pink borer), *Rupela albinella, Cnaphalocrocis medinalis, Marasmia patnalis, Marasmia exigna, Notarcha derogata, Plodia interpunctella, Ostrinia furnacalis, Hellula undalis, Pediasia teterrellus, Nymphula depunctalis, Marasmia* spp., *Hydraecia immanis* (Hop vine borer), *Ostrinia nubilalis* (European corn borer), *Elasmopalpus lignosellus* (Lesser cornstalk borer), *Epinotia aporema* (Bean Shoot Borer), *Diatraea saccharalis* (Sugarcane borer), or *Telchin licus* (Giant Sugarcane borer));

Noctuidae (for example, *Spodoptera litura, Spodoptera exigua, Pseudaletia separata, Mamestra brassicae, Sesamia inferens, Spodoptera mauritia, Spodoptera frugiperda, Spodoptera exempta, Agrotis ipsilon, Plusia nigrisigna, Pseudoplusia includens* (Soybean looper), *Trichoplusia* spp., *Heliothis* spp. (for example, *Heliothis virescens*), *Helicoverpa* spp. (for example, *Helicoverpa armigera*), *Anticarsia gammatalis* (Velvetbean caterpillar), or *Alabama argillacea* (Cotton leafworm));

Piezidae (for example, *Pieris rapae*);

Tortricidae (for example, *Adoxophyes* spp., *Grapholita molesta, Leguminivora glycinivorella, Matsumuraeses azukivora, Adoxophyes orana fasciata, Adoxophyes honmai, Homona magnanima, Archips fuscocupreanus*, or *Cydia pomonella*);

Gracillariidae (for example, *Caloptilia theivora* or *Phyllonorycter ringoneella*);

Carposinidae (for example, *Carposina niponensis* or *Ecdytolopha aurantiana* (Citrus fruit borer));

Lyonetiidae (for example, *Leucoptera coffeela* (Coffee Leaf miner) or *Lyonetia* spp.);

Lymantriidae (for example, *Lymantria* spp. or *Euproctis* spp.);

Yponomeutidae (for example, *Plutella xylostella*);

Gelechiidae (for example, *Pectinophora gossypiella* or *Phthorimaea operculella*);

Arctiidae (for example, *Hyphantria cunea*);

and the others.

Thysanoptera Pests:

Thripidae (for example, *Frankliniella occidentalis, Thrips parmi, Scirtothrips dorsalis, Thrips tabaci, Frankliniella intonsa, Frankliniella occidentalis* (western flower *thrips*), *Haplothrips aculeatus*, or *Stenchaetcthrips biformis*);

and the others.

Diptera Pests:

House mosquitoes (*Culex* spp.) (for example, *Culex pipiens pallens, Culex tritaeniorhynchus*, or *Culex quinquefasciatus*);

*Aedes* spp. (for example, *Aedes aegypti* or *Aedes albopictus*);

*Anopheles* spp. (for example, *Anopheles sinensis*);

Chironomidae;

Muscidae (for example, *Musca domestica* or *Muscina stabulans*);

Anthomyiidae (for example, *Delia platura, Delia antiqua*, or *Tetanops myopaeformis*);

Agromyzidae (for example, *Agromyza oryzae, Hydrellia griseola, Liriomyza sativae, Liriomyza trifolii*, or *Chromatomyia horticola*);

Chloropidae (for example, *Chlorops oryzae*);

Tephritidae (for example, *Dacus cucurbitae* or *Ceratitis capitata*);

Ephydridae (for example, *Hydrellia philippina* or *Hydrellia sasakii*);

Drosophilidae;

Phoridae (for example, *Megaselia spiracularis*);

Psychodidae (for example, *Clogmia albipunctata*);

Sciaridae;

Cecidomyiidae (for example, *Mayetiola destructor* or *Orseolia oryzae*);

Diopsidae (for example, *Diopsis macrophthalma*);

Tipulidae (for example, *Tipula oleracea* (Common cranefly) or *Tipula paludosa* (European cranefly));

and the others.

Coleoptera Pests:

Chrysomelidae (for example, *Diabrotica virgifera virgifera, Diabrotica undecimpunctata howardi, Diabrotica barberi, Diabrotica virgifera zeae, Diabrotica balteata LeConte, Diabrotica speciosa, Diabrotica speciosa* (Cucurbit Beetle), *Cerotoma trifurcata, Oulema melanopus, Aulacophora femoralis, Phyllotreta striolata, Leptinotarsa decemlineata, Oulema oryzae, Colaspis brunnea, Chaetocnema pulicaria, Epitrix cucumeris, Dicladispa armigera, Stenolophus lecontei* (Seedcorn beetle), or *Clivinia impressifrons* (Slender seedcorn beetle));

Scarabaeidae (for example, *Anomala cuprea, Anomala rufocuprea, Popillia japonica, Rhizotrogus majalis* (European Chafer), *Bothynus gibbosus* (carrot beetle), *Colaspis brunnea* (Grape *Colaspis*), *Myochrous denticollis* (southern Corn leaf beetle), *Holotrichia* spp., or *Phyllophaga* spp. (for example, *Phyllophaga crinita*));

Erirhinidae (for example, *Sitophilus zeamais, Echinocnemus squameus, Lissorhoptrus oryzophilus*, or *Sphenophorus venatus*);

Curculionidae (for example, *Anthonomus grandis, Sphenophorus callosus* (Southern Corn Billbug), *Sternechus subsignatus* (Soybean stalk weevil), or *Sphenophorus* spp. (for example, *Sphenophorus levis*));

*Epilachna* (for example, *Epilachna vigintioctopunctata*);

Scolytidae (for example, *Lyctus brunneus* or *Tomicus piniperda*);

Bostrychidae;

Ptinidae;

Cerambycidae (for example, *Anoplophora malasiaca* or *Migdolus fryanus*);

Elateridae (*Agriotes* sp., *Aelous* sp., *Anchastus* sp., *Melanotus* sp., *Limonius* sp., *Conoderus* sp., *Ctenicera* sp.) (for example, *Melanotus okinawensis, Agriotes ogurae fuscicollis*, or *Melanotus legatus*);

Staphylinidae (for example, *Paederus fuscipes*);

*Hypothenemus hampei* (Coffee Barry Borer)

and the others.

Orthoptera Pests:

*Locusta migratoria, Gryllotalpa africana, Dociostaurus maroccanus, Chortoicetes terminifera, Nomadacris septemfasciata, Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Twostriped grasshopper), *Melanoplus sanguinipes* (Migratory grasshopper), *Melanoplus femurrubrum* (Red-Legged grasshopper), *Camnula pellucida* (Clearwinged grasshopper), *Schistocerca gregaria, Gastrimargus musicus* (Yellow-winged locust), *Austracris guttulosa* (Spur-throated locust), *Oxya yezoensis, Oxya japonica, Patanga succincta*, or Gryllidae (for example, *Acheta domesticus, Teleogryllus emma*, or *Anabrus simplex* (Mormon cricket));

and the others.

Hymenoptera Pests:

Tenthredinidae (for example, *Athalia rosae* or *Athalia japonica*);

*Solenopsis* spp.;

*Attini* spp. (for example, *Atta capiguara* (Brown leaf-cutting ant));

and the others.

Blattodea Pests:

*Blattella germanica, Periplaneta fuliginosa, Periplaneta americana, Periplaneta brunnea, Blatta orientalis*, and the others.

Termitidae Pests:

*Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis sjostedti, Coptotermes guangzhoensis, Reticulitermes amamianus, Reticulitermes miyatakei, Reticulitermes kanmonensis, Nasutitermes takasagoensis, Pericapritermes nitobei, Sinocapritermes mushae, Cornitermes cumulans*, and the others.

Acarina Pests:

Tetranychidae (for example, *Tetranychus urticae, Tetranychus kanzawai, Panonychus citri, Panonychus ulmi, Oligonychus* spp., or *Brevipalpus phoenicis* (Southern Turkey spider mites));

Eriophyidae (for example, *Aculops pelekassi, Phyllocoptruta citri, Aculops lycopersici, Calacarus carinatus, Acaphylla theavagrans, Eriophyes chibaensis*, or *Aculus schlechtendali*);

Tarsonemidae (for example, *Polyphagotarsonemus latus*);

Tenuipalpidae (for example, *Brevipalpus phoenicis*);

Tuckerellidae;

Ixodidae (for example, *Haemaphysalis longicornis, Haemaphysalis flava, Dermacentor taiwanicus, Dermacentor*

*variabilis, Ixodes ovatus, Ixodes persulcatus, Ixodes scapularis, Amblyomma americanum, Boophilus microplus,* or *Rhipicephalus sanguineus*);

Acaridae (for example, *Tyrophagus putrescentiae* or *Tyrophagus similis*);

Pyroglyphidae (for example, *Dermatophagoides farinae* or *Dermatophagoides ptrenyssnus*);

and the others.

The agent for controlling harmful arthropods of the present invention comprises the Present compound and an inert carrier. The agent for controlling harmful arthropods of the present invention is usually prepared by mixing the Present compound with an inert carrier such as solid carriers, liquid carriers, or gaseous carriers, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations, tablets, or the others. Such formulations may be processed into and used as mosquito repellent coils, electric mosquito repellent mats, liquid mosquito formulations, smoking agents, fumigants, sheet formulations, spot-on formulations, or formulations for oral treatment. Also, the agent for controlling harmful arthropods of the present invention may be mixed with other pesticides, miticides, nematicides, fungicides, plant growth regulators, herbicides, or synergists.

The agent for controlling harmful arthropods of the present invention usually comprises 0.01 to 95% by weight of the Present compound.

Examples of the solid carriers to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate, or hydrated silica), chemical fertilizers (for example, ammonium sulfate, ammonium phosphate, ammonium nitrate, urea, or ammonium chloride), and the others; as well as synthetic resins (for example, polyester resins such as polypropylene, polyacrylonitrile, polymethylmethacrylate, and polyethylene terephthalate; nylon resins such as nylon-6, nylon-11, and nylon-66; polyamide resins; polyvinyl chloride, polyvinylidene chloride, vinyl chloride-propylene copolymers, or the others).

Examples of the above-mentioned liquid carriers include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile or isobutyronitrile); ethers (for example, diisopropyl ether, 1,4-dioxane, DME, diethylene glycol dimethyl ether, diethylene glycol monomethyl ether, propylene glycol monomethyl ether, dipropylene glycol monomethyl ether, or 3-methoxy-3-methyl-1-butanol); amides (for example, DMF or dimethylacetamide); sulfoxides (for example, DMSO); propylene carbonate; and vegetable oils (for example, soybean oil or cottonseed oil).

Examples of the above-mentioned gaseous carriers include fluorocarbon, butane gas, liquefied petroleum gas (LPG), dimethyl ether, and carbon dioxide gas.

Examples of the surfactants include nonionic surfactants such as polyoxyethylene alkyl ethers, polyoxyethylene alkyl aryl ethers, and polyethylene glycol fatty acid esters; and anionic surfactants such as alkyl sulfonates, alkylbenzene sulfonates, and alkyl sulfates.

Examples of the other auxiliary agents for formulation include binders, dispersants, colorants, and stabilizers. Specific examples thereof include casein, gelatin, saccharides (for example, starch, gum arabic, cellulose derivatives, or alginic acid), lignin derivatives, bentonite, water-soluble synthetic polymers (for example, polyvinyl alcohol, polyvinyl pyrrolidone, or polyacrylic acids), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

Examples of base material of the resin formulation include vinyl chloride polymers, polyurethane, and the others, and a plasticizer such as phthalic acid esters (for example, dimethyl phthalate or dioctyl phthalate), adipic acid esters, and stearic acid may be added to these base materials, if necessary. The resin formulation may be prepared by mixing the Present compound with the above-mentioned base material, kneading the mixture in a conventional kneading apparatus, followed by molding it by injection molding, extrusion molding, pressure molding, or the like. The resultant resin formulation may be subjected to further molding, cutting procedure, or the like, if necessary, to be processed into shapes such as a plate, film, tape, net, and string shape. These resin formulations may be processed into animal collars, animal ear tags, sheet products, trap strings, gardening supports, or other products.

Examples of the base material for the poison baits include bait ingredients such as grain powder, vegetable oil, saccharide, and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor, and peanut oil, or the other ingredient.

The method for controlling harmful arthropods of the present invention is conducted by applying an effective amount of the Present compound to a harmful arthropod directly and/or a habitat of pests (for example, plant bodies, soil, an interior of a house, or animal bodies). In the method for controlling harmful arthropods of the present invention, the Present compound is usually used in the form of an agent for controlling harmful arthropods of the present invention.

When an agent for controlling harmful arthropods of the present invention is used for controlling pests in an agricultural field, the application dose as an amount of the Present compound is usually within a range from 1 to 10,000 g per 10,000 m$^2$. The emulsifiable concentrate, the wettable powder, or the flowable formulation etc. of an agent for controlling harmful arthropods of the present invention is usually applied by diluting it with water in such a way that a concentration of the active ingredient is within a range from 0.01 to 10,000 ppm. The granular formulation or the dust formulation etc., is usually applied as itself without diluting it.

These formulations and diluents of the formulations with water may be directly sprayed to a harmful arthropod or a plant such as a crop to be protected from a harmful arthropod, or applied to a soil in a cultivated area to control a pest that inhabits the soil.

Also, a resin formulation processed into sheet shape or string shape may be wrapped around a crop, stretched near a crop, spread on a plant foot soil, or the like.

When the agent for controlling harmful arthropods of the present invention is used to control pests that live inside a house, the application dose as an amount of the Present compound is usually within a range from 0.01 to 1,000 mg per 1 m² of an area to be treated, in the case of using it on a planar area. In the case of using it spatially, the application dose as an amount of the Present compound is usually within a range from 0.01 to 500 mg per 1 m³ of the space to be treated. When the agent for controlling harmful arthropods of the present invention is formulated into emulsifiable concentrates, wettable powders, flowables, or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits, or the others, such formulations are used as itself without diluting it.

When the agent for controlling harmful arthropods of the present invention is used for controlling external parasites of livestock such as cows, horses, pigs, sheep, goats, and chickens, and small animals such as dogs, cats, rats, and mice, the agent of the present invention may be applied to the animals by a known method in the veterinary field. Specifically, when systemic control is intended, the agent of the present invention is administered to the animals as a tablet, a mixture with feed, or a suppository, or by injection (including intramuscular, subcutaneous, intravenous, and intraperitoneal injections), or the like. On the other hand, when non-systemic control is intended, the agent of the present invention is applied to the animals by means of spraying of the oil solution or aqueous solution, pour-on or spot-on treatment, or washing of the animal with a shampoo formulation, or by putting a collar or ear tag made of the resin formulations to the animal, or the like. In the case of administering to an animal body, the dose of the Present compound is usually within a range from 0.1 to 1,000 mg per 1 kg of an animal body weight.

EXAMPLES

The following Examples including Preparation examples, Formulation examples, and Test examples serve to illustrate the present invention more in detail, which should not intend to limit the present invention.

First, regarding the preparation of the Present compound, the Preparation Examples are shown below.

Preparation Example 1-1

To a mixture of 2-chloro-5-methoxypyrimidine (1.5 g), 2-(2-fluoro-4-(trifluoromethyl)phenyl)-4,4,5,5-tetramethyl-1,3,2-dioxaborolan (2.5 g), a 2 M sodium carbonate aqueous solution (11 mL), and DME (10 mL) was added tetrakistriphenylphosphinepalladium(0) (500 mg) under nitrogen atmosphere. The resulting mixture was heated with stirring at 80° C. for 3 hours. To the reaction mixture was added water, and the mixture was extracted with ethyl acetate. The resulting organic layers were washed with saturated brine, and dried over anhydrous sodium sulfate, and concentrated under reduced pressure. The resulting residues were subjected to silica gel chromatography to give the Intermediate compound 1 represented by the following formula (2.0 g).

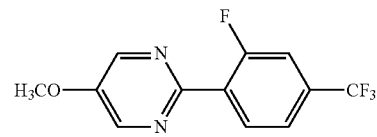 [SMILES: COc1cnc(-c2ccc(C(F)(F)F)cc2F)nc1]

$^1$H-NMR (CDCl$_3$) δ: 8.56 (2H, s), 8.16 (1H, t), 7.52 (1H, d), 7.47 (1H, d), 4.00 (3H, s).

Preparation Example 1-2

To a mixture of the Intermediate compound 1 (2.0 g) and NMP (20 mL) were sequentially added ethanethiol (0.74 mL) and sodium hydride (60%, oily) (440 mg) under ice-cooling. The resulting reaction mixture was warmed to room temperature, and then stirred for 12 hours. To the resulting reaction mixture was added water, and the mixture was extracted with ethyl acetate. The resulting organic layers were washed with saturated brine, and then dried over anhydrous sodium sulfate, and concentrated under reduced pressure. The resulting residues were subjected to silica gel chromatography to give the Intermediate compound 2 represented by the following formula (1.9 g) and the Intermediate compound 3 represented by the following formula (470 mg).

Intermediate Compound 2

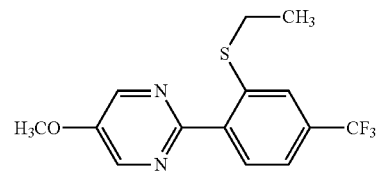 [SMILES: CCSc1cc(C(F)(F)F)ccc1-c1ncc(OC)cn1]

$^1$H-NMR (CDCl$_3$) δ: 8.56 (2H, s), 8.03 (1H, d), 7.59 (1H, s), 7.47 (1H, dd), 3.99 (3H, s), 2.99 (2H, q), 1.34 (3H, t).

Intermediate Compound 3

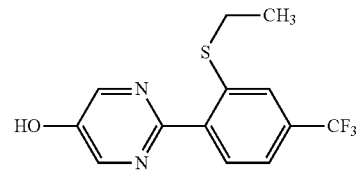 [SMILES: CCSc1cc(C(F)(F)F)ccc1-c1ncc(O)cn1]

$^1$H-NMR (CDCl$_3$) δ: 8.51 (2H, s), 7.94 (1H, d), 7.59 (1H, s), 7.46 (1H, d), 2.98 (2H, q), 1.32 (3H, t).

Preparation Example 1-3

To a mixed solution of the Intermediate compound 2 (1.9 g) and chloroform (10 mL) was added mCPBA (70%) (3.8 g) under ice-cooling. The resulting reaction mixture was warmed to room temperature, and then stirred for 12 hours. To the resulting reaction mixture were sequentially added a saturated sodium thiosulfate aqueous solution and a saturated sodium hydrogen carbonate aqueous solution, and then the mixture was extracted with chloroform. The resulting organic layers were dried over sodium sulfate, and concentrated under reduced pressure. The resulting residues were subjected to silica gel chromatography to give the Intermediate compound 4 represented by the following formula (1.3 g).

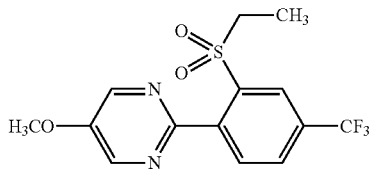 [SMILES: CCS(=O)(=O)c1cc(C(F)(F)F)ccc1-c1ncc(OC)cn1]

$^1$H-NMR (CDCl$_3$) δ: 8.50 (2H, s), 8.40 (1H, s), 7.98 (1H, d), 7.93 (1H, d), 4.00 (3H, s), 3.82 (2H, q), 1.39 (3H, t).

The Intermediate compound 5 represented by the following formula was prepared by using the Intermediate compound 3 instead of the Intermediate compound 2 according to the process described in the Preparation Example 1-3.

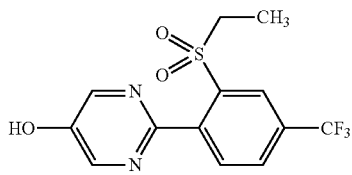 [SMILES: CCS(=O)(=O)c1cc(C(F)(F)F)ccc1-c1ncc(O)cn1]

$^1$H-NMR (CDCl$_3$) δ: 8.41 (1H, s), 8.36 (2H, s), 7.99 (1H, d), 7.94 (1H, d), 6.84 (1H, s), 3.88 (2H, q), 1.42 (3H, t).

Preparation Example 1-4

To a mixture of the Intermediate compound 5 (95 mg), cesium carbonate (110 mg), and NMP (3 mL) was added 2,2,3,3,3-pentafluoropropyl=trifluoromethanesulfonate (99 mg) under ice-cooling. The resulting reaction mixture was stirred at room temperature for 3 hours. To the reaction mixture was added water, and the mixture was extracted with ethyl acetate. The resulting organic layers were sequentially washed with water and saturated brine, and dried over anhydrous sodium sulfate, and concentrated under reduced pressure. The resulting residues were subjected to silica gel chromatography to give the Present compound 1 represented by the following formula (110 mg).

The compounds prepared according to the process described in the Preparation Example 1-4 and the physical properties thereof are shown below.
The compound represented by formula (I-1)

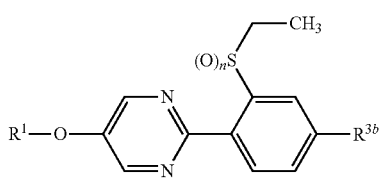

wherein R$^1$, R$^{3b}$, and n represent any one combination indicated in Table 6.

TABLE 6

| Present compound | R$^1$ | R$^{3b}$ | n |
|---|---|---|---|
| 1 | CF$_3$CF$_2$CH$_2$ | CF$_3$ | 2 |
| 2 | CF$_3$CFHCF$_2$CH$_2$ | CF$_3$ | 2 |

Present Compound 1

$^1$H-NMR (CDCl$_3$) δ: 8.58 (2H, s), 8.41 (1H, s), 8.00 (1H, dd), 7.93 (1H, d), 4.62 (2H, td), 3.79 (2H, q), 1.40 (3H, t).

Present Compound 2

$^1$H-NMR (CDCl$_3$) δ: 8.58 (2H, s), 8.41 (1H, s), 8.00 (1H, dd, J=8.0, 1.2 Hz), 7.92 (1H, d, J=7.9 Hz), 5.31-5.08 (1H, m), 4.66-4.44 (2H, m), 3.78 (2H, q, J=7.5 Hz), 1.40 (3H, t, J=7.5 Hz).

Preparation Example 2

To an autoclave reactor was added a mixture of the Intermediate compound 6 (6.5 g), copper iodide (0.67 g), 1,10-phenanthroline (0.058 g), cesium carbonate (1.3 g), 2,2,3,3,3-pentafluoropropanol (1.4 mL), and NMP. The resulting reaction mixture was stirred at 100° C. for 2 hours, and additionally stirred at 130° C. for 2 hours. To the reaction mixture was added water, and the mixture was extracted with ethyl acetate. The resulting organic layers were dried over anhydrous sodium sulfate, and concentrated under reduced pressure. The resulting residues were subjected to silica gel chromatography to give the Intermediate compound 7 represented by the following formula (4.7 g).

The compounds prepared according to the process described in the Preparation Example 2 and the physical properties thereof are shown below.
The compound represented by formula (B-1)

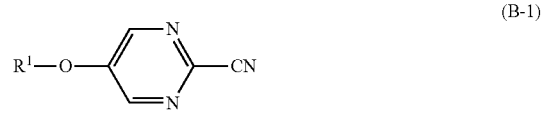

(B-1)

wherein R$^1$ represents any one substituent indicated in Table 7.

TABLE 7

| Intermediate compound | R$^1$ |
|---|---|
| 7 | CF$_3$CF$_2$CH$_2$ |
| 9 | CF$_2$HCF$_2$CH$_2$ |

Intermediate Compound 7

$^1$H-NMR (CDCl$_3$) δ: 8.57 (28, s), 4.64 (2H, td).

Intermediate Compound 9

1H-NMR (CDCl$_3$) δ: 8.56 (2H, s), 6.20-5.87 (1H, m), 4.62-4.55 (2H, m).

Preparation Example 3

To a mixture of a 1.6 M butyllithium-hexane solution (12 mL) and THF (50 mL) was added dropwise a mixture of ethylmethylsulfone (2.2 mL) and THF (5 mL) at 0° C. To the reaction mixture was added dropwise a mixture of the Intermediate compound 7 (4.7 g) and THF (10 mL) at 0° C. The mixture was gradually warmed to room temperature, and then to the reaction mixture was added 2N hydrochloric acid, and the mixture was stirred for 30 minutes. The resulting mixture was extracted with ethyl acetate, and the resulting organic layers were washed with saturated brine. The organic layers were dried over anhydrous sodium sulfate, and then concentrated under reduced pressure to give the Intermediate compound 8 represented by the following formula (0.74 g).

The compounds prepared according to the process described in the Preparation Example 3 and the physical properties thereof are shown below.

The compound represented by formula (C-1)

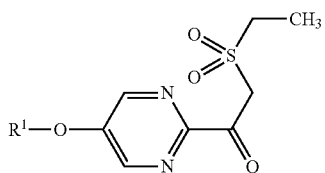

wherein $R^1$ represents any one substituent indicated in Table 8.

TABLE 8

| Intermediate compound | $R^1$ |
|---|---|
| 8 | $CF_3CF_2CH_2$ |
| 10 | $CF_2HCF_2CH_2$ |

Intermediate Compound 8

$^1$H-NMR (CDCl$_3$) δ: 8.66 (2H, s), 4.98 (2H, s), 4.67 (2H, td), 3.30 (2H, q), 1.47 (3H, t).

Intermediate Compound 10

$^1$H-NMR (CDCl$_3$) δ: 8.66 (2H, s), 6.05 (1H, tt), 4.98 (2H, s), 4.62 (2H, tt), 3.30 (2H, q), 1.47 (3H, t).

Preparation Example 4

To a mixture of oxalyl chloride (0.52 mL) and chloroform (5 mL) was added dropwise DMF (0.47 mL) under ice-cooling. The mixture was stirred under ice-cooling for 30 minutes, and then to the mixture was added dropwise butylvinylether (1.6 mL). The resulting mixture was stirred at room temperature for 2 hours. To the mixture was added dropwise a mixture of the Intermediate compound 8 (0.74 g), triethylamine (1.4 mL), and chloroform (5 mL) under ice-cooling. The resulting mixture was stirred at room temperature for 1 hour. The resulting mixture was added to a saturated ammonium chloride aqueous solution, and extracted with chloroform. The resulting organic layers were washed with water and saturated brine, and then dried over anhydrous sodium sulfate, and concentrated under reduced pressure. The resulting residues were diluted with ethanol (30 mL), and then to the mixture was added a 28% ammonia aqueous solution (10 mL) at room temperature. The resulting mixture was heated with stirring at 60° C. for 2.5 hours, and then allowed to cool to room temperature. To the mixture was added water, and the mixture was extracted with ethyl acetate. The resulting organic layers were dried over anhydrous sodium sulfate, and then concentrated under reduced pressure. The resulting residues were subjected to silica gel chromatography to give the Present compound 4 represented by the following formula (410 mg).

The compounds prepared according to the process described in the Preparation Example 4 and the physical properties thereof are shown below.

The compound represented by formula (I-2)

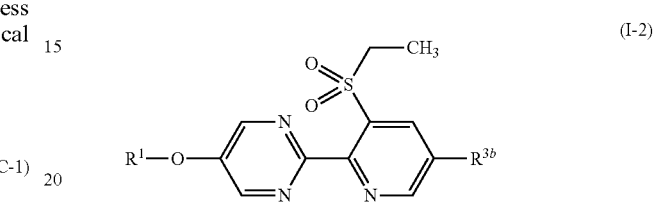

wherein $R^1$ and $R^{3b}$ represent any one combination indicated in Table 9.

TABLE 9

| Present compound | $R^1$ | $R^{3b}$ |
|---|---|---|
| 4 | $CF_3CF_2CH_2$ | H |
| 3 | $CF_2HCF_2CH_2$ | H |
| 5 | $CF_3CF_2CF_2CH_2$ | H |

Present Compound 4

$^1$H-NMR (CDCl$_3$) δ: 8.97 (1H, dd), 8.61 (2H, s), 8.47 (1H, dd), 7.64 (1H, dd), 4.62 (2H, t), 3.78 (2H, q), 1.38 (3H, t).

Present Compound 3

$^1$H-NMR (CDCl$_3$) δ: 8.97 (1H, dd), 8.60 (2H, s), 8.46 (1H, dd), 7.63 (1H, dd), 6.07 (1H, tt), 4.57 (2H, t), 3.78 (2H, q), 1.38 (3H, t).

Present Compound 5

$^1$H-NMR (CDCl$_3$) δ: 8.97 (1H, dd), 8.62 (2H, s), 8.46 (1H, dd), 7.63 (1H, dd), 4.66 (2H, t), 3.78 (2H, q), 1.38 (3H, t).

The compounds represented by formula (100)

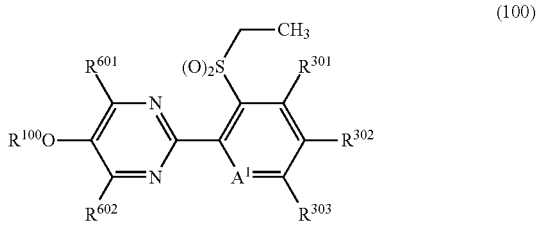

[wherein $R^{301}$, $R^{302}$, $R^{303}$, $R^{601}$, $R^{602}$, $R^{100}$, and $A^1$ represent any one combination indicated in the following Table 10 to Table 35.] may be prepared according to any one of the above processes.

TABLE 10

| Present compound | A¹ | R¹⁰⁰ | R³⁰¹ | R³⁰² | R³⁰³ | R⁶⁰¹ | R⁶⁰² |
|---|---|---|---|---|---|---|---|
| 6 | N | CF₂HCH₂ | H | H | NH₂ | H | H |
| 7 | N | CF₃CF₂CH₂ | H | H | NH₂ | H | H |
| 8 | N | CF₂HCF₂CH₂ | H | H | NH₂ | H | H |
| 9 | N | CF₃CF₂CF₂CH₂ | H | H | NH₂ | H | H |
| 10 | N | CF₃CFHCF₂CH₂ | H | H | NH₂ | H | H |
| 11 | N | CF₂HCH₂ | H | H | NHCH₃ | H | H |
| 12 | N | CF₃CF₂CH₂ | H | H | NHCH₃ | H | H |
| 13 | N | CF₂HCF₂CH₂ | H | H | NHCH₃ | H | H |
| 14 | N | CF₃CF₂CF₂CH₂ | H | H | NHCH₃ | H | H |
| 15 | N | CF₃CFHCF₂CH₂ | H | H | NHCH₃ | H | H |
| 16 | N | CF₂HCH₂ | H | H | N(CH₃)₂ | H | H |
| 17 | N | CF₃CF₂CH₂ | H | H | N(CH₃)₂ | H | H |
| 18 | N | CF₂HCF₂CH₂ | H | H | N(CH₃)₂ | H | H |
| 19 | N | CF₃CF₂CF₂CH₂ | H | H | N(CH₃)₂ | H | H |
| 20 | N | CF₃CFHCF₂CH₂ | H | H | N(CH₃)₂ | H | H |
| 21 | N | CF₂HCH₂ | H | H | N(CH₂CH₃)₂ | H | H |
| 22 | N | CF₃CF₂CH₂ | H | H | N(CH₂CH₃)₂ | H | H |
| 23 | N | CF₂HCF₂CH₂ | H | H | N(CH₂CH₃)₂ | H | H |
| 24 | N | CF₃CF₂CF₂CH₂ | H | H | N(CH₂CH₃)₂ | H | H |
| 25 | N | CF₃CFHCF₂CH₂ | H | H | N(CH₂CH₃)₂ | H | H |
| 26 | N | CF₂HCH₂ | H | H | NHCH₂CF₃ | H | H |
| 27 | N | CF₃CF₂CH₂ | H | H | NHCH₂CF₃ | H | H |
| 28 | N | CF₂HCF₂CH₂ | H | H | NHCH₂CF₃ | H | H |
| 29 | N | CF₃CF₂CF₂CH₂ | H | H | NHCH₂CF₃ | H | H |
| 30 | N | CF₃CFHCF₂CH₂ | H | H | NHCH₂CF₃ | H | H |

TABLE 11

| Present compound | A¹ | R¹⁰⁰ | R³⁰¹ | R³⁰² | R³⁰³ | R⁶⁰¹ | R⁶⁰² |
|---|---|---|---|---|---|---|---|
| 31 | N | CF₂HCH₂ | H | H | Cl | H | H |
| 32 | N | CF₃CF₂CH₂ | H | H | Cl | H | H |
| 33 | N | CF₂HCF₂CH₂ | H | H | Cl | H | H |
| 34 | N | CF₃CF₂CF₂CH₂ | H | H | Cl | H | H |
| 35 | N | CF₃CFHCF₂CH₂ | H | H | Cl | H | H |
| 36 | N | CF₂HCH₂ | H | Cl | H | H | H |
| 37 | N | CF₃CF₂CH₂ | H | Cl | H | H | H |
| 38 | N | CF₂HCF₂CH₂ | H | Cl | H | H | H |
| 39 | N | CF₃CF₂CF₂CH₂ | H | Cl | H | H | H |
| 40 | N | CF₃CFHCF₂CH₂ | H | Cl | H | H | H |
| 41 | N | CF₂HCH₂ | H | H | OCH₃ | H | H |
| 42 | N | CF₃CF₂CH₂ | H | H | OCH₃ | H | H |
| 43 | N | CF₂HCF₂CH₂ | H | H | OCH₃ | H | H |
| 44 | N | CF₃CF₂CF₂CH₂ | H | H | OCH₃ | H | H |
| 45 | N | CF₂CFHCF₂CH₂ | H | H | OCH₃ | H | H |

TABLE 12

| Present compound | A¹ | R¹⁰⁰ | R³⁰¹ | R³⁰² | R³⁰³ | R⁶⁰¹ | R⁶⁰² |
|---|---|---|---|---|---|---|---|
| 46 | N | CF₂HCH₂ | H | H | 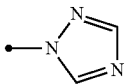 | H | H |
| 47 | N | CF₃CF₂CH₂ | H | H | 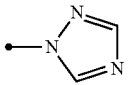 | H | H |
| 48 | N | CF₂HCF₂CH₂ | H | H | 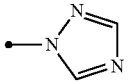 | H | H |
| 49 | N | CF₃CF₂CF₂CH₂ | H | H | 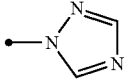 | H | H |
| 50 | N | CF₃CFHCF₂CH₂ | H | H | 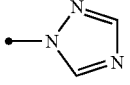 | H | H |
| 51 | N | CF₂HCH₂ | H | H | 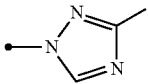 | H | H |

TABLE 12-continued

| Present compound | A¹ | $R^{100}$ | $R^{301}$ | $R^{302}$ | $R^{303}$ | $R^{601}$ | $R^{602}$ |
|---|---|---|---|---|---|---|---|
| 52 | N | $CF_3CF_2CH_2$ | H | H | 3-chloro-1,2,4-triazol-1-yl | H | H |
| 53 | N | $CF_2HCF_2CH_2$ | H | H | 3-chloro-1,2,4-triazol-1-yl | H | H |
| 54 | N | $CF_3CF_2CF_2CH_2$ | H | H | 3-chloro-1,2,4-triazol-1-yl | H | H |
| 55 | N | $CF_3CFHCF_2CH_2$ | H | H | 3-chloro-1,2,4-triazol-1-yl | H | H |

TABLE 13

| Present compound | A¹ | $R^{100}$ | $R^{301}$ | $R^{302}$ | $R^{303}$ | $R^{601}$ | $R^{602}$ |
|---|---|---|---|---|---|---|---|
| 56 | N | $CF_2HCH_2$ | H | H | 3-methoxy-1,2,4-triazol-1-yl | H | H |
| 57 | N | $CF_3CF_2CH_2$ | H | H | 3-methoxy-1,2,4-triazol-1-yl | H | H |
| 58 | N | $CF_2HCF_2CH_2$ | H | H | 3-methoxy-1,2,4-triazol-1-yl | H | H |
| 59 | N | $CF_3CF_2CF_2CH_2$ | H | H | 3-methoxy-1,2,4-triazol-1-yl | H | H |
| 60 | N | $CF_3CFHCF_2CH_2$ | H | H | 3-methoxy-1,2,4-triazol-1-yl | H | H |
| 61 | N | $CF_2HCH_2$ | H | H | 3-amino-1,2,4-triazol-1-yl | H | H |
| 62 | N | $CF_3CF_2CH_2$ | H | H | 3-amino-1,2,4-triazol-1-yl | H | H |
| 63 | N | $CF_2HCF_2CH_2$ | H | H | 3-amino-1,2,4-triazol-1-yl | H | H |

TABLE 13-continued
| Present compound | A¹ | R¹⁰⁰ | R³⁰¹ | R³⁰² | R³⁰³ | R⁶⁰¹ | R⁶⁰² |
|---|---|---|---|---|---|---|---|
| 64 | N | CF₃CF₂CF₂CH₂ | H | H | 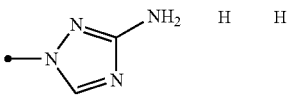 | H | H |
| 65 | N | CF₃CFHCF₂CH₂ | H | H | 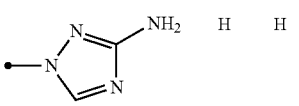 | H | H |
TABLE 14
| Present compound | A¹ | R¹⁰⁰ | R³⁰¹ | R³⁰² | R³⁰³ | R⁶⁰¹ | R⁶⁰² |
|---|---|---|---|---|---|---|---|
| 66 | N | CF₂HCH₂ | H | H | 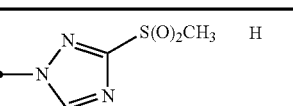 | H | H |
| 67 | N | CF₃CF₂CH₂ | H | H | 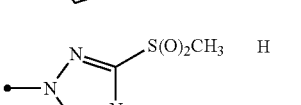 | H | H |
| 68 | N | CF₂HCF₂CH₂ | H | H | 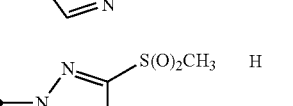 | H | H |
| 69 | N | CF₃CF₂CF₂CH₂ | H | H | 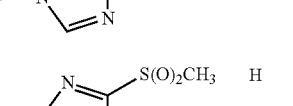 | H | H |
| 70 | N | CF₃CFHCF₂CH₂ | H | H | 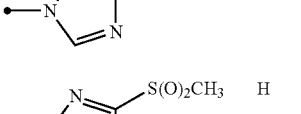 | H | H |
| 71 | N | CF₂HCH₂ | H | H | 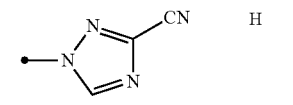 | H | H |
| 72 | N | CF₃CF₂CH₂ | H | H | 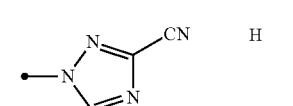 | H | H |
| 73 | N | CF₂HCF₂CH₂ | H | H | 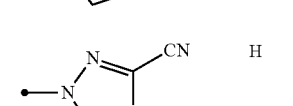 | H | H |
| 74 | N | CF₃CF₂CF₂CH₂ | H | H | 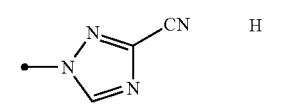 | H | H |
| 75 | N | CF₃CFHCF₂CH₂ | H | H | 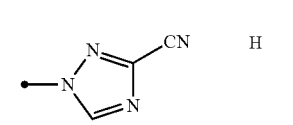 | H | H |

TABLE 15
| Present compound | A¹ | R¹⁰⁰ | R³⁰¹ | R³⁰² | R³⁰³ | R⁶⁰¹ | R⁶⁰² |
|---|---|---|---|---|---|---|---|
| 76 | N | CF₂HCH₂ | H | H | 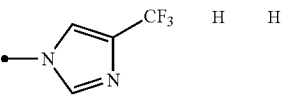 | H | H |
| 77 | N | CF₃CF₂CH₂ | H | H | 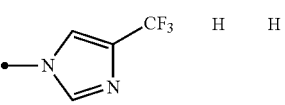 | H | H |
| 78 | N | CF₂HCF₂CH₂ | H | H | 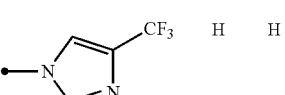 | H | H |
| 79 | N | CF₃CF₂CF₂CH₂ | H | H | 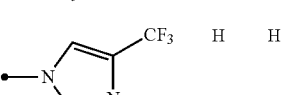 | H | H |
| 80 | N | CF₃CFHCF₂CH₂ | H | H | 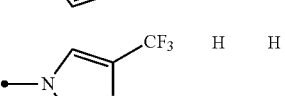 | H | H |
| 81 | N | CF₂HCH₂ | H | H | 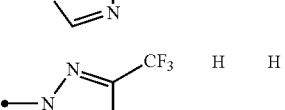 | H | H |
| 82 | N | CF₃CF₂CH₂ | H | H | 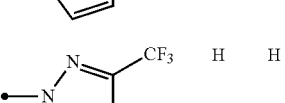 | H | H |
| 83 | N | CF₂HCF₂CH₂ | H | H | 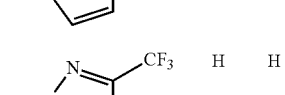 | H | H |
| 84 | N | CF₃CF₂CF₂CH₂ | H | H | 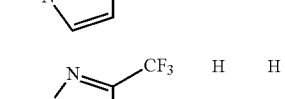 | H | H |
| 85 | N | CF₃CFHCF₂CH₂ | H | H | 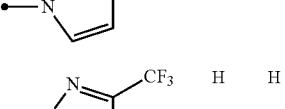 | H | H |
TABLE 16
| Present compound | A¹ | R¹⁰⁰ | R³⁰¹ | R³⁰² | R³⁰³ | R⁶⁰¹ | R⁶⁰² |
|---|---|---|---|---|---|---|---|
| 86 | N | CF₂HCH₂ | H | H | 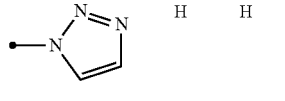 | H | H |
| 87 | N | CF₃CF₂CH₂ | H | H | 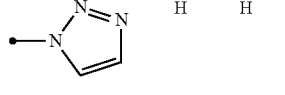 | H | H |
| 88 | N | CF₂HCF₂CH₂ | H | H | 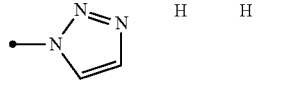 | H | H |

TABLE 16-continued

| Present compound | A¹ | R¹⁰⁰ | R³⁰¹ | R³⁰² | R³⁰³ | R⁶⁰¹ | R⁶⁰² |
|---|---|---|---|---|---|---|---|
| 89 | N | CF₃CF₂CF₂CH₂ | H | H | 1H-1,2,3-triazol-1-yl | H | H |
| 90 | N | CF₃CFHCF₂CH₂ | H | H | 1H-1,2,3-triazol-1-yl | H | H |
| 91 | N | CF₂HCH₂ | H | H | 1H-1,2,4-triazol-1-yl | H | H |
| 92 | N | CF₃CF₂CH₂ | H | H | 1H-1,2,4-triazol-1-yl | H | H |
| 93 | N | CF₂HCF₂CH₂ | H | H | 1H-1,2,4-triazol-1-yl | H | H |
| 94 | N | CF₃CF₂CF₂CH₂ | H | H | 1H-1,2,4-triazol-1-yl | H | H |
| 95 | N | CF₃CFHCF₂CH₂ | H | H | 1H-1,2,4-triazol-1-yl | H | H |

TABLE 17

| Present compound | A¹ | R¹⁰⁰ | R³⁰¹ | R³⁰² | R³⁰³ | R⁶⁰¹ | R⁶⁰² |
|---|---|---|---|---|---|---|---|
| 96 | N | CF₂HCH₂ | H | H | 1,2,4-oxadiazol-3-yl | H | H |
| 97 | N | CF₃CF₂CH₂ | H | H | 1,2,4-oxadiazol-3-yl | H | H |
| 98 | N | CF₂HCF₂CH₂ | H | H | 1,2,4-oxadiazol-3-yl | H | H |
| 99 | N | CF₃CF₂CF₂CH₂ | H | H | 1,2,4-oxadiazol-3-yl | H | H |
| 100 | N | CF₃CFHCF₂CH₂ | H | H | 1,2,4-oxadiazol-3-yl | H | H |
| 101 | N | CF₂HCH₂ | H | H | 5-(trifluoromethyl)-1,3,4-thiadiazol-2-yl | H | H |

TABLE 17-continued

| Present compound | $A^1$ | $R^{100}$ | $R^{301}$ | $R^{302}$ | $R^{303}$ | $R^{601}$ | $R^{602}$ |
|---|---|---|---|---|---|---|---|
| 102 | N | $CF_3CF_2CH_2$ | H | H | 2-(trifluoromethyl)-1,3,4-thiadiazol-5-yl | H | H |
| 103 | N | $CF_2HCF_2CH_2$ | H | H | 2-(trifluoromethyl)-1,3,4-thiadiazol-5-yl | H | H |
| 104 | N | $CF_3CF_2CF_2CH_2$ | H | H | 2-(trifluoromethyl)-1,3,4-thiadiazol-5-yl | H | H |
| 105 | N | $CF_3CFHCF_2CH_2$ | H | H | 2-(trifluoromethyl)-1,3,4-thiadiazol-5-yl | H | H |

TABLE 18

| Present compound | $A^1$ | $R^{100}$ | $R^{301}$ | $R^{302}$ | $R^{303}$ | $R^{601}$ | $R^{602}$ |
|---|---|---|---|---|---|---|---|
| 106 | N | $CF_2HCH_2$ | H | 1H-1,2,4-triazol-1-yl | H | H | H |
| 107 | N | $CF_3CF_2CH_2$ | H | 1H-1,2,4-triazol-1-yl | H | H | H |
| 108 | N | $CF_2HCF_2CH_2$ | H | 1H-1,2,4-triazol-1-yl | H | H | H |
| 109 | N | $CF_3CF_2CF_2CH_2$ | H | 1H-1,2,4-triazol-1-yl | H | H | H |
| 110 | N | $CF_3CFHCF_2CH_2$ | H | 1H-1,2,4-triazol-1-yl | H | H | H |
| 111 | N | $CF_2HCH_2$ | H | 3-chloro-1H-1,2,4-triazol-1-yl | H | H | H |
| 112 | N | $CF_3CF_2CH_2$ | H | 3-chloro-1H-1,2,4-triazol-1-yl | H | H | H |
| 113 | N | $CF_2HCF_2CH_2$ | H | 3-chloro-1H-1,2,4-triazol-1-yl | H | H | H |

TABLE 18-continued
| Present compound | A¹ | R¹⁰⁰ | R³⁰¹ | R³⁰² | R³⁰³ | R⁶⁰¹ | R⁶⁰² |
|---|---|---|---|---|---|---|---|
| 114 | N | CF₃CF₂CF₂CH₂ | H | 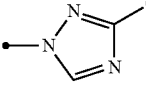 | H | H | H |
| 115 | N | CF₃CFHCF₂CH₂ | H | 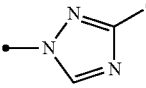 | H | H | H |
TABLE 19
| Present compound | A¹ | R¹⁰⁰ | R³⁰¹ | R³⁰² | R³⁰³ | R⁶⁰¹ | R⁶⁰² |
|---|---|---|---|---|---|---|---|
| 116 | N | CF₂HCH₂ | H | 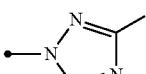 | H | H | H |
| 117 | N | CF₃CF₂CH₂ | H | 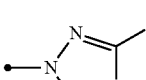 | H | H | H |
| 118 | N | CF₂HCF₂CH₂ | H | 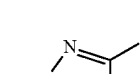 | H | H | H |
| 119 | N | CF₃CF₂CF₂CH₂ | H | 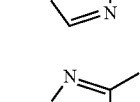 | H | H | H |
| 120 | N | CF₃CFHCF₂CH₂ | H | 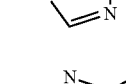 | H | H | H |
| 121 | N | CF₂HCH₂ | H | 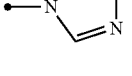 | H | H | H |
| 122 | N | CF₃CF₂CH₂ | H | 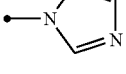 | H | H | H |
| 123 | N | CF₂HCF₂CH₂ | H | 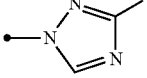 | H | H | H |
| 124 | N | CF₃CF₂CF₂CH₂ | H | 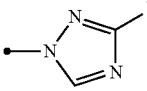 | H | H | H |
| 125 | N | CF₃CFHCF₂CH₂ | H | 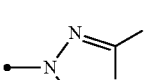 | H | H | H |

TABLE 20

| Present compound | $A^1$ | $R^{100}$ | $R^{301}$ | $R^{302}$ | $R^{303}$ | $R^{601}$ | $R^{602}$ |
|---|---|---|---|---|---|---|---|
| 126 | N | $CF_2HCH_2$ | H | 1,2,4-triazol-1-yl-3-S(O)$_2$CH$_3$ | H | H | H |
| 127 | N | $CF_3CF_2CH_2$ | H | 1,2,4-triazol-1-yl-3-S(O)$_2$CH$_3$ | H | H | H |
| 128 | N | $CF_2HCF_2CH_2$ | H | 1,2,4-triazol-1-yl-3-S(O)$_2$CH$_3$ | H | H | H |
| 129 | N | $CF_3CF_2CF_2CH_2$ | H | 1,2,4-triazol-1-yl-3-S(O)$_2$CH$_3$ | H | H | H |
| 130 | N | $CF_3CFHCF_2CH_2$ | H | 1,2,4-triazol-1-yl-3-S(O)$_2$CH$_3$ | H | H | H |
| 131 | N | $CF_2HCH_2$ | H | 1,2,4-triazol-1-yl-3-CN | H | H | H |
| 132 | N | $CF_3CF_2CH_2$ | H | 1,2,4-triazol-1-yl-3-CN | H | H | H |
| 133 | N | $CF_2HCF_2CH_2$ | H | 1,2,4-triazol-1-yl-3-CN | H | H | H |
| 134 | N | $CF_3CF_2CF_2CH_2$ | H | 1,2,4-triazol-1-yl-3-CN | H | H | H |
| 135 | N | $CF_3CFHCF_2CH_2$ | H | 1,2,4-triazol-1-yl-3-CN | H | H | H |

TABLE 21

| Present compound | $A^1$ | $R^{100}$ | $R^{301}$ | $R^{302}$ | $R^{303}$ | $R^{601}$ | $R^{602}$ |
|---|---|---|---|---|---|---|---|
| 136 | N | $CF_2HCH_2$ | H | imidazol-1-yl-4-CF$_3$ | H | H | H |
| 137 | N | $CF_3CF_2CH_2$ | H | imidazol-1-yl-4-CF$_3$ | H | H | H |

TABLE 21-continued

| Present compound | A$^1$ | R$^{100}$ | R$^{301}$ | R$^{302}$ | R$^{303}$ | R$^{601}$ | R$^{602}$ |
|---|---|---|---|---|---|---|---|
| 138 | N | CF$_2$HCF$_2$CH$_2$ | H | 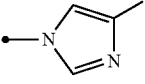 | H | H | H |
| 139 | N | CF$_3$CF$_2$CF$_2$CH$_2$ | H | 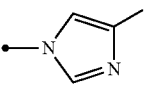 | H | H | H |
| 140 | N | CF$_3$CFHCF$_2$CH$_2$ | H | 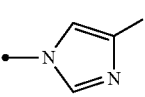 | H | H | H |
| 141 | N | CF$_2$HCH$_2$ | H | 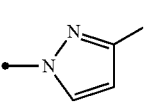 | H | H | H |
| 142 | N | CF$_3$CF$_2$CH$_2$ | H | 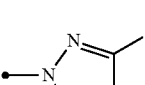 | H | H | H |
| 143 | N | CF$_2$HCF$_2$CH$_2$ | H | 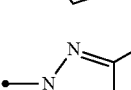 | H | H | H |
| 144 | N | CF$_3$CF$_2$CF$_2$CH$_2$ | H | 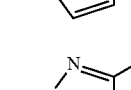 | H | H | H |
| 145 | N | CF$_3$CFHCF$_2$CH$_2$ | H | 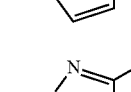 | H | H | H |

TABLE 22

| Present compound | A$^1$ | R$^{100}$ | R$^{301}$ | R$^{302}$ | R$^{303}$ | R$^{601}$ | R$^{602}$ |
|---|---|---|---|---|---|---|---|
| 146 | N | CF$_2$HCH$_2$ | H | 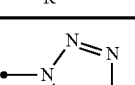 | H | H | H |
| 147 | N | CF$_3$CF$_2$CH$_2$ | H | 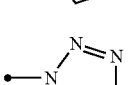 | H | H | H |
| 148 | N | CF$_2$HCF$_2$CH$_2$ | H | 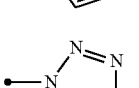 | H | H | H |
| 149 | N | CF$_3$CF$_2$CF$_2$CH$_2$ | H | 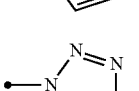 | H | H | H |
| 150 | N | CF$_3$CFHCF$_2$CH$_2$ | H | 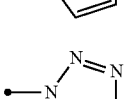 | H | H | H |
| 151 | N | CF$_2$HCH$_2$ | H | 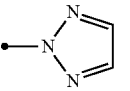 | H | H | H |
| 152 | N | CF$_3$CF$_2$CH$_2$ | H | 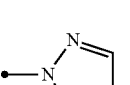 | H | H | H |
| 153 | N | CF$_2$HCF$_2$CH$_2$ | H | 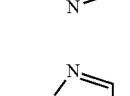 | H | H | H |

TABLE 22-continued

| Present compound | A¹ | R¹⁰⁰ | R³⁰¹ | R³⁰² | R³⁰³ | R⁶⁰¹ | R⁶⁰² |
|---|---|---|---|---|---|---|---|
| 154 | N | CF₃CF₂CF₂CH₂ | H | triazole | H | H | H |
| 155 | N | CF₃CFHCF₂CH₂ | H | triazole | H | H | H |

TABLE 23

| Present compound | A¹ | R¹⁰⁰ | R³⁰¹ | R³⁰² | R³⁰³ | R⁶⁰¹ | R⁶⁰² |
|---|---|---|---|---|---|---|---|
| 156 | N | CF₂HCH₂ | H | ![1,2,4-oxadiazole] | H | H | H |
| 157 | N | CF₃CF₂CH₂ | H | ![1,2,4-oxadiazole] | H | H | H |
| 158 | N | CF₂HCF₂CH₂ | H | ![1,2,4-oxadiazole] | H | H | H |
| 159 | N | CF₃CF₂CF₂CH₂ | H | ![1,2,4-oxadiazole] | H | H | H |
| 160 | N | CF₃CFHCF₂CH₂ | H | ![1,2,4-oxadiazole] | H | H | H |
| 161 | N | CF₂HCH₂ | H | ![thiadiazole-CF₃] | H | H | H |
| 162 | N | CF₃CF₂CH₂ | H | ![thiadiazole-CF₃] | H | H | H |
| 163 | N | CF₂HCF₂CH₂ | H | ![thiadiazole-CF₃] | H | H | H |
| 164 | N | CF₃CF₂CF₂CH₂ | H | ![thiadiazole-CF₃] | H | H | H |
| 165 | N | CF₃CFHCF₂CH₂ | H | ![thiadiazole-CF₃] | H | H | H |

(Note: R³⁰² groups are heterocyclic substituents as depicted in the original figure.)

TABLE 24

| Present compound | A¹ | $R^{100}$ | $R^{301}$ | $R^{302}$ | $R^{303}$ | $R^{601}$ | $R^{602}$ |
|---|---|---|---|---|---|---|---|
| 166 | N | CF$_2$HCH$_2$ | H |  4-F-C$_6$H$_4$- | H | H | H |
| 167 | N | CF$_3$CF$_2$CH$_2$ | H | 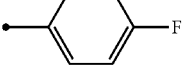 4-F-C$_6$H$_4$- | H | H | H |
| 168 | N | CF$_2$HCF$_2$CH$_2$ | H | 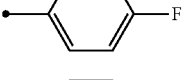 4-F-C$_6$H$_4$- | H | H | H |
| 169 | N | CF$_3$CF$_2$CF$_2$CH$_2$ | H | 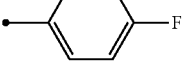 4-F-C$_6$H$_4$- | H | H | H |
| 170 | N | CF$_3$CFHCF$_2$CH$_2$ | H | 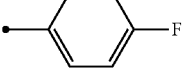 4-F-C$_6$H$_4$- | H | H | H |
| 171 | N | CF$_2$HCH$_2$ | H |  4-Cl-C$_6$H$_4$- | H | H | H |
| 172 | N | CF$_3$CF$_2$CH$_2$ | H | 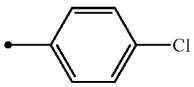 4-Cl-C$_6$H$_4$- | H | H | H |
| 173 | N | CF$_2$HCF$_2$CH$_2$ | H |  4-Cl-C$_6$H$_4$- | H | H | H |
| 174 | N | CF$_3$CF$_2$CF$_2$CH$_2$ | H |  4-Cl-C$_6$H$_4$- | H | H | H |
| 175 | N | CF$_3$CFHCF$_2$CH$_2$ | H | 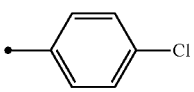 4-Cl-C$_6$H$_4$- | H | H | H |

TABLE 25

| Present compound | A¹ | $R^{100}$ | $R^{301}$ | $R^{302}$ | $R^{303}$ | $R^{601}$ | $R^{602}$ |
|---|---|---|---|---|---|---|---|
| 176 | N | CF$_2$HCH$_2$ | H | 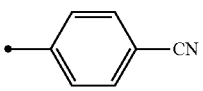 4-CN-C$_6$H$_4$- | H | H | H |
| 177 | N | CF$_3$CF$_2$CH$_2$ | H | 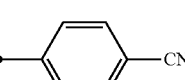 4-CN-C$_6$H$_4$- | H | H | H |
| 178 | N | CF$_2$HCF$_2$CH$_2$ | H | 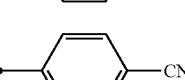 4-CN-C$_6$H$_4$- | H | H | H |
| 179 | N | CF$_3$CF$_2$CF$_2$CH$_2$ | H | 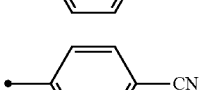 4-CN-C$_6$H$_4$- | H | H | H |

TABLE 25-continued

| Present compound | $A^1$ | $R^{100}$ | $R^{301}$ | $R^{302}$ | $R^{303}$ | $R^{601}$ | $R^{602}$ |
|---|---|---|---|---|---|---|---|
| 180 | N | $CF_3CFHCF_2CH_2$ | H | 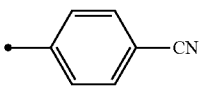 4-CN-C$_6$H$_4$ | H | H | H |
| 181 | N | $CF_2HCH_2$ | H | 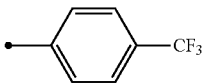 4-CF$_3$-C$_6$H$_4$ | H | H | H |
| 182 | N | $CF_3CF_2CH_2$ | H | 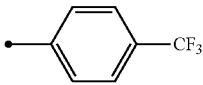 4-CF$_3$-C$_6$H$_4$ | H | H | H |
| 183 | N | $CF_2HCF_2CH_2$ | H | 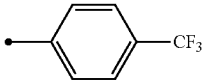 4-CF$_3$-C$_6$H$_4$ | H | H | H |
| 184 | N | $CF_3CF_2CF_2CH_2$ | H | 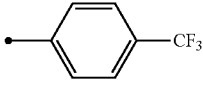 4-CF$_3$-C$_6$H$_4$ | H | H | H |
| 185 | N | $CF_3CFHCF_2CH_2$ | H | 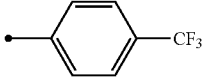 4-CF$_3$-C$_6$H$_4$ | H | H | H |

TABLE 26

| Present compound | $A^1$ | $R^{100}$ | $R^{301}$ | $R^{302}$ | $R^{303}$ | $R^{601}$ | $R^{602}$ |
|---|---|---|---|---|---|---|---|
| 186 | N | $CF_2HCH_2$ | H | 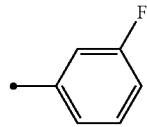 3-F-C$_6$H$_4$ | H | H | H |
| 187 | N | $CF_3CF_2CH_2$ | H | 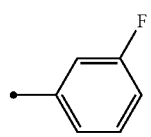 3-F-C$_6$H$_4$ | H | H | H |
| 188 | N | $CF_2HCF_2CH_2$ | H | 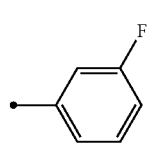 3-F-C$_6$H$_4$ | H | H | H |
| 189 | N | $CF_3CF_2CF_2CH_2$ | H | 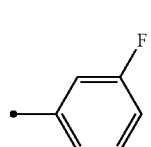 3-F-C$_6$H$_4$ | H | H | H |
| 190 | N | $CF_3CFHCF_2CH_2$ | H | 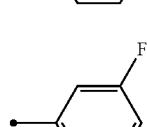 3-F-C$_6$H$_4$ | H | H | H |

TABLE 26-continued

| Present compound | A$^1$ | R$^{100}$ | R$^{301}$ | R$^{302}$ | R$^{303}$ | R$^{601}$ | R$^{602}$ |
|---|---|---|---|---|---|---|---|
| 191 | N | CF$_2$HCH$_2$ | H | 3-CN-phenyl | H | H | H |
| 192 | N | CF$_3$CF$_2$CH$_2$ | H | 3-CN-phenyl | H | H | H |
| 193 | N | CF$_2$HCF$_2$CH$_2$ | H | 3-CN-phenyl | H | H | H |
| 194 | N | CF$_3$CF$_2$CF$_2$CH$_2$ | H | 3-CN-phenyl | H | H | H |
| 195 | N | CF$_3$CFHCF$_2$CH$_2$ | H | 3-CN-phenyl | H | H | H |

TABLE 27

| Present compound | A$^1$ | R$^{100}$ | R$^{301}$ | R$^{302}$ | R$^{303}$ | R$^{601}$ | R$^{602}$ |
|---|---|---|---|---|---|---|---|
| 196 | N | CF$_2$HCH$_2$ | H | pyridin-2-yl | H | H | H |
| 197 | N | CF$_3$CF$_2$CH$_2$ | H | pyridin-2-yl | H | H | H |
| 198 | N | CF$_2$HCF$_2$CH$_2$ | H | pyridin-2-yl | H | H | H |
| 199 | N | CF$_3$CF$_2$CF$_2$CH$_2$ | H | pyridin-2-yl | H | H | H |
| 200 | N | CF$_3$CFHCF$_2$CH$_2$ | H | pyridin-2-yl | H | H | H |
| 201 | N | CF$_2$HCH$_2$ | H | pyrazin-2-yl | H | H | H |

TABLE 27-continued
| Present compound | A¹ | R¹⁰⁰ | R³⁰¹ | R³⁰² | R³⁰³ | R⁶⁰¹ | R⁶⁰² |
|---|---|---|---|---|---|---|---|
| 202 | N | CF₃CF₂CH₂ | H | 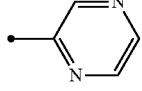 | H | H | H |
| 203 | N | CF₂HCF₂CH₂ | H | 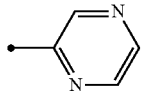 | H | H | H |
| 204 | N | CF₃CF₂CF₂CH₂ | H | 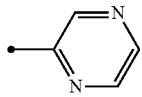 | H | H | H |
| 205 | N | CF₃CFHCF₂CH₂ | H | 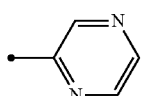 | H | H | H |
TABLE 28
| Present compound | A¹ | R¹⁰⁰ | R³⁰¹ | R³⁰² | R³⁰³ | R⁶⁰¹ | R⁶⁰² |
|---|---|---|---|---|---|---|---|
| 206 | N | CF₂HCH₂ | H | 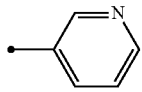 | H | H | H |
| 207 | N | CF₃CF₂CH₂ | H | 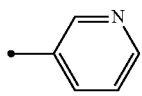 | H | H | H |
| 208 | N | CF₂HCF₂CH₂ | H | 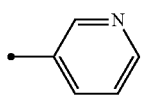 | H | H | H |
| 209 | N | CF₃CF₂CF₂CH₂ | H | 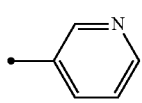 | H | H | H |
| 210 | N | CF₃CFHCF₂CH₂ | H | 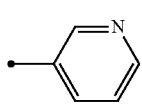 | H | H | H |
| 211 | N | CF₂HCH₂ | H | 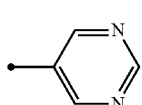 | H | H | H |
| 212 | N | CF₃CF₂CH₂ | H | 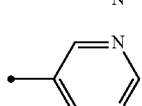 | H | H | H |
| 213 | N | CF₂HCF₂CH₂ | H | 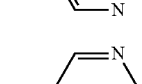 | H | H | H |
| 214 | N | CF₃CF₂CF₂CH₂ | H | 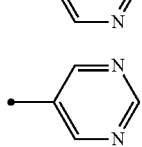 | H | H | H |

TABLE 28-continued

| Present compound | A¹ | R¹⁰⁰ | R³⁰¹ | R³⁰² | R³⁰³ | R⁶⁰¹ | R⁶⁰² |
|---|---|---|---|---|---|---|---|
| 215 | N | CF₃CFHCF₂CH₂ | H | 5-pyrimidinyl | H | H | H |

TABLE 29

| Present compound | A¹ | R¹⁰⁰ | R³⁰¹ | R³⁰² | R³⁰³ | R⁶⁰¹ | R⁶⁰² |
|---|---|---|---|---|---|---|---|
| 216 | N | CF₂HCH₂ | H | 4-(CF₃)-pyridin-2-yl | H | H | H |
| 217 | N | CF₃CF₂CH₂ | H | 4-(CF₃)-pyridin-2-yl | H | H | H |
| 218 | N | CF₂HCF₂CH₂ | H | 4-(CF₃)-pyridin-2-yl | H | H | H |
| 219 | N | CF₃CF₂CF₂CH₂ | H | 4-(CF₃)-pyridin-2-yl | H | H | H |
| 220 | N | CF₃CFHCF₂CH₂ | H | 4-(CF₃)-pyridin-2-yl | H | H | H |
| 221 | N | CF₂HCH₂ | H | 6-(CF₃)-pyridin-3-yl | H | H | H |
| 222 | N | CF₃CF₂CH₂ | H | 6-(CF₃)-pyridin-3-yl | H | H | H |
| 223 | N | CF₂HCF₂CH₂ | H | 6-(CF₃)-pyridin-3-yl | H | H | H |
| 224 | N | CF₃CF₂CF₂CH₂ | H | 6-(CF₃)-pyridin-3-yl | H | H | H |
| 225 | N | CF₃CFHCF₂CH₂ | H | 6-(CF₃)-pyridin-3-yl | H | H | H |

TABLE 30

| Present compound | A¹ | R$^{100}$ | R$^{301}$ | R$^{302}$ | R$^{303}$ | R$^{601}$ | R$^{602}$ |
|---|---|---|---|---|---|---|---|
| 226 | N | CF$_2$HCH$_2$ | H | 2-fluoropyrimidin-5-yl | H | H | H |
| 227 | N | CF$_3$CF$_2$CH$_2$ | H | 2-fluoropyrimidin-5-yl | H | H | H |
| 228 | N | CF$_2$HCF$_2$CH$_2$ | H | 2-fluoropyrimidin-5-yl | H | H | H |
| 229 | N | CF$_3$CF$_2$CF$_2$CH$_2$ | H | 2-fluoropyrimidin-5-yl | H | H | H |
| 230 | N | CF$_3$CFHCF$_2$CH$_2$ | H | 2-fluoropyrimidin-5-yl | H | H | H |
| 231 | N | CF$_2$HCH$_2$ | H | pyrimidin-2-yl | H | H | H |
| 232 | N | CF$_3$CF$_2$CH$_2$ | H | pyrimidin-2-yl | H | H | H |
| 233 | N | CF$_2$HCF$_2$CH$_2$ | H | pyrimidin-2-yl | H | H | H |
| 234 | N | CF$_3$CF$_2$CF$_2$CH$_2$ | H | pyrimidin-2-yl | H | H | H |
| 235 | N | CF$_3$CFHCF$_2$CH$_2$ | H | pyrimidin-2-yl | H | H | H |

TABLE 31

| Present compound | A¹ | R$^{100}$ | R$^{301}$ | R$^{302}$ | R$^{303}$ | R$^{601}$ | R$^{602}$ |
|---|---|---|---|---|---|---|---|
| 236 | N | CF$_2$HCH$_2$ | H | 5-(trifluoromethyl)-2-oxopyridin-1-yl | H | H | H |

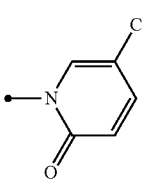

TABLE 31-continued

| Present compound | A¹ | R¹⁰⁰ | R³⁰¹ | R³⁰² | R³⁰³ | R⁶⁰¹ | R⁶⁰² |
|---|---|---|---|---|---|---|---|
| 237 | N | CF₃CF₂CH₂ | H | 5-CF₃-2-oxo-pyridin-1-yl | H | H | H |
| 238 | N | CF₂HCF₂CH₂ | H | 5-CF₃-2-oxo-pyridin-1-yl | H | H | H |
| 239 | N | CF₃CF₂CF₂CH₂ | H | 5-CF₃-2-oxo-pyridin-1-yl | H | H | H |
| 240 | N | CF₃CFHCF₂CH₂ | H | 5-CF₃-2-oxo-pyridin-1-yl | H | H | H |

TABLE 32

| Present compound | A¹ | R¹⁰⁰ | R³⁰¹ | R³⁰² | R³⁰³ | R⁶⁰¹ | R⁶⁰² |
|---|---|---|---|---|---|---|---|
| 241 | N | CF₂HCH₂ | H | OCH₃ | H | H | H |
| 242 | N | CF₃CF₂CH₂ | H | OCH₃ | H | H | H |
| 243 | N | CF₂HCF₂CH₂ | H | OCH₃ | H | H | H |
| 244 | N | CF₃CF₂CF₂CH₂ | H | OCH₃ | H | H | H |
| 245 | N | CF₃CFHCF₂CH₂ | H | OCH₃ | H | H | H |
| 246 | N | CF₂HCH₂ | H | OCH₂CH₃ | H | H | H |
| 247 | N | CF₃CF₂CH₂ | H | OCH₂CH₃ | H | H | H |
| 248 | N | CF₂HCF₂CH₂ | H | OCH₂CH₃ | H | H | H |
| 249 | N | CF₃CF₂CF₂CH₂ | H | OCH₂CH₃ | H | H | H |
| 250 | N | CF₃CFHCF₂CH₂ | H | OCH₂CH₃ | H | H | H |
| 251 | N | CF₂HCH₂ | H | OCH(CH₃)₂ | H | H | H |
| 252 | N | CF₃CF₂CH₂ | H | OCH(CH₃)₂ | H | H | H |
| 253 | N | CF₂HCF₂CH₂ | H | OCH(CH₃)₂ | H | H | H |
| 254 | N | CF₃CF₂CF₂CH₂ | H | OCH(CH₃)₂ | H | H | H |
| 255 | N | CF₃CFHCF₂CH₂ | H | OCH(CH₃)₂ | H | H | H |
| 256 | N | CF₂HCH₂ | H | OCH₂CH₂N(CH₃)₂ | H | H | H |
| 257 | N | CF₃CF₂CH₂ | H | OCH₂CH₂N(CH₃)₂ | H | H | H |
| 258 | N | CF₂HCF₂CH₂ | H | OCH₂CH₂N(CH₃)₂ | H | H | H |
| 259 | N | CF₃CF₂CF₂CH₂ | H | OCH₂CH₂N(CH₃)₂ | H | H | H |
| 260 | N | CF₃CFHCF₂CH₂ | H | OCH₂CH₂N(CH₃)₂ | H | H | H |
| 261 | N | CF₂HCH₂ | H | OCH₂CF₃ | H | H | H |
| 262 | N | CF₃CF₂CH₂ | H | OCH₂CF₃ | H | H | H |
| 263 | N | CF₂HCF₂CH₂ | H | OCH₂CF₃ | H | H | H |
| 264 | N | CF₃CF₂CF₂CH₂ | H | OCH₂CF₃ | H | H | H |
| 265 | N | CF₃CFHCF₂CH₂ | H | OCH₂CF₃ | H | H | H |

TABLE 33

| Present compound | A¹ | R¹⁰⁰ | R³⁰¹ | R³⁰² | R³⁰³ | R⁶⁰¹ | R⁶⁰² |
|---|---|---|---|---|---|---|---|
| 266 | N | CF₂HCH₂ | H | OCH₂CF₃ | H | H | H |
| 267 | N | CF₃CF₂CH₂ | H | OCH₂CF₃ | H | H | H |
| 268 | N | CF₂HCF₂CH₂ | H | OCH₂CF₃ | H | H | H |
| 269 | N | CF₃CF₂CF₂CH₂ | H | OCH₂CF₃ | H | H | H |
| 270 | N | CF₃CFHCF₂CH₂ | H | OCH₂CF₃ | H | H | H |
| 271 | N | CF₂HCH₂ | H | OCH₂CF₂CF₂H | H | H | H |
| 272 | N | CF₃CF₂CH₂ | H | OCH₂CF₂CF₂H | H | H | H |
| 273 | N | CF₂HCF₂CH₂ | H | OCH₂CF₂CF₂H | H | H | H |
| 274 | N | CF₃CF₂CF₂CH₂ | H | OCH₂CF₂CF₂H | H | H | H |
| 275 | N | CF₃CFHCF₂CH₂ | H | OCH₂CF₂CF₂H | H | H | H |
| 276 | N | CF₂HCH₂ | H | OCH₂CF₂CF₃ | H | H | H |
| 277 | N | CF₃CF₂CH₂ | H | OCH₂CF₂CF₃ | H | H | H |
| 278 | N | CF₂HCF₂CH₂ | H | OCH₂CF₂CF₃ | H | H | H |
| 279 | N | CF₃CF₂CF₂CH₂ | H | OCH₂CF₂CF₃ | H | H | H |
| 280 | N | CF₃CFHCF₂CH₂ | H | OCH₂CF₂CF₃ | H | H | H |
| 281 | N | CF₂HCH₂ | H | NHC(O)CH₃ | H | H | H |
| 282 | N | CF₃CF₂CH₂ | H | NHC(O)CH₃ | H | H | H |
| 283 | N | CF₂HCF₂CH₂ | H | NHC(O)CH₃ | H | H | H |
| 284 | N | CF₃CF₂CF₂CH₂ | H | NHC(O)CH₃ | H | H | H |
| 285 | N | CF₃CFHCF₂CH₂ | H | NHC(O)CH₃ | H | H | H |
| 286 | N | CF₂HCH₂ | H | NHC(O)CH₂CH₃ | H | H | H |
| 287 | N | CF₃CF₂CH₂ | H | NHC(O)CH₂CH₃ | H | H | H |
| 288 | N | CF₂HCF₂CH₂ | H | NHC(O)CH₂CH₃ | H | H | H |
| 289 | N | CF₃CF₂CF₂CH₂ | H | NHC(O)CH₂CH₃ | H | H | H |
| 290 | N | CF₃CFHCF₂CH₂ | H | NHC(O)CH₂CH₃ | H | H | H |

TABLE 34

| Present compound | A¹ | R¹⁰⁰ | R³⁰¹ | R³⁰² | R³⁰³ | R⁶⁰¹ | R⁶⁰² |
|---|---|---|---|---|---|---|---|
| 291 | N | CF₂HCH₂ | H | –NHC(O)(cyclopropyl) | H | H | H |
| 292 | N | CF₃CF₂CH₂ | H | –NHC(O)(cyclopropyl) | H | H | H |
| 293 | N | CF₂HCF₂CH₂ | H | –NHC(O)(cyclopropyl) | H | H | H |
| 294 | N | CF₃CF₂CF₂CH₂ | H | –NHC(O)(cyclopropyl) | H | H | H |
| 295 | N | CF₃CFHCF₂CH₂ | H | –NHC(O)(cyclopropyl) | H | H | H |
| 296 | N | CF₂HCH₂ | H | –N(CH₃)C(O)(cyclopropyl) | H | H | H |
| 297 | N | CF₃CF₂CH₂ | H | –N(CH₃)C(O)(cyclopropyl) | H | H | H |

TABLE 34-continued

| Present compound | $A^1$ | $R^{100}$ | $R^{301}$ | $R^{302}$ | $R^{303}$ | $R^{601}$ | $R^{602}$ |
|---|---|---|---|---|---|---|---|
| 298 | N | $CF_2HCF_2CH_2$ | H | —N(CH$_3$)C(O)-cyclopropyl | H | H | H |
| 299 | N | $CF_3CF_2CF_2CH_2$ | H | —N(CH$_3$)C(O)-cyclopropyl | H | H | H |
| 300 | N | $CF_3CFHCF_2CH_2$ | H | —N(CH$_3$)C(O)-cyclopropyl | H | H | H |

TABLE 35

| Present compound | $A^1$ | $R^{100}$ | $R^{301}$ | $R^{302}$ | $R^{303}$ | $R^{601}$ | $R^{602}$ |
|---|---|---|---|---|---|---|---|
| 301 | N | $CF_2HCH_2$ | H | $NHC(O)OCH_3$ | H | H | H |
| 302 | N | $CF_3CF_2CH_2$ | H | $NHC(O)OCH_3$ | H | H | H |
| 303 | N | $CF_2HCF_2CH_2$ | H | $NHC(O)OCH_3$ | H | H | H |
| 304 | N | $CF_3CF_2CF_2CH_2$ | H | $NHC(O)OCH_3$ | H | H | H |
| 305 | N | $CF_3CFHCF_2CH_2$ | H | $NHC(O)OCH_3$ | H | H | H |
| 306 | N | $CF_2HCH_2$ | H | $NHC(O)OCH_2CH_3$ | H | H | H |
| 307 | N | $CF_3CF_2CH_2$ | H | $NHC(O)OCH_2CH_3$ | H | H | H |
| 308 | N | $CF_2HCF_2CH_2$ | H | $NHC(O)OCH_2CH_3$ | H | H | H |
| 309 | N | $CF_3CF_2CF_2CH_2$ | H | $NHC(O)OCH_2CH_3$ | H | H | H |
| 310 | N | $CF_3CFHCF_2CH_2$ | H | $NHC(O)OCH_2CH_3$ | H | H | H |
| 311 | N | $CF_2HCH_2$ | H | $OCH_2CH_2CH_3$ | H | H | H |
| 312 | N | $CF_3CF_2CH_2$ | H | $OCH_2CH_2CH_3$ | H | H | H |
| 313 | N | $CF_2HCF_2CH_2$ | H | $OCH_2CH_2CH_3$ | H | H | H |
| 314 | N | $CF_3CF_2CF_2CH_2$ | H | $OCH_2CH_2CH_3$ | H | H | H |
| 315 | N | $CF_3CFHCF_2CH_2$ | H | $OCH_2CH_2CH_3$ | H | H | H |

Next, the Formulation examples of the Present compound are shown below. The "part(s)" represents "part(s) by weight" unless otherwise specified.

Formulation Example 1

Any one of the Present compounds 1 to 315 (10 parts) is mixed with a mixture of xylene (35 parts) and DMF (35 parts), and then polyoxyethylene styryl phenyl ether (14 parts) and calcium dodecylbenzene sulfonate (6 parts) are added thereto, followed by mixing them to obtain each formulation.

Formulation Example 2

Sodium lauryl sulfate (4 parts), calcium lignin sulfonate (2 parts), synthetic hydrated silicon oxide fine powder (20 parts), and diatomaceous earth (54 parts) are mixed, and further any one of the Present compounds 1 to 315 (20 parts) is added thereto, followed by mixing them to obtain each wettable powder.

Formulation Example 3

To any one of the Present compounds 1 to 315 (2 parts) are added synthetic hydrated silicon oxide fine powder (1 part), calcium lignin sulfonate (2 parts), bentonite (30 parts), and kaolin clay (65 parts), followed by mixing them to obtain a mixture. To the mixture is then added an appropriate amount of water, and the resulting mixture is additionally stirred, and subjected to granulation with a granulator and forced-air drying to obtain each granular formulation.

Formulation Example 4

Any one of the Present compounds 1 to 315 (1 part) is mixed with an appropriate amount of acetone, and then synthetic hydrated silicon oxide fine powder (5 parts), isopropyl acid phosphate (0.3 parts), and kaolin clay (93.7 parts) are added thereto, followed by mixing with stirring thoroughly and removal of acetone from the mixture by evaporation to obtain each powder formulation.

Formulation Example 5

A mixture of polyoxyethylene alkyl ether sulfate ammonium salt and white carbon (weight ratio of 1:1) (35 parts), any one of the Present compounds 1 to 315 (10 parts), and water (55 parts) are mixed, followed by finely groundings by a wet grinding method to obtain each flowable formulation.

Formulation Example 6

Any one of the Present compounds 1 to 315 (0.1 part) is mixed with a mixture of xylene (5 parts) and trichloroethane (5 parts), and the resulting mixture is then mixed with kerosene (89.9 parts) to obtain each oil solution.

Formulation Example 7

Any one of the Present compounds 1 to 315 (10 mg) is mixed with acetone (0.5 mL), and the solution is added dropwise to a solid feed powder for an animal (solid feed powder for rearing and breeding CE-2, manufactured by CLEA Japan, Inc.) (5 g), followed by mixing the resulting mixture uniformly, and then by drying it by evaporation of acetone to obtain each poison bait.

Formulation Example 8

Any one of the Present compounds 1 to 315 (0.1 part) and Neothiozole (manufactured by Chuo Kasei Co., Ltd.) (49.9 parts) are placed into an aerosol can. After mounting an aerosol valve, dimethyl ether (25 parts) and LPG (25 parts) are filled, followed by shaking and further mounting an actuator to obtain each oily aerosol.

Formulation Example 9

A mixture of any one of the Present compounds 1 to 315 (0.6 parts), BHT (2,6-di-tert-butyl-4-methylphenol) (0.01 part), xylene (5 parts), kerosene (3.39 parts), and an emulsifier {Rheodol MO-60 (manufactured by Kao Corporation)} (1 part), and distilled water (50 parts) are filled into an aerosol container, and a valve part is attached. Then, a propellant (LPG) (40 parts) is filled therein through the valve under pressure to obtain each aqueous aerosol.

Formulation Example 10

Any one of the Present compounds 1 to 4 (0.1 g) is mixed with propylene glycol (2 mL), and the resulting solution is impregnated into a ceramic plate having a size of 4.0 cm×4.0 cm and a thickness of 1.2 cm to obtain each thermal fumigant.

Formulation Example 11

Any one of the Present compounds 1 to 315 (5 parts) and ethylene-methyl methacrylate copolymer (the ratio of the methyl methacrylate in the copolymer: 10% by weight, Acryft (registered trademark) WD 301, manufactured by Sumitomo Chemical Co. Ltd.) (95 parts) are melted and kneaded with a closed type pressure kneader (manufactured by Moriyama Co., Ltd.), and the resulting kneaded product is extruded from an extrusion molding machine through a molding die to obtain each rod-shaped molded product having a length of 15 cm and a diameter of 3 mm.

Formulation Example 12

Any one of the Present compounds 1 to 315 (5 parts) and flexible vinyl chloride resin (95 parts) are melted and kneaded with a closed type pressure kneader (manufactured by Moriyama Co., Ltd.), and the resulting kneaded product is extruded from an extrusion molding machine through a molding die to obtain each rod-shaped molded product having a length of 15 cm and a diameter of 3 mm.

Formulation Example 13

Any one of the Present compounds 1 to 315 (100 mg), lactose (68.75 mg), corn starch (237.5 mg), microcrystalline cellulose (43.75 mg), polyvinylpyrrolidone (18.75 mg), sodium carboxymethyl starch (28.75 mg), and magnesium stearate (2.5 mg) are mixed, and the resulting mixture is compressed to an appropriate size to obtain each tablet.

Formulation Example 14

Any one of the Present compounds 1 to 315 (25 mg), lactose (60 mg), corn starch (25 mg), carmellose calcium (6 mg), and an appropriate amount of a 5% hydroxypropyl methylcellulose aqueous solution are mixed, and the resulting mixture is filled into a hard shell gelatin capsule or a hydroxypropyl methylcellulose capsule to obtain each capsule.

Formulation Example 15

To any one of the Present compounds 1 to 315 (100 mg), fumaric acid (500 mg), sodium chloride (2,000 mg), methylparaben (150 mg), propylparaben (50 mg), granulated sugar (25,000 mg), sorbitol (70% solution) (13,000 mg), Veegum K (manufactured by Vanderbilt Co.) (100 mg), perfume (35 mg), and a coloring agent (500 mg) is added distilled water so that the final volume is set to be 100 mL, followed by mixing them to obtain each suspension for oral administration.

Formulation Example 16

Any one of the Present compounds 1 to 315 (5% by weight) is mixed with an emulsifier (5% by weight), benzyl alcohol (3% by weight), and propylene glycol (30% by weight), and phosphate buffer is added thereto so that the pH of the solution is set to be 6.0 to 6.5, and then water is added thereto as the rest parts to obtain each solution for oral administration.

Formulation Example 17

To a mixture of fractional distillated palm oil (57% by weight) and polysorbate 85 (3% by weight) is added aluminum distearate (5% by weight), and the mixture is dispersed by heating. The resulting mixture is cooled to room temperature, and saccharin (25% by weight) is dispersed in the oil vehicle. Any one of the Present compounds 1 to 315 (10% by weight) is divided thereto to obtain each paste formulation for oral administration.

Formulation Example 18

Any one of the Present compounds 1 to 315 (5% by weight) is mixed with a limestone filler (95% by weight), followed by a wet granulation of the resulting mixture to obtain each granule for oral administration.

Formulation Example 19

Any one of the Present compounds 1 to 315 (5 parts) is mixed with diethylene glycol monoethyl ether (80 parts), and propylene carbonate (15 parts) is added thereto, and the resulting mixture is mixed to obtain each spot-on solution.

Formulation Example 20

Any one of the Present compounds 1 to 315 (10 parts) is mixed with diethylene glycol monoethyl ether (70 parts), and 2-octyldodecanol (20 parts) is added thereto, and the resulting mixture is mixed to obtain each pour-on solution.

Formulation Example 21

To any one of the Present compounds 1 to 315 (0.5 parts) are added Nikkol (registered trademark) TEALS-42 (manufactured by Nikko Chemicals Co., Ltd.: a 42% triethanolamine lauryl sulfate aqueous solution) (60 parts) and propylene glycol (20 parts), and the resulting mixture is mixed with stirring thoroughly to obtain a homogeneous solution, and water (19.5 parts) is then added thereto and the resulting mixture is further mixed with stirring thoroughly to obtain each homogeneous solution of shampoo formulation.

Formulation Example 22

Any one of the Present compounds 1 to 315 (0.15% by weight), animal feed (95% by weight), and a mixture (4.85% by weight) consisting of dibasic calcium phosphate, diatomaceous earth, Aerosil, and carbonate (or chalk) are mixed with stirring thoroughly to obtain each premix for animal feed.

Formulation Example 23

Any one of the Present compounds 1 to 315 (7.2 g) and Hosco (registered trademark) S-55 (manufactured by Maruishi Pharmaceuticals) (92.8 g) are mixed at 100° C., and the resulting mixture is poured into a suppository mold, followed by performing a cooling solidification to obtain each suppository.

Next, Test examples are used to show efficacies of the Present compounds on controlling harmful arthropods. In the following Test examples, the tests were carried out at 25° C.

Test Example 1

Each test compound is formulated according to the process described in the Formulation example 5 to obtain each formulation, and water containing a spreader (0.03% by volume) is added thereto to prepare a diluted solution containing a prescribed concentration of each test compound.

Cucumber (*Cucumis sativus*) seedlings (on the developmental stage of the second true leaf) are planted in a plastic cup and approximately 30 heads of cotton aphid (*Aphis gossypii*) (all stages of life) are released onto the cucumber seedlings. After 1 day, each of said diluted solution is sprayed into the seedlings in a ratio of 10 mL/seedling. After additional 5 days, the number of the surviving insects is examined and the controlling value is calculated by the following equation.

Controlling value (%) = $\{1-(Cb \times Tai)/(Cai \times Tb)\} \times 100$ wherein the symbols in the formula represent the following meanings.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;
Here the "untreated group" represents a group where a similar treatment procedure to that of the treated group except not using each test compound is done.

The results of the test that was carried out according to the Test example 1 are shown below.

When the prescribed concentration was 500 ppm, each of the following Present compounds used as a test compound showed 90% or greater as the controlling value.
Present compound number: 1, 3, and 4

The results of the test that was carried out according to the Test example 1 are shown below.

When the prescribed concentration was 200 ppm, each of the following Present compounds used as a test compound showed 90% or greater as the controlling value.
Present compound number: 3, 4, and 5

Test Example 2

Each test compound is formulated according to the process described in the Formulation example 5 to obtain each formulation, and water is added thereto to prepare a diluted solution containing a prescribed concentration of each test compound.

Cucumber seedlings (on the developmental stage of the second true leaf) are planted in a plastic cup, and each of the diluted solutions in the ratio of 5 mL/seedling is irrigated into the plant foot. After 7 days, approximately 30 heads of cotton aphid (*Aphis gossypii*) (all stages of life) are released onto the surfaces of leaves of the cucumber seedlings. After additional 6 days, the number of the surviving insects is examined and the controlling value is calculated by the following equation.

Controlling value (%) = $\{1-(Cb \times Tai)/(Cai \times Tb)\} \times 100$ wherein the symbols in the formula represent the following meanings.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;
Here the "untreated group" represents a group where a similar treatment procedure to that of the treated group except not using each test compound is done.

The results of the test that was carried out according to the Test example 2 are shown below.

When the prescribed concentration was 200 ppm, each of the following Present compounds used as a test compound showed 90% or greater as the controlling value.
Present compound number: 3, 4, and 5

Test Example 3

Each test compound is formulated according to the process described in the Formulation example 5 to obtain each formulation, and water containing a spreader (0.03% by volume) is added thereto to prepare a diluted solution containing a prescribed concentration of each test compound.

Rice (*Oryza sativa*) seedlings (on the developmental stage of the second true leaf) are planted in a plastic cup, and each of the diluted solutions is sprayed into the seedlings in a ratio of 10 mL/seedling. Thereafter, 20 heads of the 3rd instar larvae of brown planthopper (*Nilaparvata lugens*) are released onto the rice seedlings. After 6 days, the number of the surviving insects is examined and the mortality of insects is calculated by the following equation.

$$\text{Mortality (\%)}=(1-\text{Number of surviving insects}/20)\times 100$$

The results of the test that was carried out according to the Test example 3 are shown below.

When the prescribed concentration was 500 ppm, each of the following Present compounds used as a test compound showed 90% or greater as the controlling value.
Present compound number: 3 and 4

The results of the test that was carried out according to the Test example 3 are shown below.

When the prescribed concentration was 200 ppm, each of the following Present compounds used as a test compound showed 90% or greater as the controlling value.
Present compound number: 4 and 5

Test Example 4

Each test compound is formulated according to the process described in the Formulation example 5 to obtain each formulation, and water is added thereto to prepare a diluted solution containing a prescribed concentration of each test compound.

Each of the diluted solutions (5 mL) is added to a plastic cup, and therein is installed Rice seedlings (on the developmental stage of the second true leaf) planted in a plastic cup having a hole in the bottom. After 7 days, 20 heads of the 3rd instar larvae of brown planthopper (*Nilaparvata lugens*) are released onto the rice seedlings. After additional 6 days, the number of the surviving insects is examined and the mortality of insects is calculated by the following equation.

$$\text{Mortality (\%)}=\{1-\text{Number of surviving insects}/20\}\times 100$$

The results of the test that was carried out according to the Test example 4 are shown below.

When the prescribed concentration was 200 ppm, each of the following Present compounds used as a test compound showed 90% or greater as the controlling value.
Present compound number: 3, 4, and 5

Test Example 5

Each test compound is formulated according to the process described in the Formulation example 5 to obtain each formulation, and water is added thereto to prepare a diluted solution containing a prescribed concentration of each test compound.

An artificial diet (Insecta LF, manufactured by Nosan Corporation) (7.7 g) is placed in a plastic cup, and thereto is irrigated each of the diluted solutions (2 mL). Five (5) heads of the 4th instar larvae of tobacco cutworm (*Spodoptera litura*) are released onto the artificial diet, and the cup is covered with a lid. After 5 days, the number of the surviving insects is counted, and the mortality of insects is calculated by the following equation.

$$\text{Mortality (\%)}=(1-\text{Number of surviving insects}/5)\times 100$$

The results of the test that was carried out according to the Test example 5 are shown below.

When the prescribed concentration was 500 ppm, each of the following Present compounds used as a test compound showed 80% or greater as the mortality of insects.
Present compound number: 1 and 2

Test Example 6

Each test compound is formulated according to the process described in the Formulation example 5 to obtain each formulation, and water containing a spreader (0.03% by volume) is added thereto to prepare a diluted solution containing a prescribed concentration of each test compound.

Cabbage (*Brassicae oleracea*) seedlings (on the developmental stage of the second to third true leaf) are planted in a plastic cup, and each of the diluted solutions is sprayed into the seedlings in a ratio of 20 mL/seedling. Thereafter, the stem and leaf of the seedling are cut out, and placed into a plastic cup lined with a filter paper. Five (5) heads of the 2nd instar larvae of cabbage moth (*Plutella xylostella*) are released into the cup, and the cup is covered with a lid. After 5 days, the number of the surviving insects is counted, and the mortality of insects is calculated by the following equation.

$$\text{Mortality (\%)}=(1-\text{Number of surviving insects}/5)\times 100$$

The results of the test that was carried out according to the Test example 6 are shown below.

When the prescribed concentration was 500 ppm, each of the following Present compounds used as a test compound showed 80% or greater as the mortality of insects.
Present compound number: 1, 2, 3, and 4

Test Example 8

Each test compound is formulated according to the process described in the Formulation example 5 to obtain each formulation, and water containing a spreader (0.03% by volume) is added thereto to prepare a diluted solution containing a prescribed concentration of each test compound.

Cabbage seedlings (on the developmental stage of the third to fourth true leaf) are planted in a plastic cup, and each of the diluted solutions is sprayed into the seedlings in a ratio of 20 mL/seedling. Thereafter, 10 heads of the 3rd instar larvae of cabbage moth (*Plutella xylostella*) are released into the cabbage seedlings, and held in a plastic container covered with a net. After 5 days, the number of the surviving insects is counted, and the mortality of insects is calculated by the following equation.

$$\text{Mortality (\%)}=(1-\text{Number of surviving insects}/10)\times 100$$

The results of the test that was carried out according to the Test example 8 are shown below.

When the prescribed concentration was 200 ppm, each of the following Present compounds used as a test compound showed 90% or greater as the mortality of insects.
Present compound number: 1, 2, 4, and 5

Test Example 9

Each test compound is dissolved into a mixed solution (50 µL) of polyoxyethylene sorbitan mono-cocoate:acetone (at a volume ratio of polyoxyethylene sorbitan mono-cocoate:acetone=5:95) per 1 mg of the test compound, and water containing a spreader (0.03% by volume) is added thereto to prepare a diluted solution containing a prescribed concentration of each test compound.

Seeds of corns (Zea mays) are inoculated onto a tray lined with wet Kimwipes. After the corns are grown for 5 days, the entire seedlings of the corns are immersed into each of the diluted solutions for 30 seconds. Thereafter, two seedlings are placed into each plastic petri dish (diameter: 90 mm), and 10 heads of the 2nd instar larvae of western corn rootworm (Diabrotica virgifera virgifera) are released into the dish, and the dish is covered with a lid. After 5 days, the number of the dead insects is counted, and the mortality of insects is calculated by the following equation.

Mortality (%)=(Number of dead insects/10)×100

The results of the test that was carried out according to the Test example 9 are shown below.

When the prescribed concentration was 500 ppm, each of the following Present compounds used as a test compound showed 80% or greater as the mortality.
Present compound number: 2, 3, 4, and 5

Test Example 10

Each test compound is dissolved into a mixed solution (10 μL) of xylene, DMF, and a surfactant (at a volume ratio of xylene:DMF:surfactant=4:4:1) per 1 mg of the test compound, and water containing a spreader (0.03% by volume) is added thereto to prepare a diluted solution containing a prescribed concentration of each test compound.

Cucumber seedlings (on the developmental stage of the second to third true leaf) are planted in a plastic cup, and each of the diluted solutions is sprayed into the seedlings in the ratio of 10 mL/seedling. Thereafter, the second leaves are cut out and placed into a plastic cup, and 10 heads of the 2nd instar larvae of cucurbit leaf beetle (Aulacophora femoralis) are released into the cup, and the cup is covered with a lid. After 5 days, the number of the dead insects is counted, and the mortality of insects is calculated by the following equation.

Mortality (%)=(Number of dead insects/10)×100

The result of the test that was carried out according to the Test example 10 is shown below.

When the prescribed concentration was 50 ppm, the following Present compound used as a test compound showed 80% or greater as the mortality.
Present compound number: 2

Test Example 11

Each test compound is formulated according to the process described in the Formulation example 5 to obtain each formulation, and water is added thereto to prepare a diluted solution containing a prescribed concentration of each test compound.

A bottom of a plastic cup having a diameter of 5.5 cm is lined with the same size of a filter paper, and each of the diluted solution (0.7 mL) is added dropwise on the filter paper, and sucrose (30 mg) is homogeneously placed into the plastic cup as a bait. Ten (10) heads of female adult housefly (Musca domestica) are released into the plastic cup, and the cup is covered with a lid. After 24 hours, life or death of the housefly is examined and the mortality of insects is calculated by the following equation.

Mortality of insects (%)=(Number of dead insects/Number of test insects)×100

INDUSTRIAL APPLICABILITY

The Present compounds have excellent control efficacies against harmful arthropods.

The invention claimed is:
1. A compound represented by formula (I) or an N-oxide thereof:

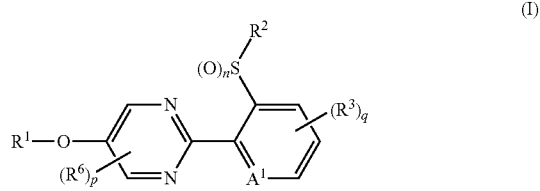

wherein:
$A^1$ represents a nitrogen atom or a $CR^4$;
$R^4$ represents a hydrogen atom, a $OR^{27}$, a $NR^{27}R^{28}$, a cyano group, a nitro group, or a halogen atom;
$R^1$ represents a C2-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;
$R^2$ represents a C1-C6 alkyl group optionally having one or more halogen atoms, a cyclopropylmethyl group, or a cyclopropyl group;
q represents 0, 1, 2, or 3
wherein when q represents 1, 2, or 3, $R^3$ represents a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{29}NR^{11}R^{12}$, a $NR^{24}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, a $C(O)NR^{11}R^{12}$, a cyano group, a nitro group, or a halogen atom, and
wherein when q represents 2 or 3, two or three $R^3$ may be identical to or different from each other;
p represents 0, 1, or 2
wherein when p represents 1 or 2, $R^6$ represents a C1-C6 alkyl group optionally having one or more halogen atoms, a $OR^{18}$, a $NR^{18}R^{19}$, a cyano group, a nitro group, or a halogen atom, and
wherein when p represents 2, two $R^6$ may be identical to or different from each other;
$R^{11}$, $R^{17}$, $R^{18}$, $R^{19}$, $R^{24}$, and $R^{29}$ represent each independently a hydrogen atom or a C1-C6 chain hydrocarbon group optionally having one or more halogen atoms;
$R^{12}$ represents a hydrogen atom, a C1-C6 chain hydrocarbon group optionally having one or more halogen atoms, a C1-C6 alkyl group having one substituent selected from Group F, or a $S(O)_2R^{23}$;

$R^{23}$ represents a C1-C6 chain hydrocarbon group optionally having one or more halogen atoms or a phenyl group optionally having one or more substituents selected from Group D;

$R^{11a}$ and $R^{12a}$ are combined with the nitrogen atom to which they are attached to represent a 3-7 membered nonaromatic heterocyclic group optionally having one or more substituents selected from Group E, wherein the 3-7 membered nonaromatic heterocyclic group represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring;

$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a 5 or 6 membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group, wherein the phenyl moiety in the phenyl C1-C3 alkyl group may optionally have one or more substituents selected from Group D;

$R^{15}$ and $R^{16}$ represent each independently a C1-C6 alkyl group optionally having one or more halogen atoms;

$R^{27}$ and $R^{28}$ represent each independently a hydrogen atom or a C1-C6 alkyl group optionally having one or more halogen atoms;

n and y represent each independently 0, 1, or 2;

x represents 0 or 1;

Group B is selected from the group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group C is selected from the group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D is selected from the group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom, wherein $R^{21}$ and $R^{22}$ represent each independently a C1-C6 alkyl group optionally having one or more halogen atoms;

Group E is selected from the group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F is selected from the group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a 5 or 6 membered aromatic heterocyclic group optionally having one or more substituents selected from Group D, a C3-C7 cycloalkyl group optionally having one or more halogen atoms, and a 3-7 membered nonaromatic heterocyclic group optionally having one or more substituents selected from Group C;

Group G is selected from the group consisting of a halogen atom and a C1-C6 haloalkyl group.

2. The compound according to claim 1, wherein
$R^4$ represents a hydrogen atom or a halogen atom; and
$R^3$ represents a C1-C6 chain hydrocarbon group optionally having one or more halogen atoms, a phenyl group optionally having one or more substituents selected from Group D, a 6 membered aromatic heterocyclic group comprising 1 to 2 nitrogen atoms, wherein said 6 membered aromatic heterocyclic group may optionally have one or more substituents selected from Group D, a 5 membered aromatic heterocyclic group comprising 1 to 4 nitrogen atoms, wherein said 5 membered aromatic heterocyclic group may optionally have one or more substituents selected from Group D, a $OR^{12}$, a $NR^{11}R^{12}$, or a halogen atom.

3. The compound according to claim 1, wherein
$R^3$ represents a C1-C6 alkyl group having one or more halogen atoms, a $OR^{12}$, a $NR^{11}R^{12}$, or a halogen atom; and
$R^{11}$ and $R^{12}$ represent each independently a hydrogen atom or a C1-C3 alkyl group optionally having one or more halogen atoms.

4. The compound according to claim 1, wherein
q represents 0; and
$R^4$ represents a hydrogen atom.

5. The compound according to claim 1, wherein p represents 0.

6. The compound according to claim 1, wherein $R^1$ represents a C2-C10 haloalkyl group.

7. The compound according to claim 1, wherein $R^1$ represents a C2-C10 fluoroalkyl group.

8. The compound according to claim 1, wherein $R^1$ represents a C3-C5 alkyl group having four or more fluorine atoms.

9. The compound according to claim 1, wherein $R^2$ represents a C1-C6 alkyl group optionally having one or more halogen atoms.

10. The compound according to claim 1, wherein $R^2$ represents an ethyl group.

11. The compound according to claim 1, wherein
$R^1$ represents a C2-C10 haloalkyl group;
$R^2$ represents an ethyl group;
q represents 0 or 1;
$R^3$ represents a C1-C6 alkyl group optionally having one or more halogen atoms, or a halogen atom;
p represents 0 or 1; and
$R^6$ represents a C1-C6 alkyl group optionally having one or more halogen atoms, or a halogen atom.

12. The compound according to claim 1, wherein
$R^1$ represents a C3-C5 alkyl group having four or more fluorine atoms;
$R^2$ represents an ethyl group;
q represents 0; and
p represents 0.

13. A composition for controlling a harmful arthropod comprising the compound according to claim 1 and an inert carrier.

14. A method for controlling a harmful arthropod which comprises applying an effective amount of the compound according to claim 1 to a harmful arthropod or a habitat where a harmful arthropod lives.

* * * * *